(12) United States Patent
Saffron et al.

(10) Patent No.: US 11,566,332 B2
(45) Date of Patent: Jan. 31, 2023

(54) ELECTROCATALYTIC HYDROGENATION AND HYDRODEOXYGENATION OF OXYGENATED AND UNSATURATED ORGANIC COMPOUNDS

(71) Applicant: BOARD OF TRUSTEES OF MICHIGAN STATE UNIVERSITY, East Lansing, MI (US)

(72) Inventors: Christopher M. Saffron, Okemos, MI (US); Zhenglong Li, Lansing, MI (US); Dennis J. Miller, Okemos, MI (US); James E. Jackson, Haslett, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 287 days.

(21) Appl. No.: 14/383,048

(22) PCT Filed: Mar. 5, 2013

(86) PCT No.: PCT/US2013/029044
§ 371 (c)(1),
(2) Date: Sep. 4, 2014

(87) PCT Pub. No.: WO2013/134220
PCT Pub. Date: Sep. 12, 2013

(65) Prior Publication Data
US 2015/0008139 A1 Jan. 8, 2015

Related U.S. Application Data

(60) Provisional application No. 61/607,057, filed on Mar. 6, 2012.

(51) Int. Cl.
*C25B 3/00* (2021.01)
*C25B 3/01* (2021.01)
(Continued)

(52) U.S. Cl.
CPC .............. *C25B 3/00* (2013.01); *C07C 29/132* (2013.01); *C07C 29/20* (2013.01); *C07D 307/44* (2013.01);
(Continued)

(58) Field of Classification Search
CPC .... C25B 3/00; C25B 3/04; C25B 3/25; C25B 3/01; C25B 3/03; C25B 3/07
(Continued)

(56) References Cited

U.S. PATENT DOCUMENTS 4,886,591 A 12/1989 Lalancette et al.
5,225,581 A 7/1993 Pintauro
(Continued)

FOREIGN PATENT DOCUMENTS

EP 1 728 844 12/2006
JP 2004025022 A * 1/2004 .............. B01J 21/18
(Continued)

OTHER PUBLICATIONS

Dube et al., "Electrocatalytic Hydrogenation of Cyclohexanone: Simple Dynamic Cell Design," Journal of Applied Electrochemistry (no month, 2003), vol. 33, pp. 541-547.*
(Continued)

*Primary Examiner* — Edna Wong
(74) *Attorney, Agent, or Firm* — Marshall, Gerstein & Borun LLP

(57) ABSTRACT

A process and related electrode composition are disclosed for the electrocatalytic hydrogenation and/or hydrodeoxygenation of biomass-derived bio-oil components by the production of hydrogen atoms on a catalyst surface followed by the reaction of the hydrogen atoms with the organic compounds in bio-oil. The catalyst is a metal supported on a monolithic high surface area material such as activated carbon cloth. Electrocatalytic hydrogenation and/or hydro-
(Continued)

deoxygenation stabilizes the bio-oil under mild conditions to reduce coke formation and catalyst deactivation. The process converts oxygen-containing functionalities and unsaturated bonds into chemically reduced forms with an increased hydrogen content. The process is operated at mild conditions, which enables it to be a good means for stabilizing bio-oil to a form that can be stored and transported using metal containers and pipes.

33 Claims, 15 Drawing Sheets

(51) Int. Cl.
| | |
|---|---|
| C25B 3/03 | (2021.01) |
| C25B 3/07 | (2021.01) |
| C25B 3/25 | (2021.01) |
| C25B 11/043 | (2021.01) |
| C25B 11/051 | (2021.01) |
| C07C 29/132 | (2006.01) |
| C07C 29/20 | (2006.01) |
| C07D 307/44 | (2006.01) |

(52) U.S. Cl.
CPC ............. *C25B 3/25* (2021.01); *C25B 11/043* (2021.01); *C25B 11/051* (2021.01)

(58) Field of Classification Search
USPC ....... 205/413, 440, 446, 448, 450, 455, 456, 205/463
See application file for complete search history.

(56) References Cited

U.S. PATENT DOCUMENTS

| | | | |
|---|---|---|---|
| 5,919,349 A | * | 7/1999 | Huber ........................ C25B 3/04 204/292 |
| 6,218,556 B1 | | 4/2001 | Pintauro |
| 6,383,972 B1 | | 5/2002 | Parmentier et al. |
| 6,758,871 B2 | | 7/2004 | Finkelshtain et al. |
| 7,425,657 B1 | | 9/2008 | Elliott et al. |
| 7,695,534 B2 | | 4/2010 | Lawson et al. |
| 7,722,755 B2 | | 5/2010 | Lawson et al. |
| 2004/0016650 A1 | | 1/2004 | Klug |
| 2005/0262760 A1 | | 12/2005 | Lawson et al. |
| 2006/0247122 A1 | | 11/2006 | Hampden-Smith et al. |
| 2008/0047838 A1 | | 2/2008 | Van Erkel et al. |
| 2009/0068544 A1 | | 3/2009 | Ragsdale et al. |
| 2010/0297720 A1 | | 11/2010 | Medoff et al. |
| 2011/0042229 A1 | | 2/2011 | Fan |
| 2011/0245554 A1 | | 10/2011 | Huber et al. |
| 2011/0258914 A1 | | 10/2011 | Banasiak et al. |

FOREIGN PATENT DOCUMENTS

| | | |
|---|---|---|
| KR | 10-2008-0070988 | 8/2008 |
| WO | WO-2007/082092 | 7/2007 |
| WO | WO-2008/063322 | 5/2008 |
| WO | WO-2010/128505 | 11/2010 |
| WO | WO-2011/064172 | 6/2011 |

OTHER PUBLICATIONS

Ishikawa et al., "Electric Double-Layer Capacitor Composed of Activated Carbon Fiber Cloth Electrodes and Solid Polymer Electrolytes Containing Alkylammonium Salts," J. Electrochem. Soc. (Jul. 1994), vol. 141, No. 7, pp. 1730-1734.*
Gluckstein et al., "Final Report: Investigation of Catalytic Pathways for Lignin Breakdown into Monomers and Fuels," Oak Ridge National Laboratory (Oct. 2010), 44 pp.*

Samolada et al., "Catalyst Evaluation for Catalytic Biomass Pyrolysis," Energy & Fuels (no month, 2000), vol. 14, pp. 1161-1167.*
Macias Perez et al., "Platinum Supported on Activated Carbon Cloths as Catalyst for Nitrobenzene Hydrogenation," Applied Catalysis A: General (no month, 1997), vol. 151, pp. 461-475.*
Seo et al., "Investigation on Removal of Hardness Ions by Capacitive Deionization (CDI) for Water Softening Applications," Water Research (no month, 2010), vol. 44, pp. 2267-2275.*
Miller et al., "Electrocatalytic Hydrogenation of Aromatic Compounds," J. Org. Chem. (1978), vol. 43, No. 10, pp. 2059-2061. (Year: 1978).*
Seo et al., "Investigation on Removal of Hardness Ions by Capacitive Deionization (CDI) for Water Softening Applications," Water Research (2010), vol. 44, pp. 2267-2275. (Year: 2010).*
Ishikawa et al., "Electric Double-Layer Capacitor Composed of Activated Carbon Fiber Cloth Electrodes and Solid Polymer Electrolytes Containing Alkylammonium Salts," J. Electrochem. Soc. (Jul. 1994), vol. 141, No. 7, pp. 1730-1734. (Year: 1994).*
Samolada et al., "Catalyst Evaluation for Catalytic Biomass Pyrolysis," Energy & Fuels (2000), vol. 14, pp. 1161-1167. (Year: 2000).*
Martel et al., "Electrocatalytic Hydrogenation of Phenol on Various Electrode Materials," Canadian Journal of Chemistry (Dec. 1, 1997), vol. 75, No. 12, pp. 1862-1867. (Year: 1997).*
Cyr et al., "Electrocatalytic Hydrogenation of Lignin Models at Raney Nickel and Palladium-Based Electrodes," Canadian Journal of Chemistry (Mar. 1, 2000), vol. 78, No. 3, pp. 307-315. (Year: 2000).*
Amouzegar et al., "Electrocatalytic Hydrogenation of Phenol on Dispersed Pt: Effect of Metal Electrochemically Active Surface Area and Electrode Material," Journal of Applied Electrochemistry (1997), vol. 27, pp. 539-542. (Year: 1997).*
Gluckstein et al., "Final Report: Investigation of Catalytic Pathways for Lignin Breakdown into Monomers and Fuels," Oak Ridge National Laboratory (Oct. 2010), 44 pp. (Year: 2010).*
Cyr et al., "Electrocatalytic Hydrogenation of Lignin Models at Raney Nickel and Palladium-Based Electrodes," (Mar. 1, 2000), vol. 78, No. 3, pp. 307-315). (Year: 2000).*
Auer et al., "Carbons as Supports for Industrial Precious Metal Catalysts," Applied Catalysis A: General (Oct. 25, 1998), vol. 173, No. 2, pp. 259-271. (Year: 1998).*
Santana et al., "Electrocatalytic Hydrogenation of Organic Compounds Using Current Density Gradient and Sacrificial Anode of Nickel," Tetrahedron Letters (Jun. 16, 2003), vol. 44, No. 25, pp. 4725-4727. (Year: 2003).*
Amouzegar et al., "Electrocatalytic Hydrogenation of Phenol on Highly Dispersed Pt Electrodes," Electrochimica Acta (1994), vol. 39, No. 4, pp. 557-559. (Year: 1994).*
Macias Perez et al., "Platinum Supported on Activated Carbon Cloths as Catalyst for Nitrobenzene Hydrogenation," Applied Catalysis A: General (1997), vol. 151, pp. 461-475. (Year: 1997).*
Mullen et al., "Chemical Composition of Bio-Oils Produced by Fast Pyrolysis of Two Energy Crops," Energy & Fuels (May 21, 2008), vol. 22, No. 3, pp. 2104-2109. (Year: 2008).*
Du et al., "Comparison of Catalytic Activity for Liquid Hydrogenation of Different Substitution Benzenes Over Ru—Pd/AC," Xinan Minzu Daxue Xuebao, Ziran Kexueban (2004), vol. 30, No. 3, pp. 291-294. (Year: 2004).*
Andrieux C. P., Farriol M., Gallardo I., and Marquet J., "Thermodynamics and Kinetics of Homolytic Cleavage of Carbon-Oxygen Bonds in Radical Anions Obtained by Electrochemical Reduction of Alkyl Aryl Ethers," *J. Chem. Soc., Perkin Trans. 2*, 985-90 (2002).
Campelo J, Luna D., Luque R., Marinas, J. M., and Romero A. A., "Sustainable Preparation of Supported Metal Nanoparticles and Their Applications in Catalysis," *ChemSusChem*, pp. 1-28 (2009).
Elliott D. C., and Hart T. R., "Catalytic Hydroprocessing of Chemical Models for Bio-Oil," *Energy & Fuels*, 23:631-37 (2009) (Published on Web Dec. 12, 2008).
Garedew M., Li Z., Lam C. H., Erickson N., Sousa L., Jackson J. E., and Saffron C. M., "Lignin Model Compound Upgrading via Electrocatalytic Hydrogenation and Deoxygenation," 1 page, (presented Sep. 2013).
Gluckstein J., Hu M., Kidder M., McFarlane J., Narula C., and Sturgeon M., "Final Report: Investigation of Catalytic Pathways for

(56) References Cited

OTHER PUBLICATIONS

Lignin Breakdown into Monomers and Fuels," Report No. ORNL/TM-2010/281, 44 pages (Oct. 2010).
Hou T., Yuan L., Ye T., Gong L., Tu J., Yamamoto M., Torimoto Y., and Li Q., "Hydrogen Production by Low-Temperature Reforming of Organic Compounds in Bio-Oil over a CNT-Promoting Ni Catalyst,", *Int. J. Hydrogen Energy*, 34:9095-9107 (2009).
Huber G. W., and Corma A., "Synergies Between Bio- and Oil Refineries for the Production of Fuels from Biomass," *Angew. Chem. Int. Ed.*, 46:7184-7201 (2007).
Li Z, Kelkar S., Lam C. H., Luczek K., Jackson J. E., Miller D.J., and Saffron C. M., "Aqueous Electrocatalytic Hydrogenation of Furfural Using a Sacrificial Anode," *Electrochimica Acta*, 64:87-93 (2012) (Available online Dec. 31, 2011).
Li Z., Garedew M., Lam C. H, Jackson J. E., Miller D. J., and Saffron C. M., "Mild Electrocatalytic Hydrogenation and Hydrodeoxygenation of Bio-Oil Derived Phenolic Compounds Using Ruthenium Supported on Activated Carbon Cloth," *Green Chem.*, 14:2540-49 (2012) (Published online Jun. 27, 2012).
Pariente S., Tanchoux N., Fajula F., Centi G., and Perathoner S., "Bioethanol: Production and Pathways for Upgrading and Valorization," in *Catalysis for Renewables: From Feedstock to Energy Production*, Edited by Gabriele Centi and Rutger A. van Santen, Wiley-VCH Verlag GmbH & Co. KGaA, Weinheim, ISBN: 978-3-527-317882-2 (Copyright © 2007).
Resasco D. E., and Crossley S., "Molecular Engineering Approach in the Selection of Catalytic Strategies for Upgrading of Biofuels," *AIChE Journal*, 55(5):1082-1089 (May 2009).
Rodriguez E., Garedew M., and Saffron C. M., "Electrocatalytic Hydrogenation of Lignin Model Compounds Using Ruthenium Loaded on Activated Carbon Cloth," 1 page, (presented Summer, 2013).
Srinivasan R., and Sorial G. A., "Adsorption of Geosmin and MIB on Activated Carbon Fibers—Single and Binary Solute System," *Water Air Soil Pollut: Focus*, 9:223-235 (2009).
Vispute T. P., "Pyrolysis Oils: Characterization, Stability Analysis, and Catalytic Upgrading to Fuels and Chemicals," A Ph.D. dissertation, (Feb. 1, 2011).
Vitolo S., and Ghetti P., "Physical and Combustion Characterization of Pyrolytic Oils Derived from Biomass Material Upgraded by Catalytic Hydrogenation," 3 pages (1994).
Zhao C., Kou Y., Lemonidou A. A., Li X., and Lercher J. A., "Highly Selective Catalytic Conversion of Phenolic Bio-Oil to Alkanes," *Angew. Chem.*, 121:4047-50 (2009).
International Search Report in PCT/US2013/029044, dated May 22, 2013 (2 pages).
Amouzegar et al., Electrocatalytic hydrogenation of phenol on dispersed Pt: Effect of metal electrochemically active surface area and electrode material, Journal of applied electrochemistry, 27 (1997) 539-542.
Amouzegar et al., Electrocatalytic hydrogenation of phenol on highly dispersed Pt electrodes, Electrochimica Acta 39 (1994) 557-559.
Arena, Deactivation of ruthenium catalysts in continuous glucose hydrogenation, Applied Catalysis A: General, 87 (1992) 219-229.
Aumo et al., Hydrogenation of citral over activated carbon cloth catalyst, Ind. Eng. Chem. Res., 44 (2005) 5285-5290.
Besson et al., Active carbons as catalysts for liquid phase reactions, Catalysis Today 102 (2005) 160-165.
Brisach-Wittmeyer et al., Electrocatalytic hydrogenation of catechol on Rh-Al2O3 in different media—pH-Dependent reduction mechanism for intermediate formation, Can J. Chem., 84 (2006) 1640-1647 [abstract only].
Busetto et al., Application of the Shvo catalyst in homogeneous hydrogenation of bio-oil obtained from pyrolysis of white poplar: new mild upgrading conditions, Fuel, 90 (2010) 1197-1207.
Chamoulaud et al., Biomass conversion II: simultaneous electrosynthesis of furoic acid and furfuryl alcohol on modified graphite felt electrodes, Electrochim. Acta 46 (2001) 2757-60.

Chu et al., Nano TiO2 film electrode for electrocatalytic reduction of furfural in ionic liquids, J. Nanoparticles Res. 11 (2009) 1805-9.
Cirtiu et al., Electrocatalysis over Pd catalysts: A very efficient alternative to catalytic hydrogenation of cyclohexanone, J. Catal., 245 (2007) 191-7.
Cirtiu et al., Modification of the surface adsorption properties of alumina-supported Pd catalysts for the electrocatalytic hydrogenation of phenol, Langmuir, 22:6414-21 (2006).
Cyr et al., Electrocatalytic hydrogenation of lignin models at Raney nickel and palladium-based electrodes, Canadian Journal of Chemistry, 78 (2000) 307-315 [abstract only].
Czernik et al., Overview of applications of biomass fast pyrolysis oil, Energy & Fuels 18 (2004) 590-598.
Da Silva et al., Homogeneous electro-mediated reduction of unsaturated compounds using Ni and Fe as mediators in DMF, Tetrahedron 62 (2006) 5435-40.
Dabo et al., Canadian journal of chemistry 77 (1999) 1225-1229 [abstract only].
Dalavoy et al., Mild electrocatalytic hydrogenation of lactic acid to lactaldehyde and propylene glycol, Journal of Catalysis 246 (2007) 15-28.
Diaz et al., Hydrogenation of phenol in aqueous phase with palladium on activated carbon catalysts, Chemical Engineering Journal 131 (2007) 65-71.
Ebert, Furfural: Future Feedstock for Fuels and Chemicals, Biomass Magazine, downloaded from the Internet at: <http://biomassmagazine.com/articles/1950/furfural-future-feedstock-for-fuels-and-chemicals> (2008).
Gouli et al., Effects of some oxygenated substitutes on gasoline properties, spark ignition engine performance, and emissions, Energy & Fuels, 12 (1998) 918-24.
Gutierrez et al., Hydrodeoxygenation of guaiacol on noble metal catalysts, Catalysis Today 147 (2009) 239-246.
Ilikti et al., Electrocatalytic hydrogenation of alkyl-substituted phenols in aqueous solutions at a Raney nickel electrode in the presence of a non-micelle-forming cationic surfactant, Journal of applied electrochemistry 34 (2004) 127-136.
Ilikti et al., Electrocatalytic hydrogenation of phenol in aqueous solutions at a Raney nickel electrode in the presence of cationic surfactants, Journal of applied electrochemistry, 32 (2002) 603-609.
Kulkarni et al., Theoretical Evaluation and Experimental Validation of Performance Parameters of New Hypergolic Liquid Fuel Blends with Red Fuming Nitric Acid as Oxidizer, Propell. Explos. Pyrot. 34 (2009) 520 [abstract only].
Laplante et al., Considerations about phenol electrohydrogenation on electrodes made with reticulated vitreous carbon cathode, Can. J. Chem., 81 (2003) 258-264 [abstract only].
Lessard et al., High yield conversion of residual pentoses into furfural via zeolite catalysis and catalytic hydrogenation of furfural to 2-methylfuran, Top. Catal. 53 (2010) 1231-4.
Lima et al., A factorial design analysis of (+)-pulegone electrocatalytic hydrogenation, J. Electroanal. Chem. 613 (2008) 58-66.
Lin et al., Catalytic hydrodeoxygenation of guaiacol on Rh-based and sulfided CoMo and NiMo catalysts, Energy & Fuels 25 (2011) 890-896.
Mahdavi et al., Electrocatalytic hydrogenation of conjugated enones on nickel boride, nickel, and Raney nickel electrodes, Canadian Journal of Chemistry-Revue Canadienne De Chimie 73 (1995) 846-852 [abstract only].
Mahdavi et al., The electrocatalytic hydrogenation of phenanthrene at raney nickel electrodes: the effect of periodic current control, Electrochim. Acta, 38 (1993) 1377-80.
Mahfud et al., Hydrogenation of fast pyrolyis oil and model compounds in a two-phase aqueous organic system using homogeneous ruthenium catalysts, Journal of Molecular Catalysis A: Chemical 264 (2007) 227-236.
Mahfud et al., The application of water-soluble ruthenium catalysts for the hydrogenation of the dichloromethane soluble fraction of fast pyrolysis oil and related model compounds in a two phase aqueous-organic system, Journal of Molecular Catalysis A: Chemical 277 (2007) 127-136.
Moens et al., Study of the neutralization and stabilization of a mixed hardwood bio-oil, Energy & Fuels 23 (2009) 2695-2699.

(56) References Cited

OTHER PUBLICATIONS

Navarro et al., Catalytic hydrogenation of organic compounds with H2 supply: An electrochemical system, J. Chem. Educ. 81 (2004) 1350-2.
Nurunnabi et al., Effects of Ruthenium Precursors on Ru/Mn/Al2O3 and Ru/Al2O3 Catalysts for Fischer-Tropsch Synthesis, Journal of the Japan Petroleum Institute 53 (2010) 75-82.
Oasmaa et al., Fast Pyrolysis of forestry residue. 3. Storage stability of liquid fuel, Energy & Fuels, 17 (2003) 1075-1084.
Parpot et al., Electrochemical investigations of the oxidation-reduction of furfural in aqueous medium application to electrosynthesis, Electrochim. Acta 49 (2004) 397-403.
Perrard et al., Highly efficient metal catalysts supported on activated carbon cloths: A catalytic application for the hydrogenation of D-glucose to D-sorbitol, Applied Catalysis A: General, 331 (2007) 100-104.
Pimparkar et al., Hydrogenation of amino acid mixtures to amino alcohols, Ind. Eng. Chem. Res., 47 (2008) 7648-7653.
Pradhan et al., Effect of different oxidizing agent treatments on the surface properties of activated carbons, Carbon 37 (1999) 1323-1332.
Ragnar et al., pK(a)-values of guaiacyl and syringyl phenols related to lignin, Journal of wood chemistry and technology, 20 (2000) 277-305.
Rangel-Mendez et al., Adsorption of cadmium by activated carbon cloth: influence of surface oxidation and solution pH, Water Research 36 (2002) 1244-1252.
Rao et al., Furfural hydrogenation over carbon-supported copper, Catal. Lett. 60 (1999) 51-57.
Robin et al., The electrocatalytic hydrogenation of fused polycyclic aromatic comopunds at Raney nickel electrodes: the influence of catalyst activation and electrolysis conditions, Can. J. Chem. 68 (1990) 1218-27.
Roessler et al., Electrocatalytic Hydrogenation of Indigo: Process Optimization and Scale-Up in a Flow Cell, Journal of the Electrochemical Society 150 (2003) D1-D5.
Santana et al., Electrocatalytic hydrogenation of organic compounds using a nickel sacrificial anode, J. Electroanal. Chem., 569 (2004) 71-8.
Scholze etal., Characterization of the water-insoluble fraction from pyrolysis oil (pyrolytic lignin). Part I. PY-GC/MS, FTIR, and functional groups, Journal of Analytical and Applied Pyrolysis 60 (2001) 41-54.
Sluiter et al., Templeton in Determination of Ash in Biomass, National Renewable Energy Laboratory, Golden, Colorado, Jul. 17, 2005, pp. 1-5.
Solladie-Cavallo et al., Heterogeneous hydrogenation of substituted phenols over $Al_2O_3$ supported ruthenium, Journal of Molecular Catalysis A: Chemical 273 (2007) 92-98.
Taherzadeh et al., Inhibition effects of furfural on aerobic batch cultivation of *Saccharomyces cerevisiae* growing on ethanol and/or acetic acid, J. Biosci. Bioeng., 90(4):374-80 (2000).
Tountian et al., Effect of support conductivity of catalytic powder on electrocatalytic hydrogenation of phenol, J. Appl. Electrochem., 39 (2009) 411-9.
Van der Vaart, Electrocatalytic Hydrocracking, Virginia Polytechnic Institute and State University, Blacksburg, 1992, 50 pp.
Venderbosch et al., Stabilization of biomass-derived pyrolysis oils, Journal of Chemical Technology & Biotechnology, 85 (2010) 674-686.
Vilar et al., Investigation of the hydrogenation reactivity of some organic substrates using an electrocatalytic method, Appl. Catal. A: Gen., 372 (2010) 1-7.
Vispute et al., Production of hydrogen, alkanes and polyols by aqueous phase processing of wood-derived pyrolysis oils, Green Chemistry, 11 (2009) 1433-1445.
Wildschut et al., Catalyst studies on the hydrotreatment of fast pyrolysis oil, Applied Catalysis B: Environmental 99 (2010) 298-306.
Wildschut et al., Hydrotreatment of fast pyrolysis oil using heterogeneous noble-metal catalysts, Ind. Eng. Chem. Res., 48 (2009) 10324-10334.
Yang et al.,, Effects of calcination temperature on performance of Cu—Zn-Al catalyst for synthesizing upsilon-butyrolactone and 2-methylfuran through the coupling of dehydrogenation and hydrogenation, Catal. Commun. 5 (2004) 505-10.
Zhang et al., Aqueous-phase hydrogenation of lactic acid to propylene glycol, Applied Catalysis A: General 219 (2001) 89-98.
Zhao et al., Aqueous-phase hydrodeoxygenation of bio-derived phenols to cycloalkanes, Journal of Catalysis 280 (2011) 8-16.
Zheng et al., Towards understanding the reaction pathway in vapour phase hydrogenation of furfural to 2-methylfuran, J. Mol. Catal. A: Chem., 246 (2006) 18-23.
Zhu et al., A new strategy for the efficient synthesis of 2-methylfuran and upsilon-butyrolactone, New J. Chem., 27 (2003) 208-10.

\* cited by examiner

ELECTROCATALYTIC HYDROGENATION AND HYDRODEOXYGENATION OF OXYGENATED AND UNSATURATED ORGANIC COMPOUNDS

CROSS REFERENCE TO RELATED APPLICATION

Priority is claimed to U.S. Provisional Application No. 61/607,057 (filed on Mar. 6, 2012), which is incorporated herein by reference in its entirety.

STATEMENT OF GOVERNMENT INTEREST

None.

BACKGROUND OF THE DISCLOSURE

Field of the Disclosure

The disclosure generally relates to a process for the electrocatalytic hydrogenation and/or hydrodeoxygenation of biomass-derived bio-oil by the production of hydrogen atoms on a catalyst surface followed by the reaction of the hydrogen atoms with the organic compounds in bio-oil, wherein the catalyst is a metal supported on a monolithic high surface area material such as activated carbon cloth.

Brief Description of Related Technology

Biomass pyrolysis derived bio-oil is a mixture containing hundreds of organic compounds with chemical functionalities that are corrosive to container materials and are prone to polymerization. After aging during storage or transit, the properties of bio-oil change which renders the mixture incompatible with the existing U.S. energy infrastructure. Stabilization and upgrading of the bio-oil into a more stable (e.g., less reactive) form is required.

Currently, upgrading and stabilization of bio-oil has been investigated using different catalysis methods, including one-step hydrotreatment, two-stage or multistage hydrotreatment, catalytic cracking and homogeneous catalytic upgrading.

One-step hydrotreatment upgrading of bio-oil usually employs standard Ni—Mo or Co—Mo catalysts under a $H_2$ atmosphere. This approach typically needs high temperature (200-400° C.) and high pressure (100-200 bar) to obtain high production rates. Bio-oil is not stable in such a harsh environment, so tar and coke are usually produced. Tar can easily plug the reactor and coke will deactivate the catalyst very quickly. A large amount of hydrogen is required by this process.

Two-stage or multistage upgrading processes include a low temperature hydrogenation step and one or more high temperature hydrodeoxygenation steps. The first step takes place at a temperature range from 125° C. to 250° C. and a pressure larger than 50 bar with precious metal catalysts. The hydrodeoxygenation steps are mainly used to reduce the oxygen content and raise hydrogen content of phenolics, while cracking larger molecules under higher temperature (above 300° C.). Molecular hydrogen is required as a source of reducing equivalents during all steps. As bio-oil polymerization starts to accelerate at 80° C., the condition used for this method still causes substantial coke formation.

In the technology of the catalytic cracking, bio-oils are upgraded at atmospheric pressure and high temperature with acidic catalysts (HZSM-5, $Al_2O_3$, Al-MCM-41, etc.). This method has some disadvantages, such as a high coking rate (8-25 wt %) and poor resultant fuel quality.

Homogeneous catalytic upgrading of bio-oil is carried out at mild temperature, around 90° C., but still requires high pressure. Furthermore, molecular hydrogen is also needed as the reducing agent. The catalyst, often an expensive precious metal complex dissolved in the solution, requires further separation from the final products, resulting in high separation costs.

SUMMARY

The present disclosure relates to electrocatalytic hydrogenation and/or hydrodeoxygenation, which can stabilize bio-oil at low temperature and pressure (e.g., less than 100° C., even room temperature, and ambient pressure). Lower temperature results in reduced coke encapsulation of the embedded catalyst, and hence, reduced catalyst deactivation. The use of mild operating conditions also avoids bio-oil decomposition into small molecules and thus retains more carbon in the final liquid products. Furthermore, the availability of bulk molecular hydrogen is limited to existing petroleum refineries and is not often regionally available. Electrocatalysis only requires access to local power grids to supply the electricity needed to promote chemical reduction. The electricity can be generated from alternative renewable sources, such as solar, wind, hydro, etc., which makes electrocatalytic upgrading of a bio-oil feedstock more sustainable.

The woven or knitted fiber form of the ACC material is convenient as a bulk monolithic catalyst material that has both high electrical conductivity and favorable surface area properties for direct use as a support for a catalytic electrode. While similar to particulate activated carbon material in terms of microstructure and chemical properties, the bulk monolithic property (e.g., as a woven material) of the ACC provides a monolithic material with a high electrical conductivity making it suitable for electrocatalytic reactions. Specifically, the high electrical conductivity permits electrode currents that are high enough to generate suitable levels of hydrogen atoms (H.) to promote substantial levels of reactant conversion. The high electrical conductivity/low electrical resistivity of the ACC material, even after metal particle deposition, also limits heat dissipation/generation at the desired electrode currents (e.g., meaning that low-temperature, (substantially) isothermal reaction environments can be maintained with little or no required heat removal). The flexibility of the ACC material allows it to be configured into any convenient electrode shape to accommodate a given reaction system/reactor geometry.

In one aspect, the disclosure relates to a catalytic electrode composition comprising: (a) a porous activated carbon cloth (ACC) support; and (b) metal catalyst particles immobilized on the ACC support. Suitably, the catalytic electrode is capable of catalyzing at least one of electrocatalytic hydrogenation (ECH) and electrocatalytic hydrodeoxygenation (ECHDO). For example, the catalytic electrode can be capable of catalyzing at least one of (i) ECH of unsaturated carbon-carbon bonds in an organic substrate, (ii) ECH of carbon-oxygen double bonds in an organic substrate, and (iii) ECHDO of carbon-oxygen single bonds in an organic substrate. The organic substrate (e.g., a hydrocarbon material; having at least 1, 2, or 3 carbon atoms and/or up to 6, 8, or 10 carbon atoms in various embodiments) can include one or more heteroatoms (e.g., N, O, S) in addition to any oxygen atoms subject to ECH/ECHDO. In an embodiment, the (catalytic) reduction reaction is heterogeneously catalyzed between the organic substrate adsorbed on the ACC support and atomic hydrogen adsorbed on the electrocatalytic metal particles of the electrode.

Various refinements and extensions of the catalytic electrode composition are possible.

For example, the metal forming the immobilized catalyst particles can be selected from the group consisting of Ru, Ni, Fe, Cu, Pt, Pd, Rh, Ir, Re, Os, Ag, Au, Co, Mo, Ga, mixtures thereof, alloys thereof, and combinations thereof. The metal particles can comprise nanoparticles having a size of at least 1 nm, 2 nm, 5 nm, 10 nm, or 20 nm, and/or up to 20 nm, 50 nm, 100 nm, or 200 nm, for example where a given size or size range can define boundaries of a size distribution or a mean of a size distribution such as a number-, volume-, or weight-average size. Suitably, the metal particles have metal dispersions of at least 1% and/or up to 90% (i.e., where the dispersion value represents the fraction of metal atoms immobilized on the support that are exposed to the external environment and thus provide an exposed, catalytically active surface).

In one refinement, the metal particles can be immobilized on the ACC support by performing an incipient wetness impregnation process. Such a process typically includes: (i) soaking the ACC support in a solution of metal precursors such as metal salts; (ii) drying the coated/impregnated support under ambient conditions, followed by vacuum drying at room temperature; and (iii) reducing the immobilized metals under flowing $H_2$.

In another refinement, the metal particles can be immobilized on the ACC support by performing an ion exchange process. Such a process typically includes: (i) oxidizing the ACC support to increase its oxygenated functionalities; (ii) washing the oxidized support thoroughly with deionized (DI) water to remove oxidant residues; (iii) drying under vacuum at room temperature; (iv) soaking the support in a metal precursor (e.g., metal salt) solution; (v) drying under vacuum at room temperature; and (vi) reducing the immobilized metals under flowing $H_2$. Suitably, the electrical resistance of the resulting electrode bulk material is not more than 2, 5, 10, 20, 50, or 100 times that of the original ACC support prior to metal particle immobilization.

The ACC support and the resulting catalytic electrode are generally in the flexible woven or knitted monolithic form. The favorable surface area properties of the ACC support make it suitable for direct use as a support for a catalytic electrode. For example, the ACC support prior to metal particle immobilization can have a microporous structure with a specific BET surface area of at least 800 $m^2/g$ or 1000 $m^2/g$ and/or up to 2500 $m^2/g$ or 3000 $m^2/g$. Alternatively or additionally, the ACC support prior to metal particle immobilization can have a microporous structure with a specific micropore surface area of at least 500 $m^2/g$ or 600 $m^2/g$ and/or up to 800 $m^2/g$, 1500 $m^2/g$, or 2100 $m^2/g$. Alternatively or additionally, the ACC support prior to metal particle immobilization can have a microporous structure with a specific micropore volume of at least 0.2 $cm^3/g$ or 0.3 $cm^3/g$ and/or up to 0.8 $cm^3/g$ or 1.0 $cm^3/g$. Similarly, the catalytic electrode can have a microporous structure with a specific BET surface area relative to that of the unmodified ACC support of at least 0.1, 0.2, or 0.4 and/or up to 0.4, 0.6, 0.8, or 0.9. In a refinement, the electrode has a microporous structure with a specific micropore surface area relative to that of the unmodified ACC support of at least 0.1, 0.2, or 0.4 and/or up to 0.4, 0.6, 0.8, or 0.9. In another refinement, the electrode has a microporous structure with a specific micropore volume relative to that of the unmodified ACC support of at least 0.1, 0.2, or 0.4 and/or up to 0.4, 0.6, 0.8, or 0.9.

In another aspect, the disclosure relates to a process for performing at least one of electrocatalytic hydrogenation (ECH) and electrocatalytic hydrodeoxygenation (ECHDO) of an organic substrate, the process comprising: (a) providing a reaction mixture comprising an organic reactant comprising one or more functional groups selected from the group consisting of carbonyl carbon-oxygen double bonds, aromatic double bonds, ethylenic carbon-carbon double bonds, acetylenic carbon-carbon triple bonds, hydroxyl carbon-oxygen single bonds, ether carbon-oxygen single bonds, and combinations thereof; (b) contacting the reaction mixture with a first electrode (e.g., a cathode) comprising the catalytic electrode composition according to any of the various disclosed embodiments; (c) electrically contacting the reaction mixture with a second electrode (e.g., an anode); (d) applying an electrical potential between the first electrode and the second electrode to provide an electrical current therebetween and through the reaction mixture, thereby performing at least one of an ECH reaction and an ECHDO reaction to reduce or deoxygenate at least one of the functional groups of the organic reactant and to form at least one of (i) an ECH reaction product thereof and (ii) an ECHDO reaction product thereof; and optionally (e) recovering or separating the reaction product from the reaction mixture. The ECH reaction and/or the ECHDO reaction can be heterogeneous reactions taking place (e.g., at least in part) at the first electrode (cathode). In an embodiment, second electrode comprises an electrically conductive material selected from the group consisting of Ni, Pt, carbon, lead, lead dioxide, mixtures thereof, alloys thereof, and combinations thereof (e.g., where the second electrode can be a dimensionally stable electrode or a sacrificial electrode). In a refinement, the process comprises performing the ECH and/or ECHDO reaction in an undivided electrochemical cell containing the reaction mixture, wherein the second electrode is in contact with the reaction mixture in the electrochemical cell. In another refinement, the process comprises performing the ECH and/or ECHDO reaction in a divided electrochemical cell containing the reaction mixture, wherein the second electrode is in contact with an anolyte mixture in electrical connection with the reaction medium via an ion-exchange membrane. In a further refinement, (i) the reaction mixture further comprises carboxylic acids, and (ii) the process further comprises removing at least some of the carboxylic acids from the reaction mixture into the anolyte mixture via the ion-exchange membrane.

Various refinements and extensions of the foregoing ECH and ECHDO processes are possible.

For example, the carbonyl carbon-oxygen double bonds subject to ECH/ECHDO can be present in a functional group selected from the group consisting of ketone groups, aldehyde groups, carboxylic acid groups, ester groups, amide groups, enone groups, acyl halide groups, acid anhydride groups, and combinations thereof. The aromatic double bonds subject to ECH/ECHDO can be carbon-carbon aromatic double bonds or carbon-heteroatom double bonds (e.g., such as C with N, O, or S in a heteroaromatic functional group). Such aromatic double bonds can be present in a functional group selected from the group consisting of benzenes, phenols, furans, pyridines, pyrazines, imidazoles, pyrazoles, oxazoles, thiophenes, naphthalenes, higher fused aromatics (e.g., with three or more fused aromatic rings), and combinations thereof. In such cases, the functional group can be the compound itself (such as phenol being reduced to cyclohexanone) or a substituted derivative of the compound (such as guaiacol being reduced to phenol).

As an example of a specific functional group amenable to electrocatalytic treatment, the functional group can comprise a C=O group, and the corresponding ECH reaction product can comprise at least one of a CH—OH (or C—OH) group and a $CH_2$ group (e.g., for ECH followed by ECHDO of intermediate hydroxy group). In another embodiment, the functional group can comprise an aromatic CH group, and the corresponding ECH reaction product can comprise a $CH_2$ group (e.g., in a reduced cyclic reaction product). In another embodiment, the functional group can comprise an ethylenic C=C group, and the corresponding ECH reaction product can comprise a CH—CH group. In another embodiment, the functional group can comprise a C—OH group, and the corresponding ECHDO reaction product can comprise a CH group (e.g., a deoxygenated alcohol/hydroxyl group). In another embodiment, the functional group can comprise a (C=O)O group, and the corresponding ECHDO reaction product can comprise at least one of a (C=O)H group and a $CH_2$—OH (or C—OH) group (e.g., a carboxylate group (such as in a carboxylic acid) which is deoxygenated or reduced to form a corresponding aldehyde and/or alcohol; such as may take place at reaction temperatures above about 70° C.). In another embodiment, the functional group can comprise an ether $R_1$—O—$R_2$ group, and the corresponding ECH or ECHDO reaction products can comprise one or more of a $R_1H$, $R_2OH$, $R_1OH$, and $R_2H$, where $R_1$ and $R_2$ are substituents containing from 1 to 10 carbon atoms (e.g., $R_1$ and $R_2$ can be organic or hydrocarbon substituents having at least 1, 2, or 3 carbon atoms and/or up to 6, 8, or 10 carbon atoms, which can include one or more heteroatoms (e.g., N, O, S) as well as the various carbonyl (ketone, aldehyde, ester, etc.), hydroxyl, aromatic, ethylenic groups mentioned above).

The reaction mixture can include components in addition to the organic reactant.

For example, the reaction mixture can further comprise a solvent system for the organic reactant (e.g., where the solvent(s) in the system additionally can be selected for their ability to solvate the reaction product(s) as well) and/or an electrolyte. In an embodiment, the solvent system comprises water and one or more water-miscible organic solvents to provide an aqueous medium as the reaction mixture. In a refinement, no molecular hydrogen is provided to the reaction mixture initially and/or during the ECH/ECHDO reaction(s). In another refinement, the initial reaction mixture can comprise a plurality of different organic reactants each comprising one or more of the functional groups subject to ECH/ECHDO, and the final reaction mixture can comprise a plurality of corresponding ECH reaction products and/or ECHDO reaction products. For example, the initial organic reactants can have at least 1, 2, or 3 carbon atoms and/or up to 6, 8, or 10 carbon atoms and the reaction products can have at least 1, 2, or 3 carbon atoms and/or up to 6, 8, or 10 carbon atoms. In a refinement, the plurality of the organic reactants and the reaction products each can be characterized as having distribution of sizes in terms of an average number of carbon atoms, and the average number of carbon atoms in the reaction product distribution (e.g., $<n_P>$ as a weight or mole/number average of carbon atoms across all product species) relative to the average number of carbon atoms of the organic reactant distribution (e.g., $<n_R>$ as a weight or mole/number average of carbon atoms across all reactant species) can have a difference of 2, 1, 0.5, or 0.2 carbon atoms (e.g., $|<n_R>-<n_P>|$ or $(<n_R>-<n_P>)$ is not more than 2, 1, 0.5, or 0.2). This represents the ability of the ECH/ECHDO process to reduce/deoxygenate a plurality of organic components without substantially reducing the average carbon number of the components by decomposing the original constituents into smaller molecules.

In a particular refinement, the reaction mixture can comprise a plurality of the organic reactants, where the plurality is selected from the group consisting of a multicomponent bio-oil, a multicomponent bio-oil fraction, a plurality of bio-oil components, and combinations thereof. For example, the bio-oil can be a reaction product produced from fast pyrolysis of (lignocellulosic) biomass (e.g., where the resulting multicomponent bio-oil can be used as is, or a fraction/subset of its components can be selected for ECH/ECHDO treatment/reaction). In an embodiment, the pyrolytic process is performed in the same facility as the ECH/ECHDO treatment. In another embodiment, the bio-oil from the pyrolytic process is subjected to the ECH/ECHDO treatment within 1 hr, 2 hr, 4 hr, 8 hr, or 24 hr from formation of the bio-oil (for example to permit fractionation or other intermediate processing before ECH/ECHDO treatment). In one refinement, the reaction mixture is free from added solvents (e.g., the ECH/ECHDO treatment is performed on the bio-oil (or more generally other organic reactants) without solvents, such as where the organic reactant(s) is initially at least about 90%, 95%, 98%, or 99% by weight of the reaction mixture. In another refinement, the reaction mixture comprises one or more of water and a water-miscible organic solvent (e.g., methanol, ethanol, 1-propanol, 2-propanol, 1-butanol, tetrahydrofuran, and mixtures thereof). In an embodiment, the reaction mixture comprises water and the water is present in an amount of at least 10 wt. %, 12 wt. %, 15 wt. %, 20 wt. %, 25 wt. %, or 30 wt. % and/or up to 20 wt. %, 30 wt. %, 40 wt. %, 50 wt. %, 70 wt. %, 90 wt. %, or 95 wt. % relative to the reaction mixture (with similar concentrations being applicable for the organic reactants individually or collectively in the reaction mixture). In an embodiment, the reaction mixture comprises the multicomponent bio-oil fraction, the fraction having been obtained by extraction of bio-oil using a solvent such as one or more of water, methanol, ethanol, diethyl ether, ethyl acetate, dichloromethane, chloroform, toluene, and hexane (e.g., thus providing a water-soluble or other specific solvent-soluble bio-oil fraction, etc.). In another embodiment, the reaction mixture comprises a plurality of bio-oil pyrolysis products, for example two or more compounds selected from the group consisting of acetol, hydroxyacetaldehyde, glyoxal, formaldehyde, acetic acid, phenol, guaiacol, syringol, levoglucosan, furfural, glucose, xylose, substituted derivatives thereof, and combinations thereof. Similarly, the reaction product can comprise one or more of ethylene glycol, propylene glycol, cyclohexanol, furfuryl alcohol, and methanol.

The ECH/ECHDO can be performed under a variety of conditions. While the ECH/ECHDO reactions are suitably performed under mild/ambient conditions (e.g., 0° C. to 100° C. and 0.8 atm to 1.2 atm), the operating conditions can be extended to other temperature and/or pressure values). For example, the process can comprise performing the ECH or ECHDO reaction at a temperature of at least 0° C., 20° C., 25° C., 30° C., 50° C., or 70° C. and/or up to 30° C., 50° C., 70° C., 80° C., 90° C., 100° C., 150° C., 200° C., 250° C. or 300° C. Similarly, the process can comprise performing the ECH or ECHDO reaction at a pressure of at least 0.5 atm, 0.8 atm, or 1 atm and/or up to 1.2 atm, 1.5 atm, 2 atm, 5 atm, 10 atm, 20 atm, 40 atm, or 50 atm. Suitable reaction current densities can be at least 10 mA/dm$^2$, 50 mA/dm$^2$, 100 mA/dm$^2$, 200 mA/dm$^2$, or 500 mA/dm$^2$ and/or up to 100 mA/dm$^2$, 200 mA/dm$^2$, 500 mA/dm$^2$, 1000 mA/dm$^2$, 2000 mA/dm$^2$, 5000 mA/dm$^2$, or 10000 mA/dm$^2$. In an embodiment, the organic reactant(s) has/have a conversion of at least 0.8, 0.85, 0.9, or 0.95 (e.g., applied to one or more reactants individually or all reactants collectively). In another embodiment, the process exhibits high reactant carbon recovery, with the ECH or ECHDO reaction product containing at least 80%, 85%, or 90% and/or up to 90%, 95%, or 98% of the carbon initially contained in the reaction mixture. In an embodiment, the organic reactant has a concentration in the initial reaction mixture of at least 1 mM, 2 mM, 5 mM, 10 mM, 20 mM, 50 mM, or 100 mM and/or up to 50 mM, 100 mM, 200 mM, 500 mM, 1,000 mM, 5,000 mM or 10,000 mM. In an embodiment, the initial reaction mixture has a pH value of at least 1, 2, 3, 4, 5, or 6 and/or up to 5, 6, 7, 8, 9, 10, or 11. In various refinements, the ECH or ECHDO reaction can be performed as a batch or a continuous process.

In another aspect, the disclosure relates to a reaction apparatus/system comprising an electrochemical cell (e.g., divided or undivided cell), the electrochemical cell comprising a cathode and an anode in electrical communication with each other (e.g., via an intermediate power supply or other means for applying a voltage potential between the electrodes/supplying electrons to the cathode). The cathode comprises the ACC-supported catalytic electrode composition according to any of the variously disclosed embodiments. When the electrochemical cell contains an appropriate reaction mixture including one or more organic reactants and an electrolyte (e.g., an anolyte and a catholyte in a divided cell system) a completed circuit is formed with the anode and cathode being in electrical communication/contact via the reaction mixture/electrolyte.

Additional features of the disclosure may become apparent to those skilled in the art from a review of the following detailed description, taken in conjunction with the drawings, examples, and appended claims.

BRIEF DESCRIPTION OF THE DRAWINGS

For a more complete understanding of the disclosure, reference should be made to the following detailed description and accompanying drawings wherein.

Figure 1:
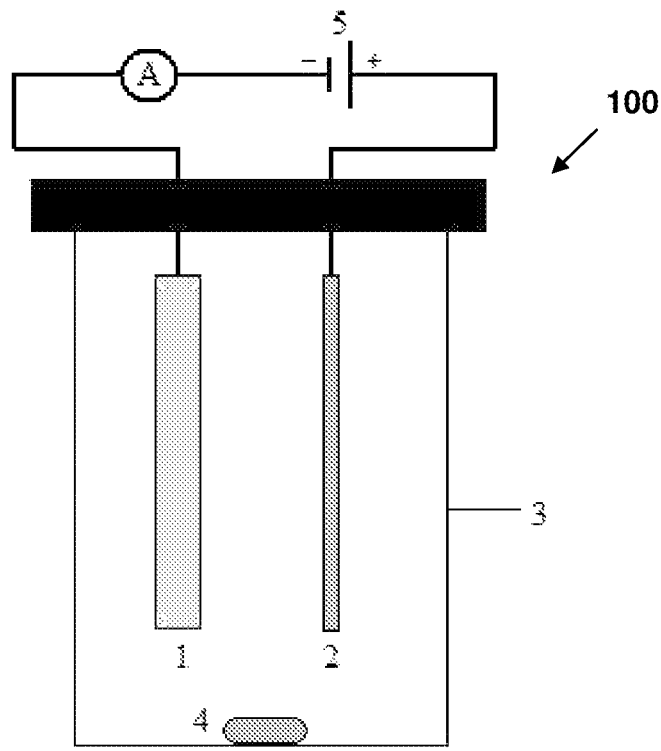
FIG. 1 illustrates an undivided electrochemical cell 100 composed of cathode 1 and anode 2 in the same electrochemical chamber 3. Bio-oil is added into the electrochemical chamber 3 for the electrocatalytic hydrogenation. Power supply 5 provides electrons to cathode 1 for the reduction reaction, while the anode 2 releases electrons to the power supply. Stirring is used to enhance mass transfer with a magnetic stirring bar 4. An ammeter is used to measure the current.

While the disclosed processes, compositions, and methods are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

The disclosure generally relates to a process and related catalytic compositions for the electrocatalytic hydrogenation (ECH) and/or hydrodeoxygenation (ECHDO) of biomass-derived bio-oil by the production of hydrogen atoms on a catalyst surface followed by the reaction of the hydrogen atoms with the organic compounds in bio-oil, wherein the catalyst is a metal supported on a monolithic high surface area material such as activated carbon cloth. Electrocatalytic hydrogenation and/or hydrodeoxygenation is disclosed herein to stabilize bio-oil under mild conditions to reduce the coke formation. Electrocatalytic hydrogenation and hydrodeoxygenation is used to convert oxygen containing functionalities and unsaturated carbon-carbon bonds into chemically reduced forms with an increased hydrogen content. It is operated at mild conditions, for example at lower than 100° C. and ambient pressure, which enables it to be a good means for stabilizing bio-oils to a form that can be stored and transported using metal containers and pipes. In particular, a catalyst including ruthenium or other metals supported on activated carbon cloth is employed as the cathode.

Before electrocatalytic hydrogenation and/or hydrodeoxygenation, bio-oil can be pretreated to increase its conductivity. Three different ways for bio-oil pretreatment include, but are not limited to, 1) electrolytes are added into the bio-oil directly; 2) bio-oil is dissolved in a solvent, such as mixture of methanol and water, and electrolytes are added into the bio-oil and solvent mixture; or 3) separation/extraction of bio-oil using water (or other solvent) is performed to form a water-soluble fraction and a water-insoluble fraction, and electrolytes are added into the water-soluble fraction to perform electrocatalytic hydrogenation (e.g., more general solvent-soluble and solvent-insoluble fractions).

The pretreated bio-oil is then stabilized in an electrochemical cell using electrocatalytic hydrogenation and/or hydrodeoxygenation. Electrocatalytic hydrogenation and/or hydrodeoxygenation of bio-oil can be performed at temperatures below 100° C. and ambient pressure. Elevated pressure can also be employed if desired. Electrocatalytic hydrogenation and/or hydrodeoxygenation is suitably performed at a current range from several mA to several A, and a voltage range from several V to hundreds of V.

Electrocatalytic hydrogenation and/or hydrodeoxygenation of bio-oil can be operated in two different electrochemical cells: an undivided electrochemical cell and a divided electrochemical cell.

An example of the undivided cell is shown in FIG. 1, where the cathode 1 and the anode 2 are in the same electrochemical chamber 3. To avoid oxidation of bio-oil compounds at the anode side, a sacrificial anode is used, such as sacrificial nickel, but not limited to nickel. Various materials can be used as the cathode, including aluminum, iron, zinc, copper, stainless steel, graphite, activated carbon cloth, but not limited to these materials. In another embodiment, the cathode can include the electrocatalytic electrode composition including catalytic metal particles deposited onto an activated carbon cloth substrate as described below. The pretreated bio-oil is used as the electrolysis solution.

Figure 2:
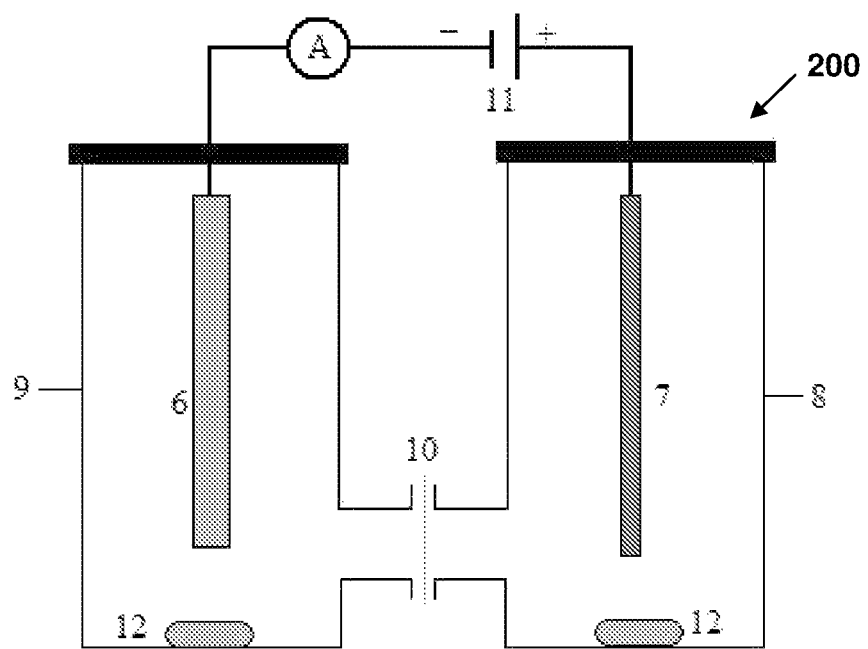
FIG. 2 illustrates a divided electrochemical cell 200 composed of cathode 6 and anode 7 in different electrochemical chambers (anode chamber 8 and cathode chamber 9) separated by an ion exchange membrane 10. Bio-oil is added into the cathode chamber 9 and aqueous solution with electrolytes is put into the anode chamber 8. Power supply 11 provides the electrons to the cathode 6. Magnetic stirring bar 12 is used to mix the solution to enhance mass transfer. An ammeter is used to measure the current.

An example of the divided cell is shown in FIG. 2. The anode chamber 8 and the cathode chamber 9 are separated by an ion exchange membrane 10. NAFION membranes, such as NAFION 115 and NAFION 117, are suitable (available from Dupont), but other membranes can be used as well. The cathode 6 in this divided cell is a metal dispersed onto activated carbon cloth using, for example, either of two methods: 1) incipient wetness impregnation or 2) a method employing cation exchange. The metals which can be used in the chemical hydrogenation can also be used to make the cathode catalyst, including nickel, iron, copper, ruthenium, platinum, palladium, rhodium, iridium, rhenium, silver, gold, but not limited to these metals. Ruthenium is illustrated in the examples below as a cathode catalyst due to its high hydrogenation activity and high stability. Several activated carbon cloths from different precursors can be used, such as pitch, rayon, polyacrylonitrile or phenolic resin, but not limited to these precursors. The anode can be made of bulk materials including platinum wire, platinum mesh, platinized titanium mesh, stainless steel wire, stainless steel mesh and graphite rod. Precious metals supported on high surface area material, such as platinum on activated carbon cloth, can also be used as an anode. The pretreated bio-oil is used as the cathode solution and aqueous solutions with different electrolytes can be used as the anode solution.

The activated carbon cloth (ACC) support and the resulting catalytic electrode are generally in a monolithic form of a flexible woven or knitted material. As noted above, the favorable morphological properties of the ACC (e.g., high surface area in terms of specific surface area, high porosity in terms of specific micropore volume, etc.) make it suitable for direct use as a support for a catalytic electrode (e.g., with the ACC material serving as a support/substrate for metal catalyst particles deposited thereon).

The ACC material can be formed from a carbon-containing fiber of desired diameter (e.g., 5 µm to 50 µm) such as a hydrocarbon-based polymeric fiber material. Examples of suitable polymeric fibers/precursors include pitch, rayon, polyacrylonitrile, and phenolic resin as non-limiting examples. The fiber material is then carbonized and physically or chemically activated/oxidized according to methods generally known in the art (e.g., for producing other forms of activated carbon such as powdered activated carbon, granular activated carbon, etc.). Suitable ACC material in both woven and knitted forms is commercially available from Calgon Carbon Co. (Pittsburgh, Pa.).

Biomass pyrolysis derived bio-oil (or pyrolysis oil) is a mixture containing hundreds of organic compounds with chemical functionalities that are corrosive to container materials and are prone to polymerization. Bio-oil is a condensed liquid oxygenated hydrocarbon product of the fast pyrolysis of biomass (e.g., agricultural biomass, forest biomass). Biomass pyrolysis includes heating to moderate temperatures (e.g., 450° C. to 650° C., without oxygen), and vapors formed during pyrolysis are condensed to provide a liquid bio-oil as a complex mixture of various compounds derived from the lignocellulosic precursors in the biomass. The specific composition of a particular bio-oil depends on its particular biomass feedstock, but representative components include water (e.g., 15-40 wt. %), pyrolitic lignin (e.g., 15-40 wt. %, including guaiacols, catechols, syringols, vanillins, etc.), carboxylic acids (e.g., 3-10 wt. % acetic acid, 2-8 wt. % formic acid), aldehydes and ketones (e.g., 5-15 wt. % glycolaldehyde; 2-8 wt. % acetol; 0.5-5 wt. % glyoxal; 1-6 wt. % formaldehyde, 2-8 wt. % acetaldehyde), and various carbohydrate pyrolysis derivatives (e.g., glucose, xylose, levoglucosan).

Bio-oil as obtained is generally a viscous, acidic brown oil (e.g., having a pH value of about 1-3). Suitable biomass sources for bio-oil formation include plants, trees (e.g., pine trees), agricultural crops, crop residues, grasses, forest and mill residues, wood and wood waste (e.g., saw dust), paper mill waste, and/or waste paper. Representative biomass constituents include cellulose, lignin, hemicellulose, fatty acids, and/or triglycerides, with particular components and amounts varying based on the source of the biomass. As described herein, bio-oil can be separated into a water-soluble fraction and a water-insoluble fraction by an aqueous extraction process for further processing by ECH/ECHDO of a subset of the original bio-oil constituents. Similarly, when a different solvent/extraction medium is used (e.g., non-aqueous solvent(s) alone or in combination with water as a solvent mixture), the bio-oil can be separated into a solvent-soluble fraction and a solvent-insoluble fraction for subsequent processing.

As noted, bio-oil as originally obtained from pyrolysis is a complex mixture of many different organic compounds having various chemical functionalities. Examples of specific reactant compounds include one or more of formaldehyde, acetaldehyde, glycolaldehyde, propanal, butanal, butanedial, acetone, 2,3-butanedione, formic acid, acetic acid, methyl acetate, propanoic acid, acetol, 1-hydroxy-2-butanone, furfural, furfuryl alcohol, 2-furanone, cyclopentanone, 3-methyl-2-cyclopentenone, 3-methyl-1,2-cyclopentanedione, levoglucosan, glucose, xylose, phenol, 2-methylphenol (cresols more generally), guaiacol, 4-ethylguaiacol, eugenol, isoeugenol, methoxyeugenol, syringol, and trimethoxybenzene (1,2,3- and other isomers). More generally, representative bio-oil constituents (or organic reactants from a different feedstock) can include linear, cyclic, or branched hydrocarbons and heteroatom-substituted hydrocarbons having at least 1, 2, or 3 carbon atoms and/or up to 6, 8, 10, 15, or 20 carbon atoms, for example having the various noted oxygen-containing and unsaturated/aromatic functional groups amenable to ECH/ECHDO according the disclosure. In some embodiments, higher molecular weight constituents may be present in the bio-oil, for example representing constituents from the original lignocellulosic biomass, incomplete pyrolysis products therefrom, and/or subsequent oligomerization/polymerization products from the low molecular weight pyrolysis bio-oil constituents.

Reaction products resulting from the ECH/ECHDO of bio-oil, fractions thereof, or components thereof generally correspond to the reduced/hydrogenated and/or deoxygenated forms of their respective reactants. Examples of specific product compounds include one or more of ethanol, 1-propanol, 2-propanol, 1-butanol, tetrahydrofurfuryl alcohol, cyclopentanol, cyclohexanol, ethylene glycol, propylene glycol, 1,2-butanediol, 1,4-butanediol, and sorbitol. More generally, representative ECH/ECHDO reaction products (from bio-oil constituents or organic reactants from a different feedstock) can include linear, cyclic, or branched hydrocarbons and heteroatom-substituted hydrocarbons having at least 1, 2, or 3 carbon atoms and/or up to 6, 8, 10, 15, or 20 carbon atoms, for example including linear, cyclic, or branched alcohols, diols, polyols, saturated alkanes, and saturated heteroatom-substituted alkanes.

The disclosed process is illustrated and described in the context of the electrocatalytic hydrogenation and/or hydrodeoxygenation of bio-oil and/or fractions thereof, but it is not limited to bio-oil. Other organic compounds with unsaturated and/or oxygen-containing carbon bonds or organic compound mixtures containing such functional groups can also be reduced or deoxygenated using the disclosed methods and compositions. For example, the disclosed processes can be applied more generally to single- or multi-component reactant/reaction mixtures including one or more organic reactants. The organic reactants can contain one or more functional groups such as carbonyl carbon-oxygen double bonds, aromatic double bonds, ethylenic carbon-carbon double bonds, acetylenic carbon-carbon triple bonds, hydroxylcarbon-oxygen single bonds, and/or ether carbon-oxygen single bonds (e.g., where such organic reactants/functional groups can represent bio-oil constituents or components of a different feedstock).

EXAMPLES

The following examples illustrate the disclosed processes and compositions, but are not intended to limit the scope of any claims thereto.

Fast pyrolysis converts biomass into a liquid fuel intermediate known as bio-oil. Due to oxygen-containing functional groups, bio-oil species are reactively unstable, corrosive, and have a high oxygen content, tending to polymerize during long term storage and upgrading. The high temperatures and pressures used for conventional stabilizing and upgrading of bio-oil lead to coke production and catalyst deactivation. Milder treatments are needed to reduce coke formation and increase catalyst lifetime while lowering costs.

A mild strategy for bio-oil upgrading uses electrocatalytic hydrogenation (ECH) and/or electrocatalytic hydrodeoxygenation (ECHDO). During ECH/ECHDO, atomic hydrogen generated in situ on the catalyst surface reacts with adsorbed organic compounds. The availability of such surface hydrogen is controlled by the applied current and potential at ambient pressure, rather than by external hydrogen pressure, as in the classical hydrogenation. Useful temperature lowering is known as well since most ECH/ECHDO reactions proceed below the boiling point of water. The examples demonstrate the ECH/ECHDO of furfural and guaiacol, two model compounds derived respectively from pyrolysis of cellulose and lignin, as well as ECH/ECHDO of bio-oil mixtures, including the water-soluble bio-oil components extractable from pyrolysis-converted biomass. The mild upgrading/stabilization process (e.g., at 25° C. to 80° C. or 100° C. and about 1 atm) is a safe, energy-saving path to fuel upgrading that reduces coke formation, catalyst deactivation, and carbon loss while providing a renewable energy (e.g., solar/wind)-to-hydrocarbon pathway for energy conversion (e.g., as a way to "store" solar/wind energy generated at variable rates due to environmental conditions).

Cost is a key issue for any intended biomass upgrading process. Screening of catalysts for ECH/ECHDO of furfural therefore focused on inexpensive metals: nickel, iron, aluminum, copper and stainless steel. With nickel catalyst at room temperature and ambient pressure, 78% of furfural underwent ECH/ECHDO to furfuryl alcohol along with small amounts of hydrogenolysis product 2-methylfuran (selectivities 95:5). Further trials revealed that acid favored formation of 2-methylfuran, raising its selectivity from 5% to 14% as pH was decreased from 5.0 to 1.0. Additional factors affecting the product selectivity, such as temperature and initial furfural concentration, were also investigated.

Unlike the reactive aldehyde furfural, the electron rich aromatic guaiacol (2-methoxyphenol) resisted ECH/ECHDO with simple nickel catalysts. However, development of a carbon-supported ruthenium electrocatalyst enabled complete conversion of guaiacol to cyclohexanol and 2-methoxycyclohexanol at 80° C. and ambient pressure. Effects of metal loading, electrolyte, temperature and substrate concentrations were explored. These examples with both model compounds and actual multi-component bio-oil fractions highlight the promise of ECH/ECHDO as a strategy for stabilizing and upgrading bio-oils from biomass fast pyrolysis across a variety of functional groups such as aldehydes, ketones, alcohols, phenolics, alkoxy groups, etc.

Example 1

Aqueous ECH of Furfural Using a Nickel Cathode

Furfural is a furan derivative that can serve as a building block for fuels and chemicals or as a liquid fuel itself. Interestingly, it is also known to be inhibitory in alcohol production by Saccharomyces cerevisiae. Reduction of furfural's aldehyde moiety forms primarily furfuryl alcohol and small amounts of 2-methylfuran, valuable intermediates in the perfumery, pharmaceutical and polymer industries. In particular, furfuryl alcohol has wide application in a variety of synthetic fibers, rubbers, thermostatic resins and farm chemicals. It can serve as a solvent for furan resins and pigments of low solubility and also as a component in rocket fuel. 2-Methylfuran is an intermediate in syntheses of crysanthemate pesticides, perfume intermediates and chloroquine lateral chains in medical polymers. It may serve as a fuel itself, or as an octane enhancer that reduces CO and volatile hydrocarbon emissions.

The main method for preparation of furfuryl alcohol and 2-methylfuran is vapor-phase catalytic hydrogenation (CH) of furfural. This approach requires high reaction temperatures (573-673 K) and pressurized hydrogen, a gaseous reagent not always available where furfural is produced. In this example, furfural reduction via electrocatalytic hydrogenation (ECH) was explored as a mild, efficient alternative to CH. This approach is usually performed at atmospheric pressure and temperatures below 100° C. with electricity as the reducing agent. The main difference between CH and ECH is the way to generate atomic hydrogen: the CH process requires externally supplied hydrogen gas and splits molecular hydrogen to atomic hydrogen (Eq. (1)), while ECH reduces hydronium ions to form atomic hydrogen in situ on the catalytic cathode surface using external electrons (Eq. (2)).

$$H_2 + 2M \rightarrow 2(H)_{ads}M \quad (1)$$

$$H_3O^+ + e^- + M \rightarrow (H)_{ads}M + H_2O \quad (2)$$

Here, M is the metal active site for hydrogen and $(H)_{ads}M$ is the chemisorbed hydrogen. The other reactions involved in the ECH process include adsorption of unsaturated compounds (Eq. (3)), the hydrogenation reaction between the adsorbed unsaturated compounds and the adsorbed hydrogen (Eq. (4)), and desorption of the hydrogenated product (Eq. (5)).

$$(Y=Z)_{aq} + A \rightarrow (Y=Z)_{ads}A \quad (3)$$

$$2(H)_{ads}M + (Y=Z)_{ads}A \rightarrow (YH-ZH)_{ads}A + 2M \quad (4)$$

$$(YH-ZH)_{ads}A \rightarrow (YH-ZH)aq + A \quad (5)$$

Here, Y=Z is an unsaturated organic reactant, A is the adsorption sites for organic substrate, $(Y=Z)_{ads}A$ is the adsorbed organic compound, and $(YH-ZH)_{ads}A$ is the adsorbed hydrogenated product.

During ECH, hydrogen ($H_2$) is commonly formed as a side product from the cathode's chemisorbed hydrogen via the Tafel (Eq. (6)) or Heyrovsky (Eq. (7)) reactions. These processes compete with hydrogenation of organics and negatively affect the electrochemical efficiency (E.E.) of ECH. However, the hydrogen byproduct has value and can be further used in other catalytic processing.

$$(H)_{ads}M + (H)_{ads}M \rightarrow H_2 + 2M \quad (6)$$

$$(H)_{ads}M + (H^+)_{aq} + e^- \rightarrow H_2 + M \quad (7)$$

A few electrocatalytic hydrogenation studies of furfural to furfuryl alcohol have been reported at room temperature. Chu obtained 61.7% of furfuryl alcohol using a nano $TiO_2$ film electrode. But earlier studies by Parpot et al. explored electroreduction of furfural on Pt and Pb cathodes in 0.1 M $HClO_4$ and 0.1 M $H_2SO_4$, and on Cu in an alkaline medium. Interestingly, they noted 2-methylfuran in some of their final product mixtures, but reported neither yields nor optimized conditions for this little-discussed reaction. With the Pt cathode, the selectivity from furfural to furfuryl alcohol was 98% but the conversion remained very low (7.8%) after 24.5 h of electrolysis. With Cu in a carbonate buffer (pH 10), 80% of the furfural was selectively reduced to furfuryl alcohol and the conversion reached 90% within 5.5 h; this result echoed an earlier finding by Chamoulaud et al., which showed that furfuryl alcohol was formed with 95% selectivity using a copper-modified graphite felt cathode in a flow cell.

The present investigation explored ECH of furfural to furfuryl alcohol and 2-methylfuran in aqueous solution in a simple undivided cell with a sacrificial anode. This approach avoided the need for proton exchange membranes, lowering both electrical resistance and equipment costs relative to most literature studies, where divided cells and anodes made of noble metals, usually Pt, were used. In this Example, different anode and cathode materials as well as varying pH conditions were studied and their effects on the product yield and electrochemical efficiency were examined. Effect of starting furfural concentration and current density were also investigated. The continuous cathode reactivation via nickel ion reduction and deposition was verified using a divided cell. Furthermore, the competitive reaction kinetics for ECH of furfural and benzaldehyde were investigated.

Reagents and Electrodes:

Furfural (F) (≥98%), furfuryl alcohol (FA) (≥98%), 2-methylfuran (2-MF) (≥98%) and n-octane (>99%) were purchased from Sigma-Aldrich and used as received without further purification. Deionized (DI) water and methanol (>99.9%) from Sigma-Aldrich were used as solvents. The cathode material, including pure copper (Cu), pure aluminum (Al), pure iron (Fe), pure nickel (Ni) and stainless steel (SS) 308 were obtained from McMaster-Carr. Nickel alloy (80% Ni, 20% Fe) and pure nickel were used as sacrificial anodes and were purchased from The Science Company.

Electrochemical Cell Setup:

The bench-scale electrocatalysis unit consisted of a simple undivided cell, configured in a manner similar to that of Navarro et al. (FIG. 1). It was constructed using a mL thin layer chromatography (TLC) developing chamber, capped by a rubber stopper with holes for the anode and the cathode. To avoid oxidation of substrates on the anode side, a strip of nickel (2.8 cm×3 cm×0.1 cm) was used as the sacrificial anode. Two types of nickel strips were used: nickel alloy and pure nickel. Several cathode materials were tested, including Fe, 308 SS, Cu, Al and pure Ni.

Pretreatment of the electrodes was carried out to remove the metal oxides, which can deactivate the reaction when existing on the electrode surface. After polishing with sand paper, Ni, Cu, and SS electrodes were acid washed with 6.0 M HCl solution while Fe was immersed in glacial acetic acid for 1 h. The electrode made of Al required no acid wash. After pretreatment, all electrodes were rinsed with DI water.

Base case experiments used 50 mL of 100 mM furfural solution in 4:1 mixture of water and methanol, a good solvent for both electrolyte and organic substrates. Unless otherwise stated, 260% equivalent of electrons (1254 coulombs, 130% $H_2$ equivalent) based on 100 mM of furfural was passed to ensure sufficient conversion for all experiments. Ammonium chloride (0.2 M) was selected as the electrolyte because it was previously shown to promote reactant conversion with good electrochemical efficiency.

A dual channel power supply from Lambda (Model: LPD 422A FM) was used to provide a constant current to the cells with the positive and negative leads connected to anode and cathode electrodes, respectively. Multimeters from Omega (Model: HHM34) were used to measure current and voltage. Unless otherwise stated, a current density of 600 mA/dm² was used for most of the experiments. The voltage varied between 1.6 V and 2.1 V, depending upon the cathode materials and the distance between electrodes.

To investigate effects of nickel re-deposition on the product yield, a divided H-cell was used (FIG. 1) with a NAFION membrane separating the two chambers. Iron and pure nickel were used as the cathode and the anode. The catholyte was the same as in the undivided cell. There was only solvent (methanol:water, 1:4) and 0.2 M electrolyte in the anolyte.

Product Analyses:

Aqueous samples were diluted ten-fold with acetonitrile, filtered through 0.22 μm filters, and analyzed on a Shimadzu QP-5050A GC/MS. The GC used a Restek Rtx-1701 capillary column, 60 m×0.25 mm with a 0.25 μm film thickness, helium running at 1.0 ml/min as carrier gas, and a split ratio of 1:100. The injector temperature was set at 270° C. The GC oven program started at 40° C. for 1 min, then heated at 8° C./min to 80° C., then at 15° C./min to 260° C. The mass spectrometer was operated in the electron ionization (EI) mode at an ionization energy of 80 eV, a m/z ranging from 40 to 400, and a sampling interval of 0.34 s. The identification of species associated with each chromatographic peak was done by comparing the observed mass spectrum with the NIST library and then confirmed by injection of authentic samples. External standards were used to quantify furfural and the products of furfural reduction.

Calculations:

The conversion, selectivity, yield and electrochemical efficiency were calculated according to the following equations:

$$\text{Conversion} = ([\text{Reactant}]_{t=0} - [\text{Reactant}]_t)/[\text{Reactant}]_{t=0} \times 100 \qquad (8)$$

$$\text{Selectivity} = [\text{Product}_i]_t / ([\text{Product}_1]_t + [\text{Product}_2]_t) \times 100 \qquad (9)$$

$$\text{Yield} = [\text{Product}]_t / [\text{Reactant}]_{t=0} \times 100 \qquad (10)$$

$$\text{E.E.} = (m_1 \times n_1 + m_2 \times n_2)/(f \times m \times n) \times 100 \qquad (11)$$

Here, $m_1$, $m_2$ and m (mol) are the numbers of moles for furfuryl alcohol, 2-methylfuran and starting furfural, respectively; $n_1$ and $n_2$ are the numbers of electrons transferred during the reaction to furfuryl alcohol and 2-methylfuran, respectively ($m_1=2$, $n_2=4$), n is the number of electrons transferred during furfural reduction to furfuryl alcohol (n=2); f is the number of $H_2$ equivalents and it is equal to 130%. E.E. is calculated based on all the products (furfuryl alcohol and 2-methylfuran) unless otherwise stated.

TABLE 1

ECH of furfural using iron (cathode) and nickel alloy (anode) with different starting concentrations. 260% equiv. of electrons based on the nominal starting concentration was passed

| Furfural concentration (mM) | Current density (mA/dm²) | Run time (h) | Selectivity (FA)(%) | Selectivity (2-MF) (%) | E.E.[a] % | Mass balance |
|---|---|---|---|---|---|---|
| 20 | 175 | 2 | 100 ± 0.0 | b | 26 ± 5.0 | 71 ± 3.1 |
| 100 | 600 | 5 | 98 ± 0.1 | 2.0 ± 0.1 | 29 ± 3.5 | 64 ± 0.3 |
| 140 | 900 | 5 | 97 ± 1.2 | 3.0 ± 1.2 | 18 ± 0.7 | 68 ± 5.3 |

[a]Electrochemical efficiency was based on FA.
b Not detected. Solvent and electrolytes: 0.2M NH₄Cl in 50 mL water + methanol (4:1, V/V); pH 5.0.

Material Balance in ECH of Furfural Using Iron as the Cathode:

The selectivity and material balance were investigated by hydrogenating furfural using iron as the cathode and nickel alloy as the sacrificial anode in aqueous solution (Table 1). Furfuryl alcohol was the major product formed under these conditions, along with small quantities of 2-methylfuran. Pathway to these two products is shown in Scheme 1.

Scheme 1. Reaction scheme for ECH of furfuryl alcohol and 2-methylfuran.

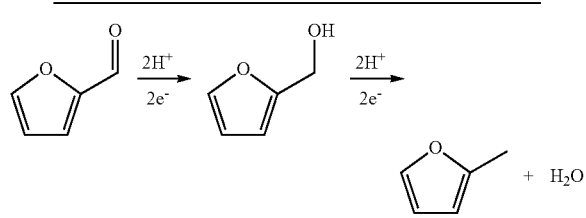

Figure 3:
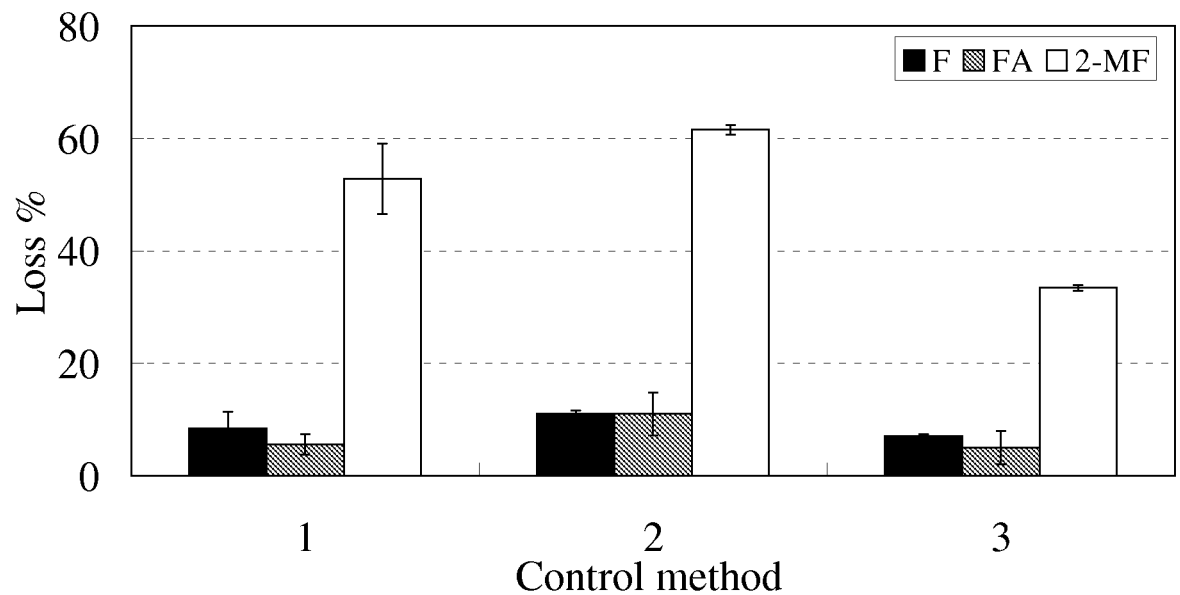
FIG. 3 illustrates the control experiments for ECH of furfural. The solutions for the control experiments include: 40 mM furfural, 40 mM furfuryl alcohol and 20 mM 2-methylfuran, 0.2 M $NH_4Cl$ in 50 mL water+methanol (4:1, V/V).

As Table 1 shows, complete material balance closure was not achieved in any of the experiments. Poor material balances for reactions in undivided ECH cells have been previously observed but were not clearly explained. FIG. 3 shows the results of three control experiments, performed without passing current, to quantify mass losses due to simple evaporation and chemical adsorption onto the electrodes: (1) substrate/electrolyte solution in cell without electrodes; (2) substrate/electrolyte solution in cell with electrodes; (3) substrate/electrolyte solution in cell with electrodes and a layer of octane on top to trap hydrophobic and volatile reaction species. There was no significant difference between controls (1) and (2) because the amount of organic compounds absorbed on the electrodes was small, on the order of $10^{-5}$ mmol. Controls (2) and (3) showed that evaporation contributed to the loss of reaction species as evidenced by less chemical loss with an octane layer trap. The relatively hydrophobic and volatile 2-methylfuran in particular was not very soluble in the aqueous electrolyte, so without the octane layer present as a trap, it separated from the aqueous phase and evaporated quickly.

TABLE 2

ECH of furfural (100 mM) without and with octane trap (12 mL) using iron (cathode) and nickel alloy (anode)

| Method | Conversion (%) | Selectivity (FA)(%) | Selectivity (2-MF)(%) | Yield (FA)(%) | E.E.[a] % | Mass balance |
|---|---|---|---|---|---|---|
| Without octane | 97 ± 1.4 | 98 ± 0.1 | 2.0 ± 0.1 | 61 ± 1.2 | 29 ± 3.5 | 64 ± 0.3 |
| With octane | 78 ± 4.2 | 98 ± 0.3 | 2.0 ± 0.3 | 63 ± 3.8 | 43 ± 1.0 | 85 ± 7.8 |

[a]Electrochemical efficiency was based on FA. Solvent and electrolytes: 0.2M NH$_4$Cl in 50 mL water + methanol (4:1, V/V); current density: 600 mA/dm$^2$; pH 5.0.

Table 2 presents results for the ECH of furfural, with and without the octane layer to enhance the recovery of furfuryl alcohol and 2-methylfuran. Reactant furfural was partially extracted into the octane layer, so its extent of conversion was less (78% vs 97% conversion) with octane present than in the octane-free run. Conversely, the improved product recovery with the octane-trap increased both the electrochemical efficiency (from 29% to 43%) and the material balance (from 64% to 85%). Control experiment (3) suggested that even with the octane layer, there was still significant material loss because of the evaporation and the experimental variability, which can be considered as one of the loss mechanisms for the remaining 15% of unaccounted material. Precipitate observed during the ECH of furfural was identified as a mixture of nickel metal and nickel hydroxide based on the analysis results from inductively coupled plasma optical emission spectrometer (ICPOES) and energy-dispersive X-ray spectroscopy (EDS) (not shown). Ongoing oxidation of the nickel anode (Eq. (12)) raised the nickel ion (Ni$^{2+}$) concentration while cathodic proton consumption raised the OH$^-$ concentration during electrolysis, leading to precipitation of nickel hydroxide. In addition, it was noted that under vigorous stirring conditions, nickel deposited on the cathode surface (Eq. (13)) could flake off to become part of the precipitated particles.

$$Ni(anode,s) \rightarrow Ni^{2+} + 2e^- \quad (12)$$

$$Ni^{2+} + 2e^- \rightarrow Ni(cathode,s) \quad (13)$$

After filtration, the precipitate was suspended into methanol and the solution was sonicated. Analysis of the resulting solution by GC/MS showed that organic species were adsorbed onto this precipitate, another reason for the mass loss. Despite incomplete closure of the mass balance, the data in Table 2 suffice to demonstrate the utility of ECH of furfural. In the following experiments, only the organic compounds in the solution were used in mass balance calculations.

Figure 4:
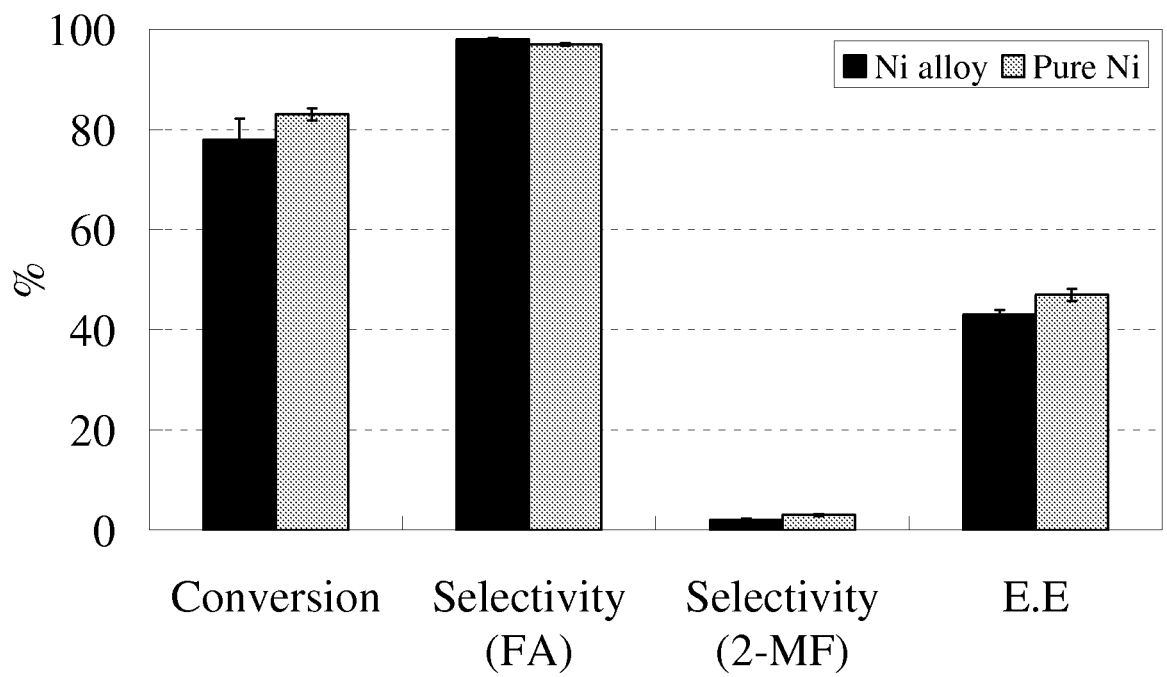
FIG. 4 illustrates ECH of furfural (100 mM) in 50 mL water+methanol (4:1, V/V) with 0.2 M $NH_4Cl$ using two different Ni anode materials: Ni alloy and pure Ni. Current density: 600 $mA/dm^2$; pH 5.0; E.E.: electrochemical efficiency based on FA.

Effect of Electrodes:

Both pure nickel and nickel-iron alloy were tested as sacrificial anodes for the ECH of furfural. Iron is the more easily oxidized metal, and the alloy's behavior might differ from that of the pure metals. However, the results (FIG. 4) for the two anode materials revealed no obvious differences in performance. Therefore, to avoid irrelevant complexity, pure nickel was used as anode material in all subsequent investigations.

For ECH of organic compounds, the catalytic cathode material was the key component in terms of product selectivity and electrochemical efficiency. In an undivided cell with a nickel sacrificial anode, nickel deposit was formed onto the cathode surface due to the reduction of nickel ion (Ni$^{2+}$), as shown in Eq. (13). Thus, both the original cathode surface material and the new deposited nickel layer may affect the ECH of furfural.

Figure 5:
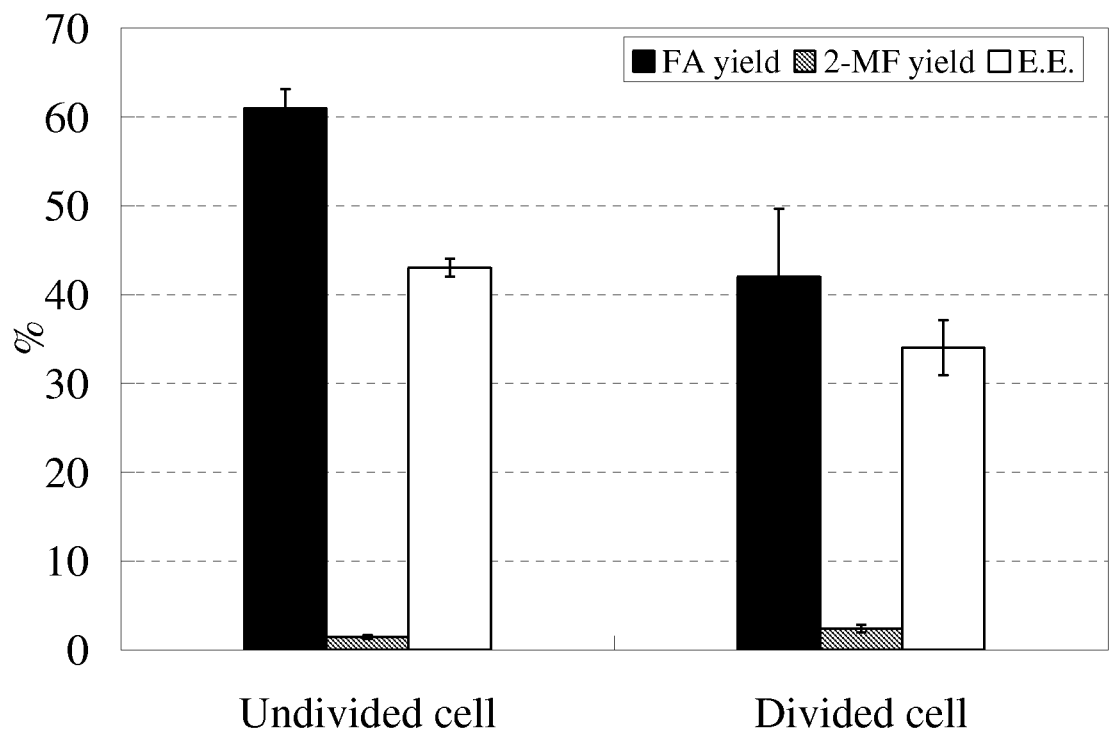
FIG. 5 illustrates product yield and electrochemical efficiency for ECH of furfural (100 mM) using Fe (cathode) and pure Ni (anode) in an undivided cell (50 mL water+methanol (4:1, V/V) with 0.2 M $NH_4Cl$) and a divided cell (both chambers: 50 mL water+methanol (4:1, V/V) with 0.2 M $NH_4Cl$). Current density: 600 $mA/dm^2$; pH 5.0.

To differentiate between the original cathode material and the influence of the nickel deposition, a divided H-cell was used with iron as the cathode and pure nickel as the anode. A NAFION membrane 117 was used to separate the two chambers and thus prevent nickel deposition on the Fe cathode. The divided H-cell had significantly lower furfuryl alcohol yield and electrochemical efficiency than the undivided cell (FIG. 5). In the undivided cell, the nickel deposits, examined by SEM, were in m range, resulting in relatively large surface area compared with the plain iron cathode in the divided cell. This is a possible reason for the better performance of the undivided cell. Important information can be obtained from this experiment: (a) the iron cathode alone without deposited nickel was electrochemically active for ECH of furfural, and (b) the deposition of nickel clearly enhanced the cathode's activity.

Figure 6:
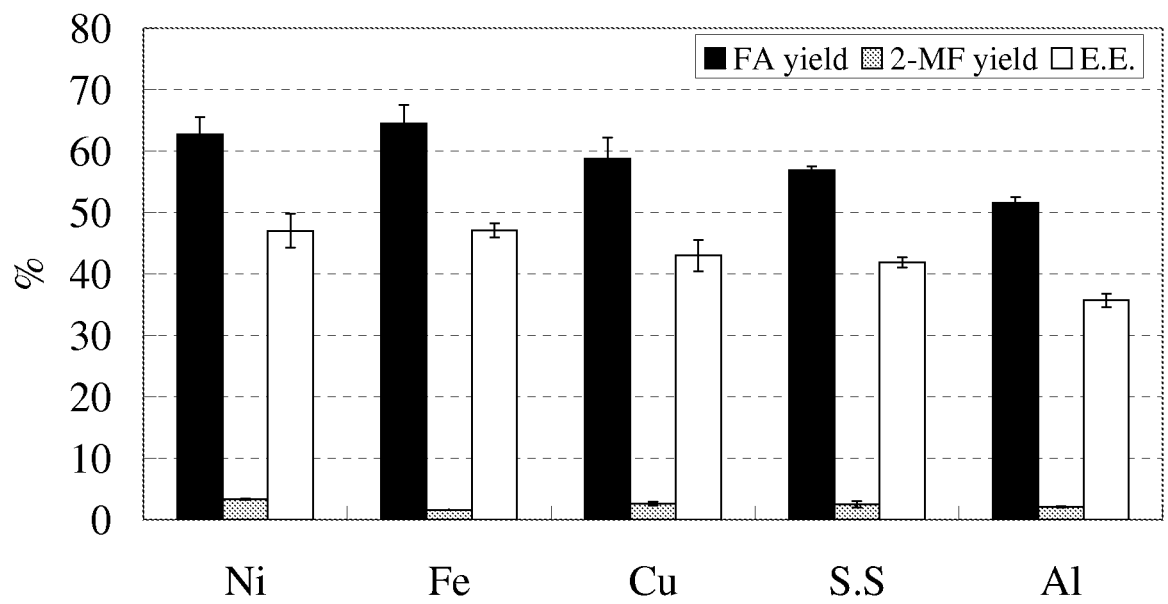
FIG. 6 illustrates product yields and electrochemical efficiency for ECH of furfural (100 mM) in 50 mL water+methanol (4:1, V/V) with 0.2 M $NH_4Cl$ using different cathode materials. Current density: 600 $mA/dm^2$; pH 5.0.

The effects of several additional cathode materials on product yields and electrochemical efficiency for furfuryl alcohol and 2-methylfuran formation were studied. These materials included Ni, Fe, Cu, 308 SS and Al. As can be seen in FIG. 6, the furfuryl alcohol yield increased in the order: Al<308 SS≤Cu<Ni<Fe. As for 2-methylfuran, Ni, Cu and 308 SS were slightly better than Fe and Al, but the differences were small. Electrochemical efficiencies for different cathode materials were also calculated and increased in the same order as the yields (FIG. 6). Vilar et al. stated that the cathode had practically no effect on the electrochemical efficiency during ECH of cyclohexanone, isophorone and acetylcyclohexene using a Ni sacrificial anode, but the results for ECH of furfural did show substantial differences. The reason for this difference was that Vilar et al. used pre-electrolysis to deposit nickel on the cathode material before adding organic compounds. In this investigation, pre-electrolysis was not used; instead, furfural was added to the solution at the beginning of the electrolysis. Without pre-electrolysis, there was no nickel deposited at the onset of reaction, and the unmodified cathode material contributed to the catalytic effect on the ECH of furfural. Later, when deposition of nickel had taken place for some time, the deposited nickel became the predominant catalyst for converting furfural. Over the course of ECH of furfural in the undivided cell, both the naked cathode and the deposited nickel contributed to the observed product yield and efficiency.

pH Effect:

Besides changing the electrode materials, the pH of the experimental solution was another important parameter affecting the ECH of furfural. It is expected that pH should affect the competition between hydrogenation of furfural (Eqs. (3)-(5)) and desorption of $H_{ads}$ (hydrogen evolution: Eqs (6) and (7)). The pH should have little effect on the thermal desorption of $H_{ads}$ (Eq. (6)) but should have a pronounced effect on its electrochemical desorption (Eq. (7)) because it involves $H_2O$ (neutral and alkaline pH) or $H_3O^+$ (acidic pH) in the process.

Different pH conditions (pH 1.0, 5.0 and 9.5) were investigated for ECH of furfural (100 mM) using pure nickel as cathode and anode. The standard solution of water, methanol and $NH_4Cl$ used in these experiments has a pH 5.0. HCl was added to the above solution to change the pH to 1.0, while $NH_4OH$ (aqueous ammonia) was used to adjust the solution to pH 9.5.

The effect of pH on furfural conversion, product selectivity, yield, electrochemical efficiency and the material balance are shown in Table 3. The conversion of furfural at pH 1.0 was much lower than that at pH 5.0 and 9.5. As shown in Eq. (7), lowering pH (i.e. raising hydronium ion concentration) should raise the hydrogen evolution rate at the expense of furfural conversion and electrochemical efficiency. It was interesting that the selectivity of 2-methylfuran was increased as pH 1.0. To further enhance selectivity to 2-methylfuran, even more acidic conditions than pH 1.0 could be employed, but besides further loss of current to $H_2$ formation, acid catalyzed polymerization of furfuryl alcohol would then be expected.

The overall electrochemical efficiency based on the two products was highest at pH 5.0. At lower pH, the competitive reaction (Eqs. (6) and (7)) for hydrogen evolution was favored because of the high hydronium ion concentration. At higher pH 9.5, the hydrogenation reaction should be favored over the hydrogen evolution. However, the pH of the solution changed from 9.5 to 11 during the electrolysis. Furfural was not stable at this alkaline condition and the concentration of furfural decreased, which has been examined using control experiments (data not shown here). The decrease of furfural concentration lowered the reaction rate of furfural hydrogenation, thus resulting in lower furfural conversion and electrochemical efficiency (Table 3), which can also be observed in FIGS. 7 and 8.

TABLE 3

ECH of furfural (100 mM) using pure nickel for cathode and anode under different pH conditions

| pH | Conversion | Selectivity (FA)(%) | Selectivity (2-MF)(%) | Yield (FA) % | Yield (2-MF) % | E.E. % | Mass balance % |
|---|---|---|---|---|---|---|---|
| 1.0 | 66 ± 3.0 | 86 ± 1.3 | 14 ± 1.3 | 39 ± 3.1 | 6.4 ± 0.2 | 39 ± 2.1 | 79 ± 5.9 |
| 5.0 | 80 ± 1.7 | 95 ± 0.0 | 5.0 ± 0.0 | 63 ± 2.8 | 3.3 ± 0.1 | 56 ± 2.2 | 86 ± 1.3 |
| 9.5 | 74 ± 2.3 | 93 ± 0.1 | 7.0 ± 0.1 | 24 ± 0.7 | 1.9 ± 0.0 | 23 ± 0.5 | 53 ± 1.6 |

Solvent and electrolytes: 0.2M $NH_4Cl$ in 50 mL water + methanol (4:1, V/V); current density: 600 mA/dm$^2$.

Figure 7:
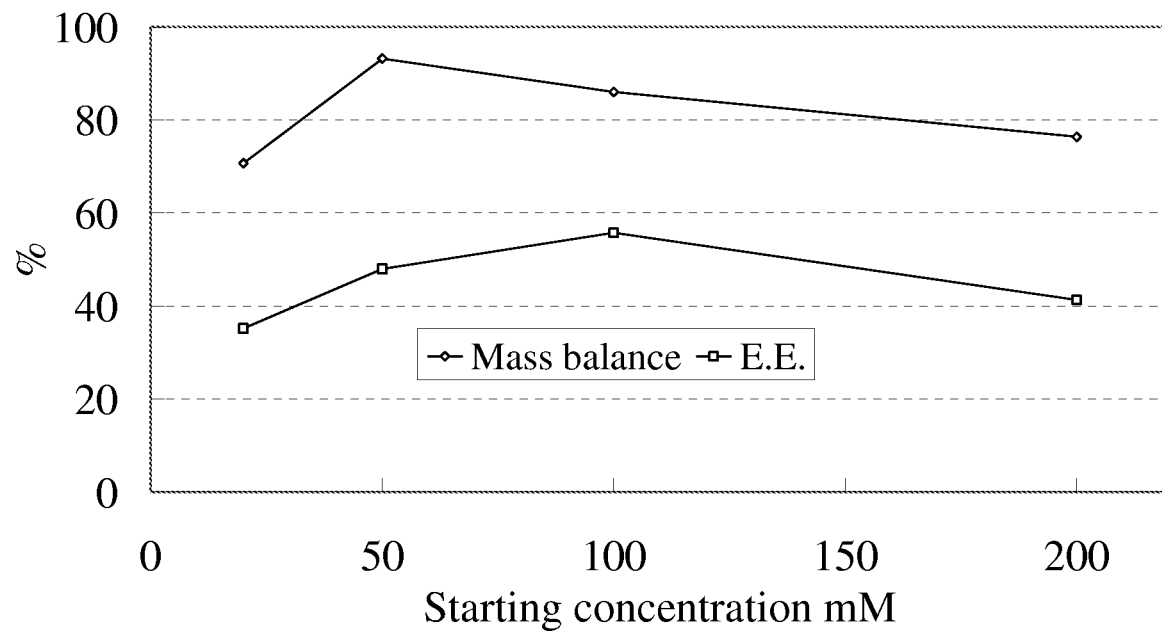
FIG. 7 illustrates the effect of different starting concentrations of furfural on mass balance and electrochemical efficiency using Ni (cathode) and Ni (anode) in undivided cell. Solvent and electrolytes: 0.2 M $NH_4Cl$ in 50 mL water+methanol (4:1, V/V). Current density: 600 $mA/dm^2$; pH 5.0. 260% equiv. of electrons based on the nominal starting concentration was passed.

Influence of Starting Reactant Concentration:

Different starting concentrations of furfural were chosen to study their effects on the electrochemical efficiency, furfural conversion and product yield during ECH. As shown in FIG. 7, the electrochemical efficiency was maximized when the starting concentration was 100 mM. As the concentration was reduced below 100 mM, the hydrogenation reaction (Eq. (4)) became slower so that hydrogen evolution became more competitive. When the concentration of furfural is large, hydrogenation should be favored relative to the hydrogen evolution reaction. However, more precipitate was observed at larger furfural concentrations because more electrons were passed and more nickel ion was produced. Additionally, more organic species were adsorbed onto the precipitate particles, thus reducing material balance closure (FIG. 7). Because of the loss of product species as evidenced by the mass balance, the calculated electrochemical efficiency at 200 mM was smaller than that at 100 mM.

Figure 8:
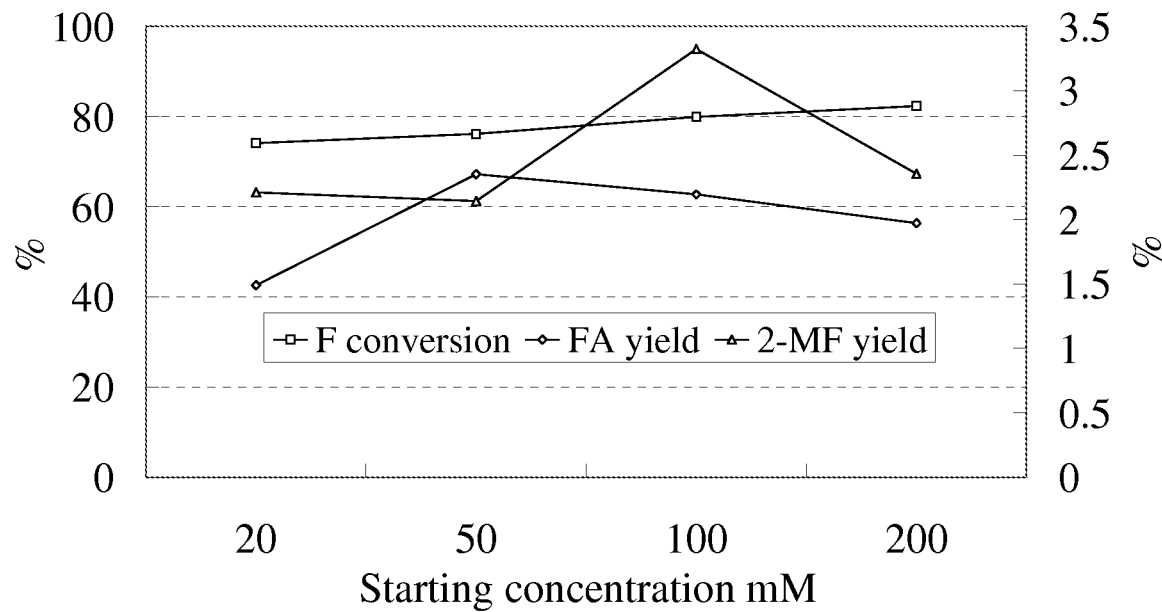
FIG. 8 illustrates the effect of different starting concentrations of furfural on conversion, furfuryl alcohol yield (left y-axis) and 2-methylfuran yield (right y-axis) using Ni (cathode) and Ni (anode) in undivided cell. Solvent and electrolytes: 0.2 M $NH_4Cl$ in 50 mL water+methanol (4:1, V/V). Current density: 600 $mA/dm^2$; pH 5.0.

As shown in FIG. 7, furfural conversion increased slightly as the starting furfural concentration increased. Furfuryl alcohol and 2-methylfuran yields showed a maximum at 50 mM and 100 mM, respectively (FIG. 8).

Figure 9:
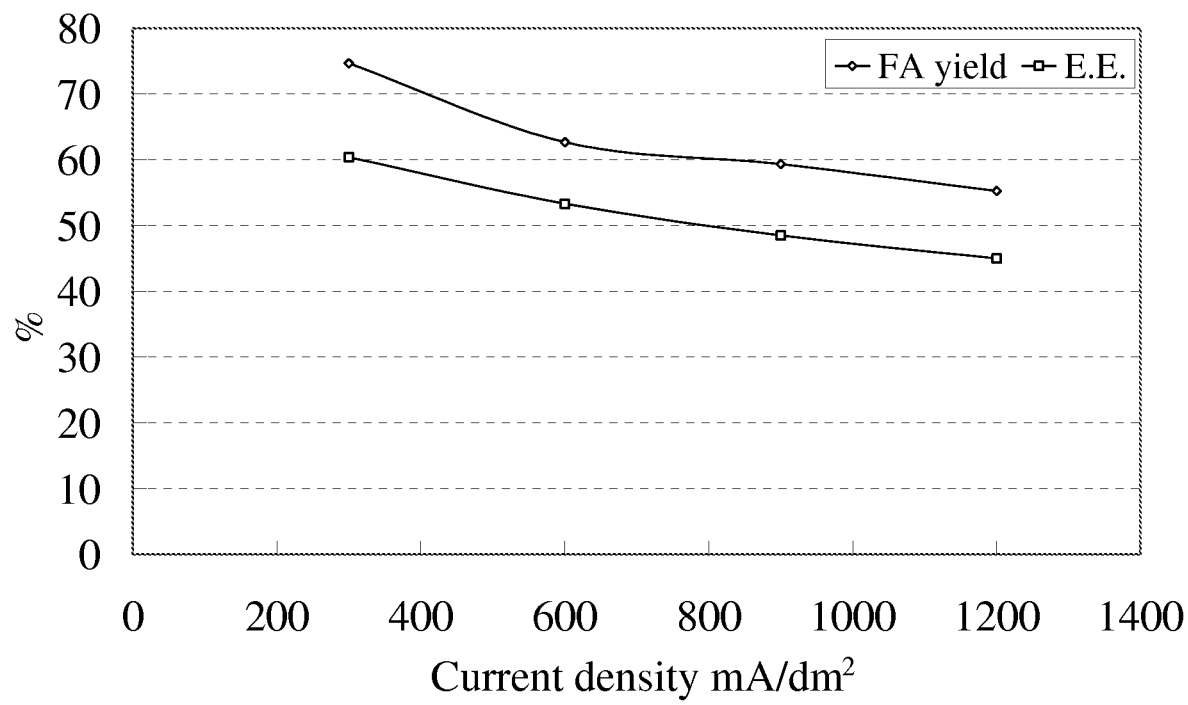
FIG. 9 illustrates the effect of current density on electrochemical efficiency and furfuryl alcohol yield during ECH of furfural using nickel as cathode and anode in undivided cell. Solvent and electrolytes: 0.2 M $NH_4Cl$ in 50 mL water+methanol (4:1, V/V); pH 5.0.

Effect of Current Density:

Current density, directly related to the total reaction rate, may have an effect on the electrochemical efficiency and product yield. Several different current densities in the range of 300-1200 mA/dm$^2$ were studied. Results showed that the electrochemical efficiency decreased when increasing the current density from 300 to 1200 mA/dm$^2$ (FIG. 9). An optimum current density usually exists for ECH of organic compounds. When the current density is smaller than this optimum value, the surface coverage of the $H_{ads}$ is smaller. The probability of the collision between $H_{ads}$ and (furfural)$_{ads}$ is lower, and the electrochemical desorption of $H_{ads}$ (Eq. (7)) is important, resulting in a smaller electrochemical efficiency. When the current density is higher than the optimum value, the adsorption sites M are saturated with $H_{ads}$, so no matter how the current density is increased, the hydrogenation of furfural (Eq. (4)) and thermochemical desorption of $H_{ads}$ (Eq. (6)) are not affected. However, higher current density would result in a more negative cathode potential, thus increasing the electrochemical desorption rate of $H_{ads}$ (Eq. (7)) and decreasing the electrochemical efficiency. The lowest current density 300 mA/dm$^2$ studied in this paper may exceed the optimum current density, thus a continuous decrease of electrochemical efficiency was observed.

Figure 10:
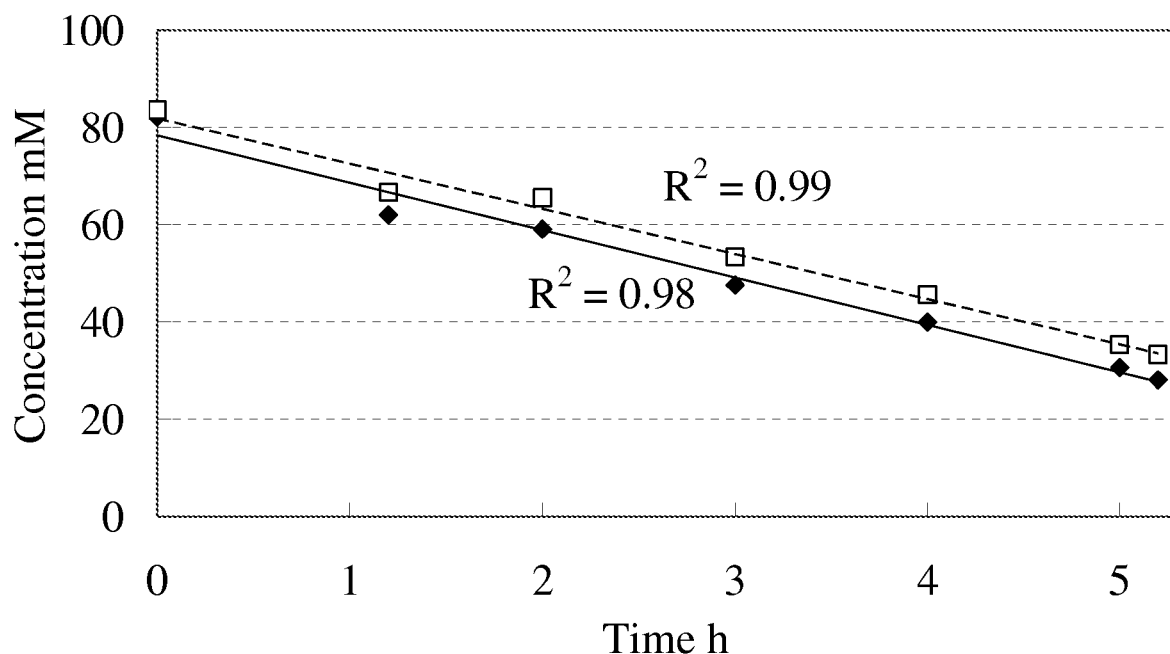
FIG. 10 illustrates the concentration of furfural changes during ECH of furfural using nickel as cathode and anode in undivided cell. Only 100 mM furfural as reactant (dash line), mixture of 100 mM furfural and 100 mM benzaldehyde as reactant (solid line). Solvent and electrolytes: 0.2 M $NH_4Cl$ in 50 mL water+methanol (4:1, V/V). Current density: 600 $mA/dm^2$; pH 5.0.

Competitive Reaction Kinetics:

Furfural is usually produced by acid hydrolysis of biomass residues, such as corn cobs, corn stover, rice straw, wheat straw, forest slash and sawdust. Organic compounds derived from cellulose or lignin may compete with furfural hydrogenation. Competitive ECH of furfural with benzaldehyde, also an aromatic aldehyde, was therefore studied. FIG. 10 shows reactant concentrations vs. time for the ECH of a mixture comprising 80 mM furfural and 80 mM benzaldehyde. Slopes of the resulting linear fits represent conversion rates on the nickel catalyst; these rates were very similar for furfural and benzaldehyde at 9.7 and 9.4 mM/h, respectively, consistent with their common character as aromatic aldehydes. The total of 19.1 mM/h conversion rate in the 50 mL sample volume was effected by a 133 mA current, yielding an overall electrochemical efficiency of 37.3%, similar to those found in the single substrate experiments. Thus, neither selectivity difference nor interference is seen between these two substrates.

Electrocatalytic hydrogenation of furfural was accomplished using an undivided electrolytic cell with a sacrificial anode immersed in aqueous solution. Furfuryl alcohol and 2-methylfuran were the major and minor products, respectively. Pure nickel and nickel alloy anode materials behaved similarly in terms of product selectivity. Conversely, the cathode material had a large effect on the electrocatalytic hydrogenation of furfural, with nickel and iron giving the best results among those studied. In this system, nickel deposition improved the activity and selectivity of the original cathode. Without pre-electrolysis during electrocatalytic hydrogenation of furfural, both the original cathode material and deposited nickel contributed to the catalytic effect. The pH of the solution also affected product selectivities and electrochemical efficiency. Furfuryl alcohol had an optimum yield at pH 5.0, while 2-methylfuran was favored at pH 1.0. As current density increased, furfuryl alcohol yield and electrochemical efficiency were decreased. In direct competition, ECH reaction rates of furfural and of benzaldehyde were similar, with no signs of mutual interference.

Vaart et al. stated that atomic hydrogen concentration at the catalyst surface can be controlled and maintained by the applied potential. This allows the operation of the ECH process at ambient pressures compared with the extremely high hydrogen pressure in catalytic hydrogenation. Based on this investigation, electrocatalytic hydrogenation of furfural using a sacrificial anode could be a very promising process for furfuryl alcohol production.

Example 2

Aqueous ECH and ECHDO of Bio-Oil Components Using a Ru/ACC Cathode

Bio-oil, the liquid product from fast pyrolysis of biomass, is a promising starting material for transportation fuel production. However, the raw bio-oil is not ready for end use because of its tendency to polymerize. This reactivity is largely due to the presence of unsaturated oxygenates such as aldehydes, ketones, carboxylic acids and phenols. Thus, for long-term storage and any further upgrading, bio-oil must be stabilized in order to minimize downstream coke formation, catalyst deactivation and carbon loss to the gas phase.

Catalytic hydrogenation has been shown to be a good method for bio-oil stabilization, converting most aldehydes, ketones, phenols and sugars to saturated alcohols and polyols. However, such hydrogenation is typically run at temperature over 100° C., high enough to cause accelerated bio-oil polymerization. Thus, any process to stabilize bio-oil would ideally operate at milder conditions. This example illustrates a process for bio-oil stabilization via mild (<100° C. or <80° C. and ambient pressure) electrocatalytic hydrogenation (ECH). These mild conditions minimize both polymerization and catalyst deactivation by coke formation. During the ECH process, instead of coming from an external hydrogen supply, atomic hydrogen is formed in situ on the catalytic electrode surface where it is available to hydrogenate organic substrates. This strategy simplifies processing and avoids the need for externally supplied, fossil-based hydrogen gas and associated handling equipment. Ideally, the needed electricity would come from carbon-free sources such as solar, wind, or even nuclear power. Electrocatalytic hydrogenation thus represents a green, carbon-retentive pathway for stabilization (and potentially further upgrading) of biomass-derived bio-oil to produce fuels and chemicals.

Lignin-derived phenolic compounds account for 25-30% of the whole bio-oil, but have a lower oxygen content (22-30 wt % vs. 33-40 wt % for whole bio-oil, dry basis). Furthermore, compared to other bio-oil components such as aldehydes and ketones, phenolic compounds are more resistant to hydrogenation. Therefore phenols were chosen as model substrates for this example.

Previous research on ECH of phenolic compounds has shown that large cathode surface areas are usually necessary to achieve high reaction rates. Electrodes made with pressed metallic powder particles have been successfully used, but their mechanical strength is weak if a binding material is not used, and much surface area is lost in the powder pressing step. To overcome the disadvantages of pressed electrodes, Menard and co-workers developed a new electrode by entrapping the catalytic powders into reticulated vitreous carbon (RVC). This is an effective system to test different classical catalytic hydrogenation catalysts using electrochemistry. However, the catalyst powders are mobile, so the amount of active catalysts involved in the actual hydrogenation is difficult to measure and the electrode may be destroyed by strong disturbance.

To develop a well-defined catalytic cathode, a ruthenium catalyst was immobilized onto activated carbon cloth (ACC) using incipient wetness impregnation and cation exchange methods. The ACC is considered a good catalyst support due to its high rates of adsorption, high surface area (1000 $m^2/g$ to 2100 $m^2/g$) and potential for easy in situ regeneration. Ruthenium supported on carbon has been shown to be an efficient catalyst for classical hydrogenation of various organics such as phenols, organic acids, amino acids and bio-oil itself.

In this investigation, ECH of guaiacol was assessed in terms of reactivity, product selectivity and electrochemical efficiency (E.E.) as functions of catalyst parameters (e.g. preparation methods, precursor types, ruthenium content, type of support) and reaction conditions (temperature and pH). Furthermore, ECH of two other phenolic model compounds, phenol and syringol, were also investigated using the same conditions as for guaiacol ECH.

Reagents and Materials:

Guaiacol (98+%) and 2-methoxycyclohexanol (99%) were obtained from Alfa Aesar. 2,6-dimethoxyphenol (syringol) (99%) was purchased from Sigma-Aldrich and cyclohexanol (99+%) was from Mallinckrodt. All of the above compounds were used as received without further purification. Phenol, from Mallinckrodt, was purified to remove moisture.

ZORFLEX ACC FM100 was obtained from Calgon Carbon Co. Ruthenium (III) chloride ($RuCl_3$) hydrate (99.9% PGM basis, Ru 38% min), hexaammineruthenium (III) chloride ($Ru(NH_3)_6Cl_3$, Ru 32.1% min) and ruthenium (III) nitrosyl nitrate ($Ru(NO)(NO_3)_3$, Ru 31.3% min) were bought from Alfa Aesar.

Catalyst Preparation:

ZORFLEX ACC FM100 was chosen as the support for the ruthenium catalysts due to good conductivity and high surface area. For most of the experiments, ACC was washed in DI water; this material was labeled "original ACC". According to energy dispersive X-ray spectroscopy (EDX) analysis, there were some mineral impurities in the original cloth (Table 4). To probe the effects of the catalyst support, "washed ACC" was obtained by washing ACC in boiling concentrated HCl solution for 3 days, thoroughly rinsing with DI water to remove residual HCl, and then drying in the oven at 105° C. EDX of this material only showed C, O and small amounts of Cl, presumably a residue from the HCl washing, as there was no Cl in the original ACC.

TABLE 4

Energy dispersive X-ray analyses of the original ACC and washed ACC

| Element | Weight % Original ACC | Weight % Washed ACC |
|---|---|---|
| C | 80.9 ± 0.48 | 92.0 ± 0.05 |
| O | 12.1 ± 0.03 | 7.3 ± 0.05 |
| Cl | — | 0.8 ± 0.01 |
| Al | 2.6 ± 0.16 | — |
| S | 0.3 ± 0.06 | — |
| Zn | 4.1 ± 0.29 | — |

Two methods were used for the catalyst preparation: incipient wetness impregnation and cation exchange. For incipient wetness impregnation, three precursors were used, including $Ru(NH_3)_6Cl_3$, $Ru(NO)(NO_3)_3$ and $RuCl_3$. For $Ru(NH_3)_6Cl_3$ and $Ru(NO)(NO_3)_3$, two ruthenium loadings (nominal 3 wt % and 5 wt %) were prepared, while only 3 wt % (nominal) ruthenium content was used for $RuCl_3$ because of its relatively low solubility in water. A piece of ACC (1.3 cm×3.0 cm) was first soaked in ruthenium precursor solution to saturate the ACC pores. KIMWIPES were then used to remove the excess solution after the ACC was taken out of the solution. The wet ACC was first dried under room conditions, then vacuum dried at room temperature, and finally reduced with $H_2$ in a Parr pressure reactor (model 452HC) at 500 psi and 220° C.

$Ru(NH_3)_6Cl_3$ was used as the precursor for cation exchange preparation and five ruthenium loadings (nominal 1 wt %, 1.5 wt %, 3 wt %, 5 wt % and 6.6 wt %) were prepared. A piece of ACC was first pre-oxidized using boiling 1 N $HNO_3$ solution for 24 hours. The pretreated ACC was then washed thoroughly with DI water to remove the residual $HNO_3$ and dried under vacuum at room temperature. After drying, it was soaked in $Ru(NH_3)_6Cl_3$ solution with 1 M ammonia overnight to exchange $Ru(NH_3)_6^{3+}$ onto the cloth. The ACC was removed, washed carefully with DI water, and then dried under vacuum at room temperature, and reduced with $H_2$ at 500 psi and 220° C. in a Parr pressure reactor.

To facilitate the recognition of the catalysts, each type of catalyst was assigned a catalyst code. For the catalysts prepared using incipient wetness impregnation and with $Ru(NH_3)_6Cl_3$ as precursor, catalyst codes Ru3/ACC-IW-NH3 and Ru5/ACC-IW-NH3 were used to represent ruthenium contents 3 wt % and 5 wt %, respectively. "IW" refers to incipient wetness impregnation and NH3 designates $Ru(NH_3)_6Cl_3$ as the precursor. In the same way, Ru3/ACC-IW-NO and Ru5/ACC-IW-NO are catalysts prepared with $Ru(NO)(NO_3)_3$ as precursor. When using $RuCl_3$ as the precursor with incipient wetness impregnation method, a code of Ru3/ACC-IW-Cl was used. As for the catalysts prepared using cation exchange and with $Ru(NH_3)_6Cl_3$ as precursor, catalyst codes Ru/ACC-CE-NH3 was used. For the catalysts (3 wt % Ru) prepared on HCl washed ACC with $RuCl_3$ as precursor, the code of Ru3/ACC-IW-Cl-AW was used, where "AW" stands for acid washed.

Catalysts Characterization:

Ruthenium contents of the catalysts were measured on a Varian 710-ES inductively coupled plasma optical emission spectrometer (ICP-OES). The catalysts were digested using aqua regia in a boiling water bath for 4 hr, filtered and diluted with DI water. The standards prepared with $RuCl_3$ were used to quantify the ruthenium content over a concentration range of 0.08 ppm to 50 ppm.

Scanning electron microscopy (SEM) on a JEOL JSM-7500F and a JEOL 6400V were used to image the catalyst support and the morphology of ruthenium particles on the support. The catalysts were mounted onto the stubs with carbon paste and then dried under vacuum overnight. Secondary electron imaging was used to obtain the images. Surface chemical composition was characterized by EDX coupled with the JEOL 6400V SEM.

Brunauer-Emmett-Teller (BET) surface area, micropore area and micropore volume of the samples were measured on a MICROMERITICS ASAP 2010 system using static volumetric adsorption and desorption method. Nitrogen was used as the adsorptive gas and the measurement was done at 77 K. Nitrogen pressure was increased until 99% of the nitrogen saturation pressure was reached. The total surface area of the sample was calculated using the BET method in the adsorption isotherm from 0.06 to 0.20 relative pressures. The micropore volume was calculated from desorption isotherm using the BJH (Barrett, Joyner and Hallender) method.

Ash analysis (NREL method) was used to analyze the ash content in the original ACC and HCl washed ACC. Samples of 0.5 to 2.0 g were weighed to the nearest 0.1 mg and transferred to dried crucibles. A muffle furnace set to 575±25° C. was used to ash the samples to constant weights. After cooling in a desiccator, the residue was weighed to determine the ash content.

Experimental Setup:

The electrochemical hydrogenation was carried out in a two-chamber glass H-cell, separated with a Dupont NAFION-117 membrane. The catholyte (30 mL) was 0.2 M HCl, 0.2 M NaCl or 0.2 M NaOH, depending on the experiments. Ru/ACC prepared as described above was used as the working electrode (cathode). The anolyte (30 mL) was 0.2 M phosphate buffer (pH=7), and a Pt wire was used as the counter electrode (anode). The whole cell was placed in a water bath for experiments at controlled temperatures such as 50° C. and 80° C. The ECH was carried out under galvanostatic control (100 mA) with a dual channel potentiostat from Lambda (Model: LPD 422A FM). Before the electrochemical hydrogenation, 10 min pre-electrolysis (80 mA) was applied to reduce the ruthenium to $Ru^0$. Then 1 mL 620 mM guaiacol solution in isopropanol was added to the cathode chamber to make an initial concentration of guaiacol equal to 20 mM. For all the experiments, the electrocatalytic hydrogenation was performed for 2 hours.

Product Analysis:

Chemical analysis proceeded by withdrawing 1 mL sample aliquots at discrete time intervals from the cathode and the anode chambers. The samples were further saturated with NaCl, acidified to pH=1 and then 1 mL chloroform was added to extract the organics. After the experiments, the Ru/ACC catalyst was immersed in 5 mL chloroform and the solution was sonicated for 15 min to desorb any adsorbed organics into the solution. The solution was then filtered using 0.22 μm syringe filter for GC/MS analysis.

According to Pradhan and Sandle, oxidation with nitric acid generates surface oxygen complexes at the entrance of the pores, restricting access of $N_2$ molecules to the micropores. Thus this type of catalyst shows reduced surface area and micropore volume.

TABLE 5

BET surface area, micropore area and micropore volume of the blank ACC and the catalysts

| Sample name | Preparation method | Precursor | BET surface area m²/g | Micropore area m²/g | Micropore volume cm³/g |
|---|---|---|---|---|---|
| Blank ACC | DI water wash $H_2$ reduction at 220° C. and 500 psi | — | 1010 | 685 | 0.30 |
| Ru3/ACC-IW-Cl | Incipient wetness impregnation | $RuCl_3$ | 904 | 599 | 0.27 |
| Ru3/ACC-IW-NH3 | | $Ru(NH_3)_6Cl_3$ | 800 | 551 | 0.26 |
| Ru3/ACC-IW-NO | | $Ru(NO)(NO_3)_3$ | 879 | 612 | 0.28 |
| Ru6.6/ACC-CE-NH3 | Cation exchange method | $Ru(NH_3)_6Cl_3$ | 341 | 139 | 0.06 |

All the samples were analyzed on a Shimadzu QP-5050A GC/MS. The GC used a Restek Rtx-1701 capillary column, 60 m×0.25 mm with a 0.25 μm film thickness, a 1.0 ml/min Helium carrier gas flow rate, and a split ratio of 1:40. The injector temperature was set at 270° C. The GC oven program started at 40° C. for 1 min, and then heated at 15° C./min to 260° C. The mass spectrometer was operated in the Electron Ionization (EI) mode at an ionization energy of 80 eV, a m/z ranging from 28 to 400, and a sampling interval of 0.34 s. Species associated with each chromatographic peak were identified by comparing their observed mass spectrum with the NIST library and then confirmed by injection of authentic samples. External standards were also used to identify compounds and quantify the peaks.

Calculations:

The conversion, selectivity and electrochemical efficiency were calculated according to the following equations:

$$\text{Conversion} = (\text{moles consumed of reactant/initial moles of reactant}) \times 100 \quad (1)$$

$$\text{Selectivity} = (\text{moles of desired product/total moles of products}) \times 100 \quad (2)$$

$$\text{E.E.} = (\text{Electrons used to generate products/Total electrons passed}) \times 100 \quad (3)$$

Catalysts Characterization:

A high surface area cathode is an important property for the efficient reduction of guaiacol. BET surface area, micropore area and micropore volume of the catalysts were analyzed (Table 5). In order to assess the actual support properties for the catalysts, ACC was pretreated in the same manner (designated the "blank ACC") as the catalyst, by washing with DI water and reducing with hydrogen at 220° C. and 500 psi. The blank ACC has a surface area of 1,010 m²/g, very similar to the reported value in the literature. Compared with other supports used for the cathodes, this kind of support has much larger surface area. The majority of the pores are micropores and the volume is 0.30 cm³/g (Table 5). Upon loading with the different ruthenium precursors, the supports' micropore volumes decreased, suggesting that some of the micropores were blocked by ruthenium. As shown in Table 5, catalyst Ru6.6/ACC-CE-NH3, prepared by cation exchange, has very different surface area and micropore volume than the other catalysts because the support was pretreated in 1N boiling nitric acid for 24 hrs.

Figure 11:
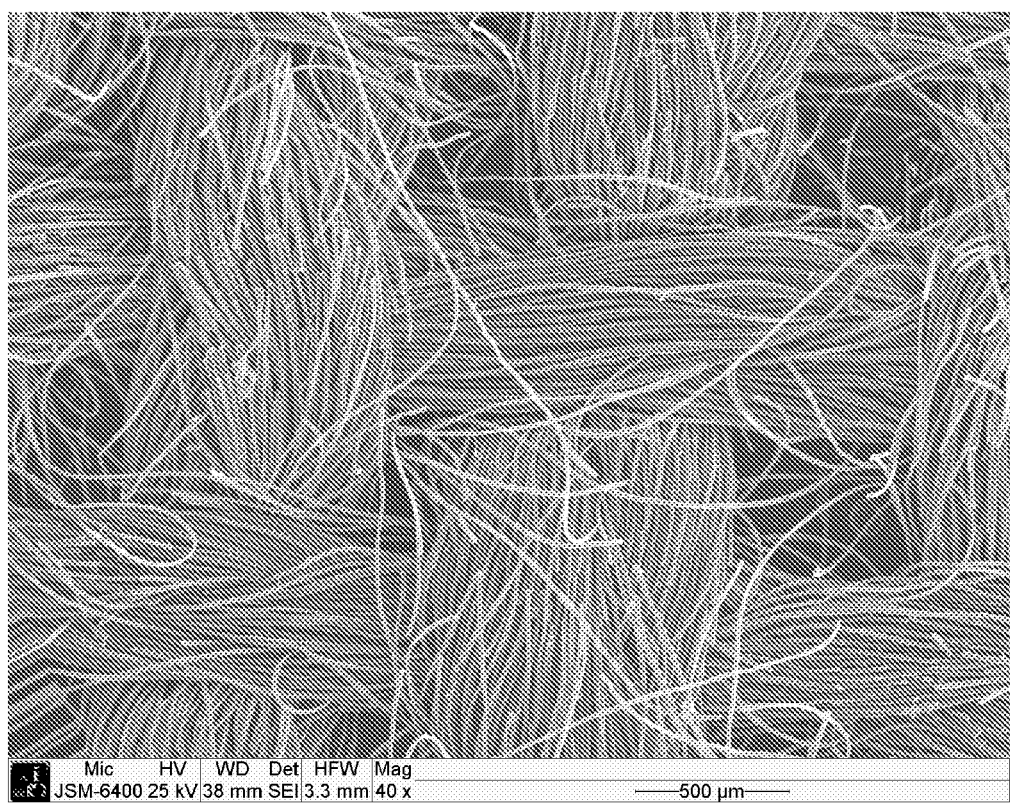
FIG. 11 is a SEM image of blank ACC FM100. Scale bar: 500 μm.

FIG. 11 shows a SEM image of the blank ACC FM100. With its carbon fibers knitted together, the conductivity is very good, making it a good electrocatalyst support. Because it is monolithic, filtration or decantation is not needed after the reaction. This flexible support can conveniently be cut and shaped to fit into different kinds of reactors.

Figure 12:
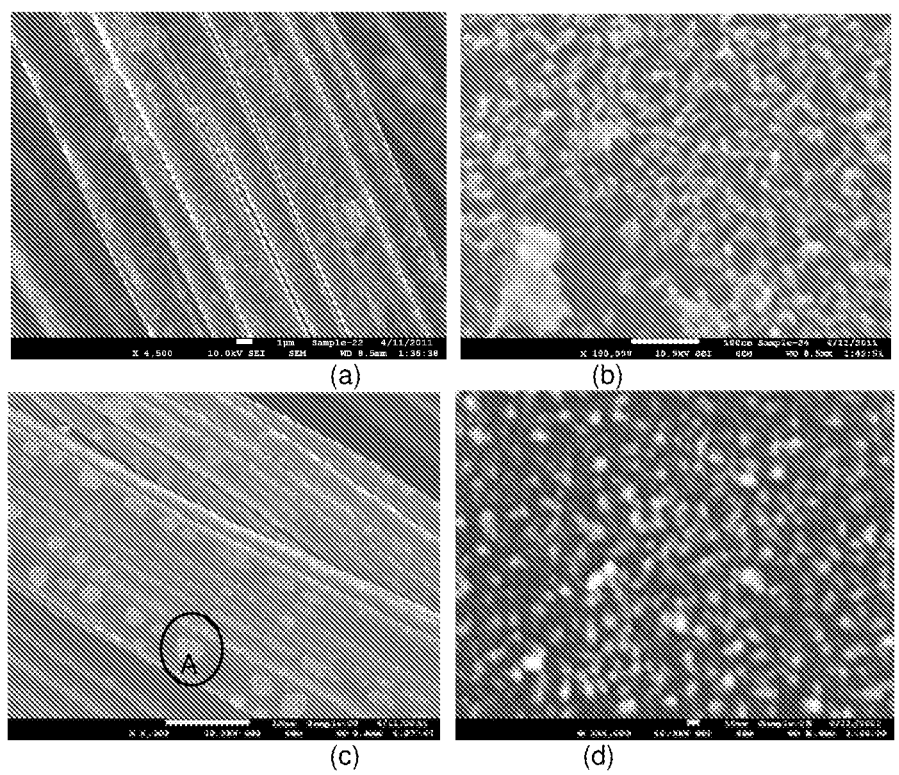
FIGS. 12(a) and (b) are SEM images of Ru3/ACC-IW-NH3 prepared with incipient wetness impregnation using $Ru(NH_3)_6Cl_3$ as precursor.
FIGS. 12(c) and (d) are SEM images of Ru5/ACC-CE-NH3 prepared using cation exchange method using $Ru(NH_3)_6Cl_3$ as precursor. Scale bar: (a) 1 μm; (b) 100 nm; (c) 10 μm; (b) 10 nm.

SEM images of the catalysts (IW series) prepared by incipient wetness impregnation with precursor $Ru(NH_3)_6Cl_3$ are shown in FIG. 12 (a) and (b). The distribution of ruthenium, seen as white spots in FIG. 12(a), is clearly not uniform, as expected for the poorly controlled incipient wetness impregnation method. Zooming in on one of the white spots reveals nanoparticles (FIG. 12(b)) but also larger clumps of ruthenium (100 nm range), which decrease the metal dispersion. For the cation exchange (CE series) preparations, the $HNO_3$ pre-oxidation of the ACC fiber surface forms oxygenated functional groups such as carboxyl, lactone, phenolic hydroxyl and quinone groups. When loading the ACC in the ruthenium salt solution, metal cations will ion pair with the surface anionic sites. After catalyst reduction under hydrogen, white spots show up on the ACC fiber (FIG. 12(c), circle A). Zooming in on these white spots reveals nanoparticles in the 10-20 nm range with no large ruthenium accumulations visible (FIG. 12(d)). Compared with the IW preparation, these nanoparticles tend to be isolated from each other as opposed to forming a continuous sheet.

Reactions Involved in ECH of Guaiacol:

Reactions involved in ECH of guaiacol include: generation of adsorbed atomic hydrogen (Eq. 4), adsorption of guaiacol (Eq. 5), hydrogenation reaction between the adsorbed guaiacol and the adsorbed hydrogen (Eq. 6), and desorption of the hydrogenated product (Eq. 7).

$$H_3O^+ + e^- + M \rightarrow (H)_{ads}M + H_2O \quad (4)$$

$$\text{Guaiacol} + A \rightarrow (\text{Guaiacol})_{ads}A \quad (5)$$

$$x(H)_{ads}M + (\text{Guaiacol})_{ads}A \rightarrow (\text{Product})_{ads}A + xM \quad (6)$$

$$(\text{Product})_{ads}A \rightarrow \text{Product} + A \quad (7)$$

Here, M is the metal active site for hydrogen, $(H)_{ads}M$ is the chemisorbed atomic hydrogen, A is the adsorption sites for guaiacol, $(\text{Guaiacol})_{ads}A$ is the adsorbed guaiacol, $(\text{Product})_{ads}A$ is the adsorbed hydrogenated product. Scheme 2 below illustrates several reaction pathways in the hydrogenation and deoxygenation (e.g., demethoxylation) of guaiacol as an illustrative bio-oil constituent.

Scheme 2. Illustrative reactions between guaiacol, adsorbed hydrogen, and intermediate compounds (e.g., reactions between adsorbed guaiacol and adsorbed hydrogen, demethoxylation of guaiacol, hydrogenation of phenol to cyclohexanone and/or cyclohexanol, and desorption of the products).

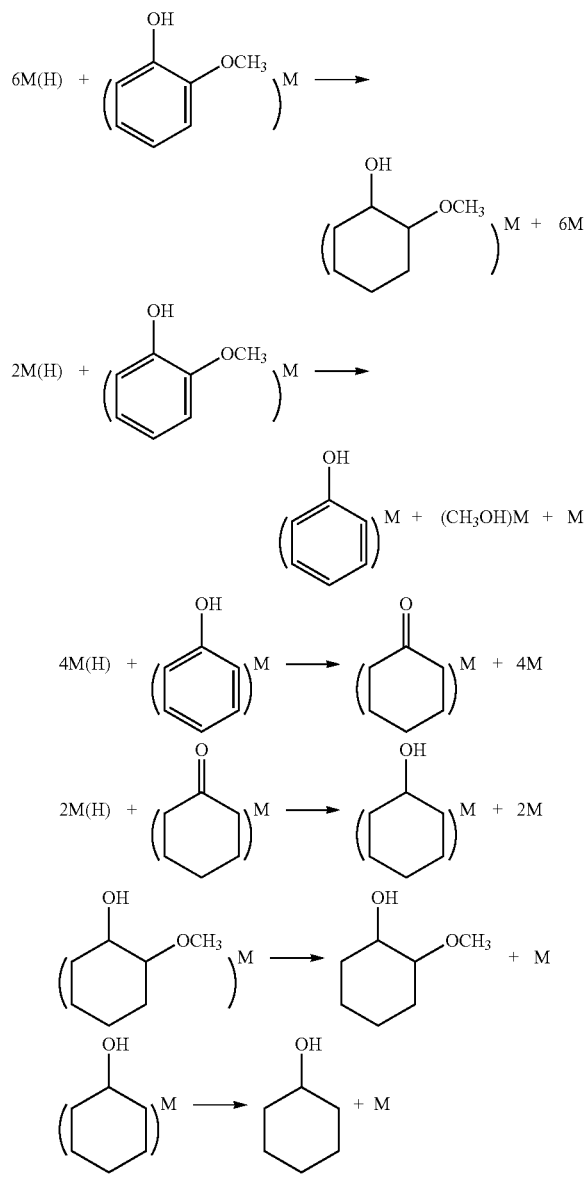

Besides the reactions listed above, hydrogen desorption via the Tafel (Eq. 8) or Heyrovsky (Eq. 9) processes competes with the desired hydrogenation (Eq. 6) negatively affecting its electrochemical efficiency (E.E.). As a practical matter, for bio-oil upgrading, this byproduct hydrogen could potentially be captured and used as a valuable reducing agent for further hydrotreatment.

$$(H)_{ads}M + (H)_{ads}M \rightarrow H_2 + 2M \quad (8)$$

$$(H)_{ads}M + (H^+)_{aq} + e^- \rightarrow H_2 + M \quad (9)$$

For supported metal catalysts, M refers to the metal active sites and A is the adsorbent support. The hydrogenation reaction happens at the adlineation point, the junction between these two sites. The rate of ECH is usually related to the area of the adlineation point. In order to maximize adlineation area, the metal (M) should have good electrical contact with the support. The Ru impregnated ACC cathode should be better in this way than the cathode formed by entrapping catalytic powder into RVC because the ruthenium is directly deposited on the support.

Control Experiments:

The first control experiment used only blank ACC as cathode material; at 80° C. and ambient pressure, it showed no hydrogenation of guaiacol. For this control experiment, there were no metal active sites for atomic hydrogen, and no catalyst for the hydrogenation reaction. Therefore, ACC alone cannot hydrogenate guaiacol.

The second control experiment used Ru/ACC-IW catalyst at 80° C. and ambient pressure, with no current passed. No guaiacol was converted, showing that hydrogen (e.g., generated by the current) is important for hydrogenation.

The third control experiment was performed on Ru/ACC, with no current passed through the electrochemical cell. However, $H_2$ gas was supplied by bubbling through the solution at 80° C. and ambient pressure. No conversion of guaiacol was observed either. Catalyst surface-bound atomic hydrogen forms differently in chemical catalytic hydrogenation (CH) vs. ECH. For ECH, atomic hydrogen directly forms on the cathode surface (Eq. 4), so even ambient pressure is enough. For CH, $H_2$ gas must dissolve first, but it is poorly soluble in water, so high pressure is usually needed for aqueous reactions. However, under the ambient pressure, the $H_2$ concentrations in solution and on the catalyst surface would be low. Furthermore, the temperatures used here are much lower than the 125° C. reported by Vispute as the lowest where guaiacol starts to be chemically reduced.

ECH of Guaiacol Using Different Catalysts: Preparation Methods and Precursors Effect:

ECH of guaiacol was studied with several different catalysts prepared using two methods (incipient wetness impregnation and cation exchange) with different precursors in various electrolytes and at various temperatures and currents (e.g., with 0.2 M HCl catholyte solution at 100 mA, 80° C., and ambient pressure being representative). The results are shown in Table 6 below.

TABLE 6

Conversion, electrochemical efficiency, and product selectivities for ECH of guaiacol at various conditions

| Catalyst | Temp. (° C.) | Elect. (0.2M) | Current (mA) | Conversion (%) | E.E. (%) | CH | Cis-2-MCH | Trans-2-MCH | P |
|---|---|---|---|---|---|---|---|---|---|
| 1 3-IW-Cl | 80 | HCl | 100 | 52 ± 0.4 | 10 ± 2.1 | 65 ± 7.1 | 31 ± 4.8 | 4.4 ± 2.3 | — |
| 2 3-IW-NH3 | 80 | HCl | 100 | 69 ± 1.3 | 31 ± 2.9 | 58 ± 3.1 | 25 ± 3.2 | 12 ± 0.3 | 3.7 ± 0.4 |

TABLE 6-continued

Conversion, electrochemical efficiency, and product selectivities for ECH of guaiacol at various conditions

| | | | | | | | Product selectivity (%) | | |
|---|---|---|---|---|---|---|---|---|---|
| Catalyst | Temp. (° C.) | Elect. (0.2M) | Current (mA) | Conversion (%) | E.E. (%) | CH | Cis-2-MCH | Trans-2-MCH | P |
| 3 5-IW-NH3 | 80 | HCl | 100 | 48 ± 8.7 | 19 ± 4.3 | 59 ± 11 | 29 ± 3.1 | 9.8 ± 6.4 | 2.4 ± 2.8 |
| 4 3-IW-NO | 80 | HCl | 100 | 38 ± 0.5 | 9.8 ± 0.5 | 47 ± 0.9 | 36 ± 0.0 | 12 ± 1.0 | 5.9 ± 0.1 |
| 5 5-IW-NO | 80 | HCl | 100 | 53 ± 1.6 | 19 ± 0.4 | 72 ± 1.3 | 22 ± 0.4 | 5.2 ± 0.8 | — |
| 6 1-CE-NH3 | 80 | HCl | 100 | 52 ± 6.2 | 19 ± 3.5 | 48 ± 2.3 | 37 ± 5.0 | 14 ± 2.7 | — |
| 7 3-CE-NH3 | 80 | HCl | 100 | 75 ± 3.9 | 30 ± 4.3 | 53 ± 1.4 | 36 ± 2.3 | 11 ± 2.0 | — |
| 8 3-IW-Cl | 25 | HCl | 100 | 13 ± 0.4 | 7.7 ± 1.8 | 26 ± 0.3 | 62 ± 6.5 | 12 ± 6.9 | — |
| 9 3-IW-Cl | 50 | HCl | 100 | 36 ± 12 | 17 ± 1.6 | 30 ± 1.4 | 56 ± 1.4 | 14 ± 0.0 | — |
| 10 1.5-CE-NH3 | 25 | HCl | 100 | 51 ± 0.8 | 19 ± 6.6 | 25 ± 8.4 | 59 ± 9.3 | 16 ± 0.9 | — |
| 11 1.5-CE-NH3 | 50 | HCl | 100 | 60 ± 13 | 31 ± 4.9 | 38 ± 0.5 | 47 ± 2.8 | 15 ± 2.2 | — |
| 12 3-CE-NH3 | 80 | NaCl | 100 | 64 ± 8.8 | 20 ± 2.2 | 42 ± 3.3 | 42 ± 1.3 | 17 ± 2.0 | — |
| 13 3-CE-NH3 | 80 | NaOH | 100 | 62 ± 2.4 | 28 ± 1.0 | 48 ± 0.2 | 38 ± 0.5 | 13 ± 0.6 | — |
| 14 3-IW-NH3 | 80 | NaOH | 100 | 45 ± 2.3 | 20 ± 1.2 | 46 ± 3.8 | 36 ± 2.3 | 11 ± 1.9 | 6.6 ± 0.4 |
| 15 3-IW-NH3 | 80 | HCl | 40 | 71 ± 3.3 | 27 ± 0.1 | 61 ± 1.9 | 28 ± 1.2 | 11 ± 0.7 | — |
| 16 3-IW-NH3 | 80 | HCl | 70 | 69 ± 0.0 | 28 ± 3.9 | 57 ± 0.5 | 30 ± 0.4 | 13 ± 0.1 | — |
| 17 3-IW-NH3 | 80 | HCl | 130 | 65 ± 4.2 | 23 ± 0.6 | 45 ± 1.3 | 38 ± 0.8 | 14 ± 0.5 | 2.1 ± 0.0 |
| 18 3-IW-NH3 | 80 | HCl | 160 | 60 ± <0.01 | 22 ± <0.01 | 49 ± <0.01 | 37 ± <0.01 | 14 ± <0.01 | — |

Figure 13:
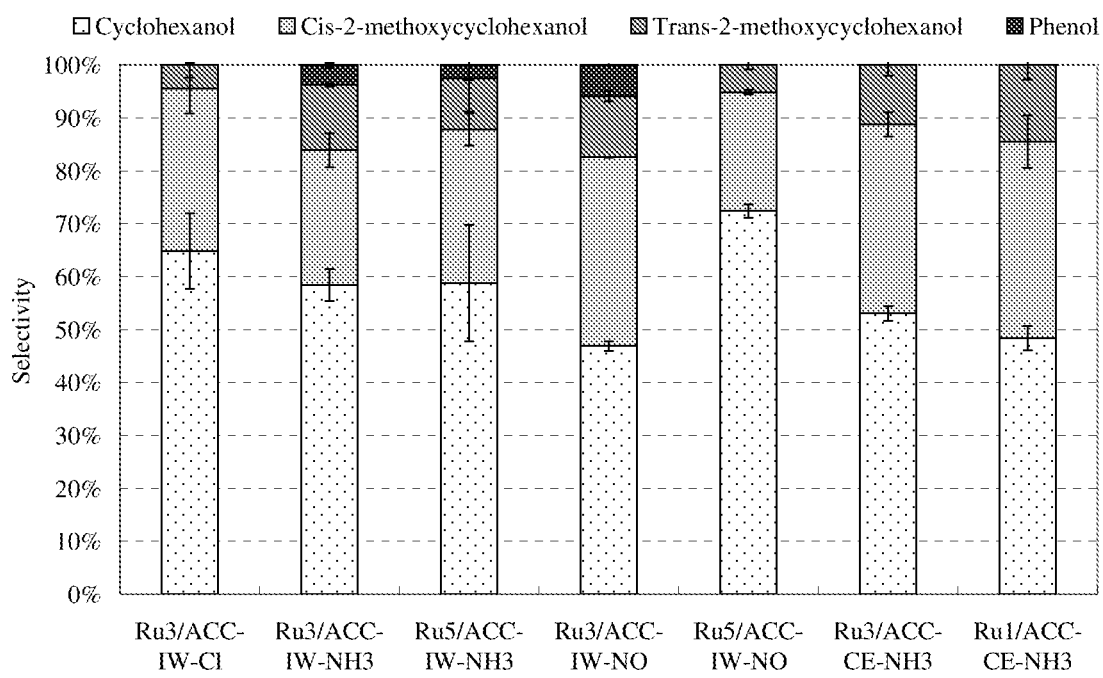
FIG. 13 illustrates products selectivity for ECH of guaiacol at 80° C. and ambient pressure using different catalysts with 0.2 M HCl as catholyte.

CH: cyclohexanol;
Cis-2-MCH: Cis-2-methoxycyclohexanol;
Trans-2-MCH: Trans-2-methoxycyclohexanol;
P: phenol Products detected using GC/MS include cyclohexanol, cis-2-methoxycyclohexanol, trans-2-methoxycyclohexanol and phenol (FIG. 13). However, phenol only appeared in measurable quantities with Ru3/ACC-IW-NH3, Ru5/ACC-IW-NH3 and Ru3/ACC-IW-NO as cathodes, indicating that most of the catalysts efficiently hydrogenated phenol. The reaction pathway for ECH of guaiacol to the major products is shown in Scheme 3. While demethylation is one of the major reactions in traditional catalytic deoxygenation of guaiacol, it is not observed during ECH; demethoxylation dominates instead. Thus ECH of bio-oil retains more carbon in the liquid products than conventional upgrading.

When catalysts with the same nominal ruthenium content (3 wt %) were compared, the Ru3/ACC-CE-NH3 catalyst gave a higher guaiacol conversion than the others (FIG. 14), suggesting that catalysts prepared by cation exchange were more active than those prepared using incipient wetness impregnation. Relatively uniform distribution (shown in FIG. 12) is one of the reasons for the good performance of cation exchange prepared catalysts. Furthermore, the pretreatment in the cation exchange method functionalizes the support surface by increasing acidic groups, which likely enhances guaiacol adsorption and thus, electrocatalytic activity.

Scheme 3. Reaction pathway for ECH of guaiacol to the major products; 2-methoxycyclohexanol includes both cis and trans isomers.

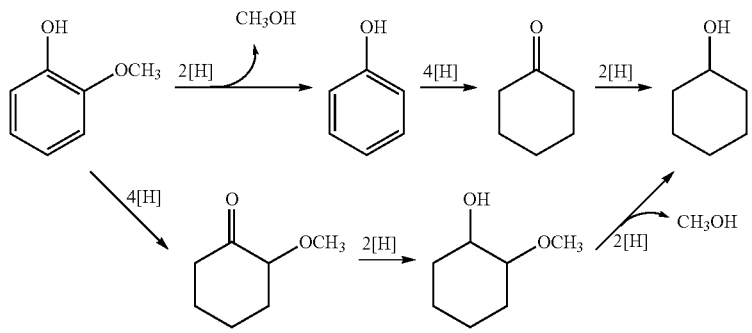

Deoxygenation of oxygenated compounds is one ultimate goal for bio-oil upgrading. Though deoxygenation is difficult at such mild conditions, partial deoxygenation of guaiacol was observed, resulting in two products, cyclohexanol and phenol. Cyclohexanol is a major product while phenol is only an intermediate. Among these catalysts, Ru5/ACC-IW-NO and Ru3/ACC-IW-Cl gave greater selectivity to cyclohexanol even though their activities toward guaiacol conversion are relatively low (FIG. 14).

Figure 15:
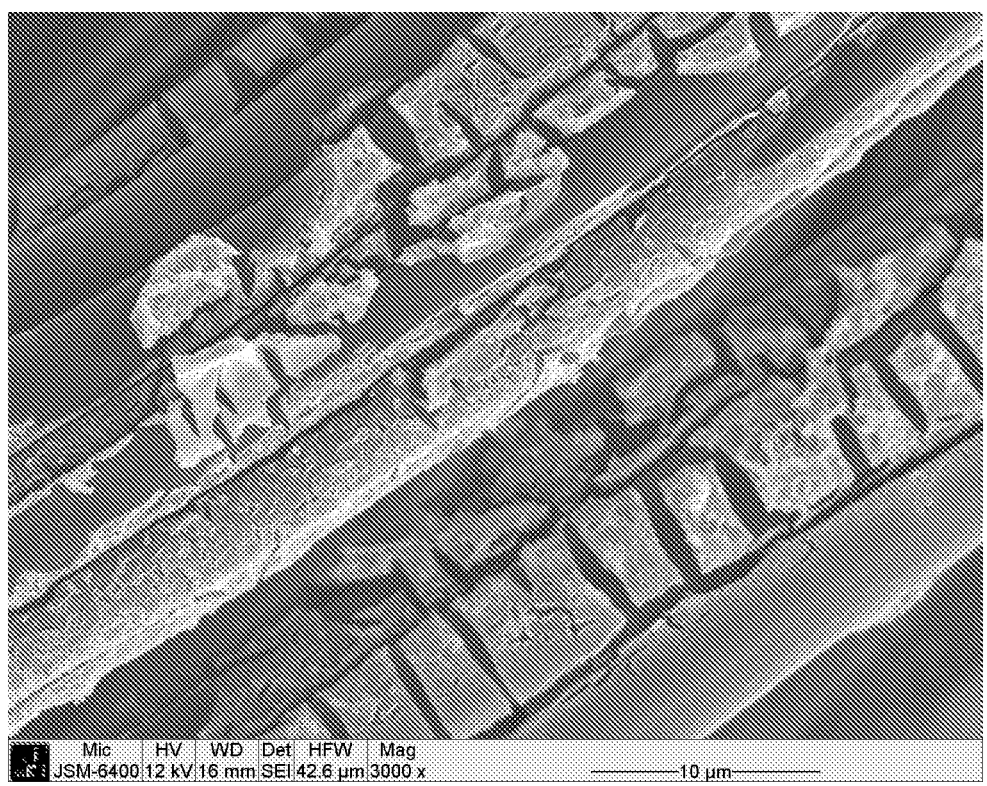
FIG. 15 illustrates ruthenium accumulation for the catalyst Ru3/ACC-IW-NO prepared with incipient wetness impregnation using $Ru(NO)(NO_3)_3$ as precursor. Scale bar: (a) 10 μm.

Ru/ACC catalysts prepared from different precursors using incipient wetness impregnation showed different activities toward ECH of guaiacol. The precursor Ru(NH$_3$)$_6$Cl$_3$ was the best one among the three precursors, followed by RuCl$_3$ and Ru(NO)(NO$_3$)$_3$. The presence of residual nitrogen on the catalyst and a poor ruthenium distribution could be two possible reasons for the worse performance of the catalyst prepared with Ru(NO)(NO$_3$)$_3$. As shown in FIG. 15, blocky accumulations of ruthenium can be observed, confirming the poor distribution with the precursor Ru(NO)

(NO$_3$)$_3$. Similarly, Nurunnabi et al. showed low CO conversion during Fischer-Tropsch synthesis with catalysts prepared from Ru(NO)(NO$_3$)$_3$. Diaz et al. also reported that Pd/C prepared with a nitrate precursor (Pd(NO$_3$)$_2$) showed a lower overall hydrogenation activity.

Figure 14:
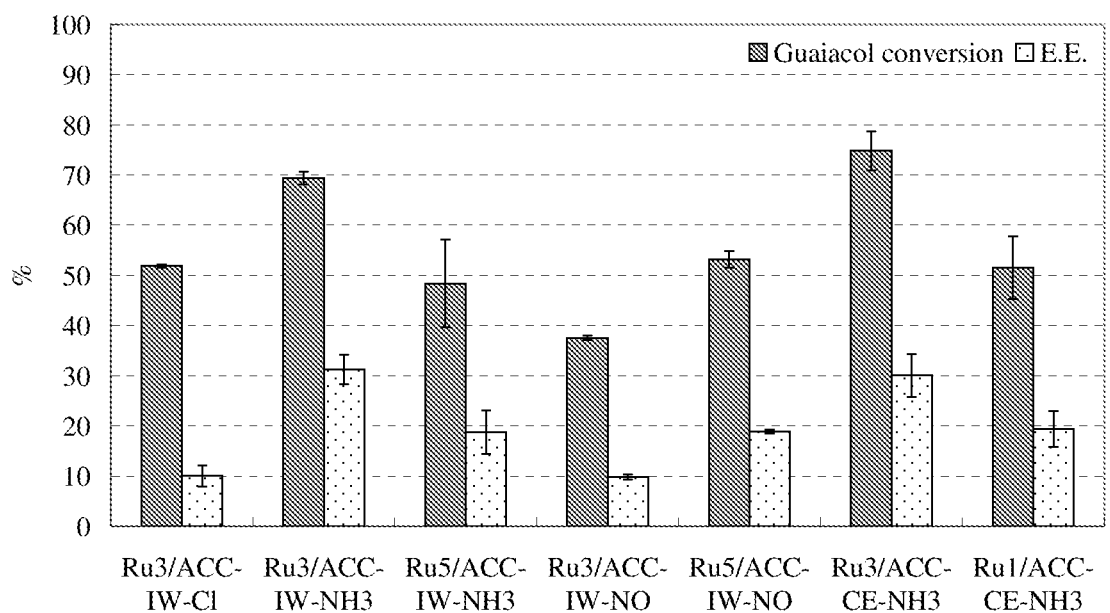
FIG. 14 illustrates guaiacol conversion and electrochemical efficiency for ECH of guaiacol at 80° C. using different catalysts.

The electrochemical efficiencies of guaiacol ECH at 80° C. using different catalysts were compared in FIG. 14. Both Ru3/ACC-IW-NH3 and Ru3/ACC-CE-NH3 catalysts show >30% electrochemical efficiency, higher than the 26.3% maximum reported E.E. for phenol ECH, obtained using a Pd catalyst. One possible reason is that the present immobilization schemes achieve more intimate metal-support electrical contact, creating larger adlineation regions and therefore, improved electrochemical efficiency.

Temperature Effect:

The effect of temperature on guaiacol ECH was studied with 0.2 M HCl as catholyte for 2 hr under a constant current of 100 mA. Three different temperatures, 25, 50 and 80° C., were studied, all much lower than those used in classical catalytic conversion of phenolic compounds.

As temperature rises, both electrocatalytic hydrogenation and hydrogen desorption should accelerate. The competition between these two reactions determines the E.E. Raising the temperature from 25° C. to 50° C. increased E.E (FIG. 16) from 8% to 17% but further heating to 80° C. dropped it back to 10%. Similar E.E. changes on the ECH of indigo to leuco indigo were observed by Roessler et al., who found that E.E rose as temperature was ramped up from 30° C. to 60-80° C., but then dropped off above this range. On the other hand, Dabo et al. found continuous E.E. improvement from 25° C. to 75° C. during ECH of 4-phenoxyphenol to phenol over 5% Pd/C in 1 M NaOH. Amouzegar and Savadogo also saw continuous E.E. increases from 5 to 40 to 60° C. during ECH of phenol to cyclohexanol on platinum dispersed on graphite particles; the E.E. increase from 40° C. to 60° C., however, was much smaller than that from 5° C. to 40° C.

Figure 16:
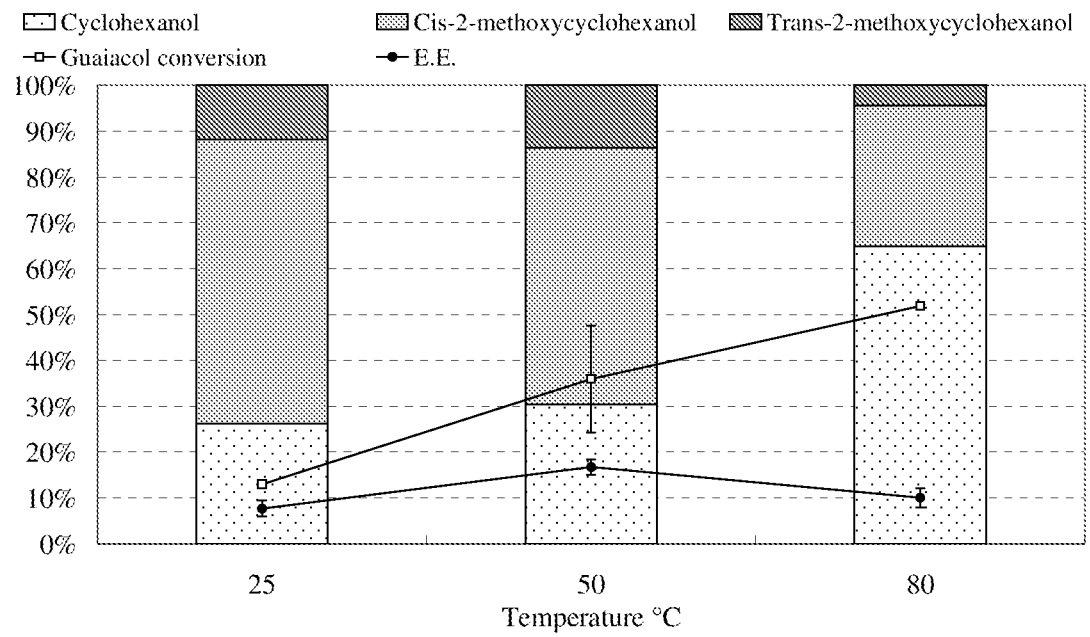
FIG. 16 illustrates products distribution, guaiacol conversion and E.E. for ECH of guaiacol at different temperatures using Ru3/ACC-IW-CI.
Figure 17:
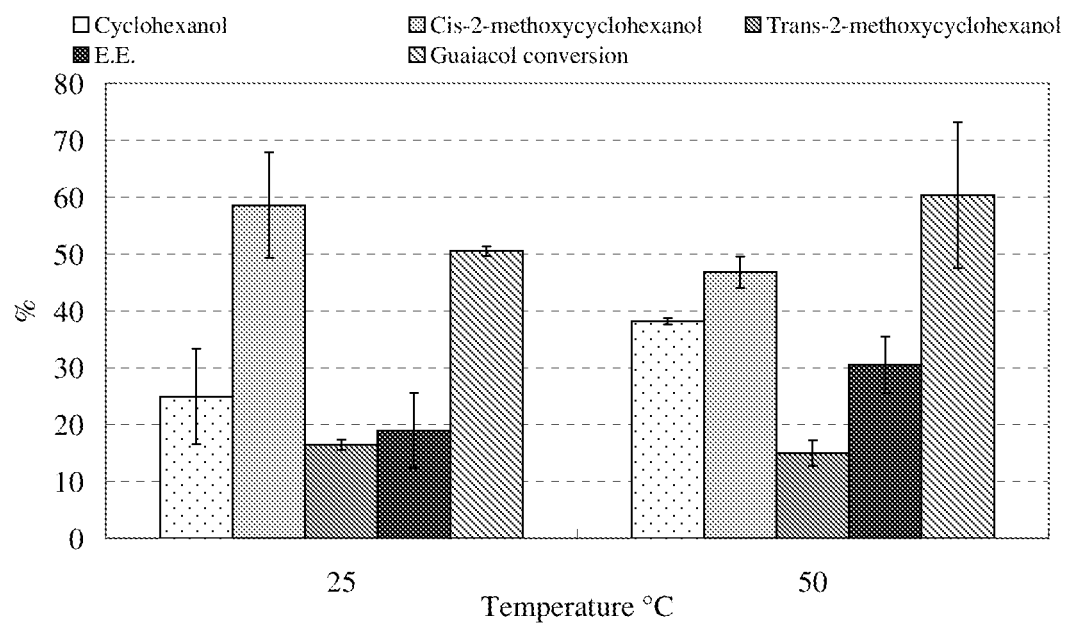
FIG. 17 illustrates products distribution, guaiacol conversion and E.E. for ECH of guaiacol at different temperatures using Ru1.5/ACC-CE-NH3.

Cation exchange prepared catalyst shows good activity toward guaiacol conversion at 25° C., very similar to that at 50° C. (FIG. 17). However, guaiacol conversion for incipient wetness impregnation prepared catalyst decreased dramatically from 36% to 13% (FIG. 16). Again, catalysts prepared by cation exchange show better performance than those prepared by incipient wetness impregnation.

The effect of temperature on the product selectivities using Ru3/ACC-IW-Cl was shown in FIG. 16. At 80° C., cyclohexanol was the dominant product, while cis-2-methoxycyclohexanol became the largest one at 25° C. and 50° C. As temperature increased, the demethoxylation of guaiacol to cyclohexanol was likewise increased. Though trans-2-methoxycyclohexanol isomer was expected to be more stable, the cis isomer was always the major product at these studied temperatures. Presumably, during hydrogenation, the aromatic ring is parallel with the ruthenium active surface and atomic hydrogens are added to the one face, thus forming cis-2-methoxyclohexanol. This phenomenon was also observed when using catalyst prepared by the cation exchange method (FIG. 17). Solladié-Cavallo et al. showed a similar result for hydrogenation of substituted phenols over Ru/Al$_2$O$_3$.

Figure 18:
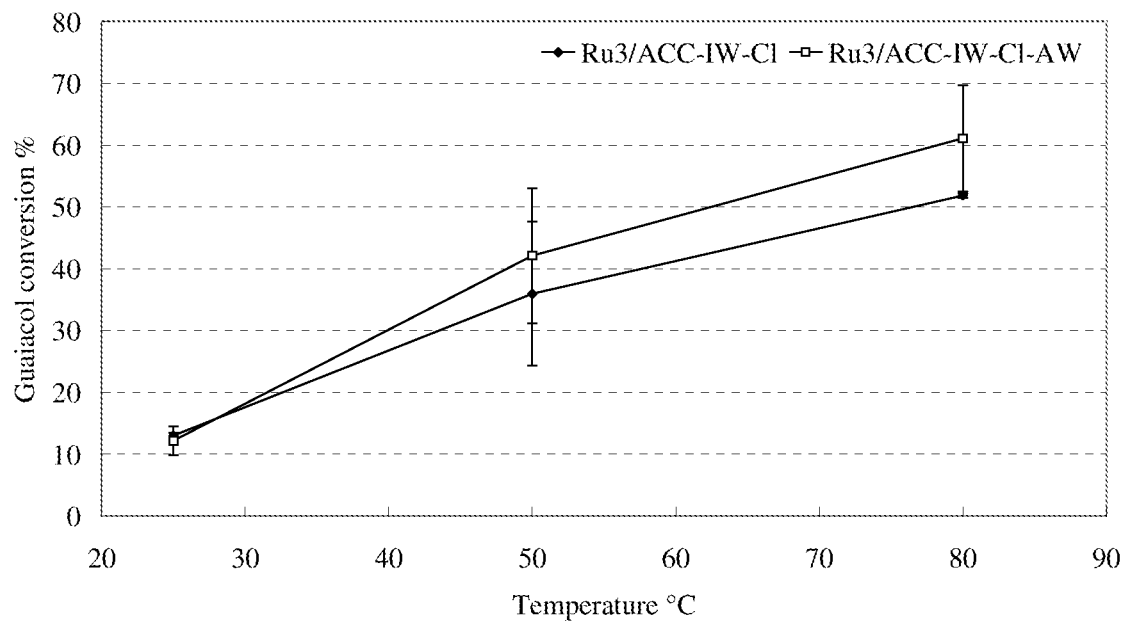
FIG. 18 illustrates ECH of guaiacol using catalysts prepared on HCl washed ACC (Ru3/ACC-IW-CI-AW) and original ACC (Ru3/ACC-IW-CI) with 0.2 M HCl as electrolyte at different temperatures.
Figure 19:
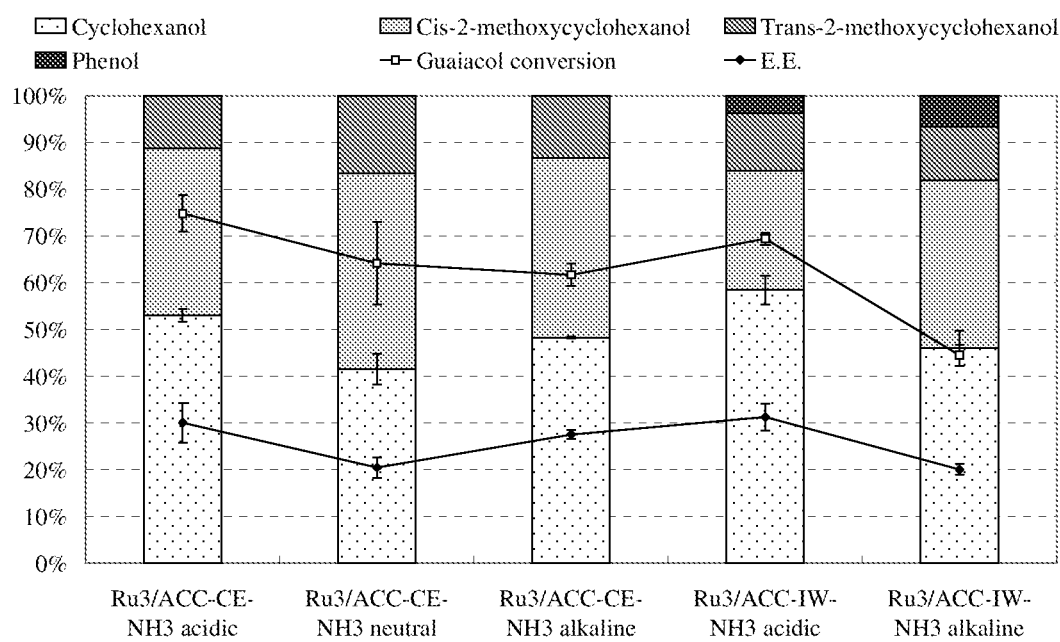
FIG. 19 illustrates ECH of guaiacol using catalysts Ru3/ACC-CE-NH3 and Ru3/ACC-IW-NH3 under different pH conditions. Bars refer to product selectivity.

Catalyst Support Effect:

The EDX result shows that there are other elements in the original ACC besides C and O, including Al, Zn and S (Table 4). Some elements, especially S, may have strong chemisorption with ruthenium, blocking the active sites and moderating the hydrogenation reaction. Thus, catalyst performance was assessed based on original and demineralized ACC. ACC was demineralized by washing in boiling hydrochloric acid for 3 days, resulting in the decrease of the ash content from 5 wt % to around 0.1 wt %. The performance of the catalysts made from these two ACC supports was compared with each other during ECH of guaiacol using 0.2 M HCl as catholyte at three different temperatures, 25, 50 and 80° C. (FIG. 18). The activities of these two catalysts are not significantly different from each other at 25, 50 and 80° C., suggesting that the elements in the original ACC do not have any significant effect on the catalyst activity.

pH Effect:

All previous experiments were carried out in 0.2 M HCl solution. The performance of these catalysts in neutral (0.2 M NaCl as catholyte) and basic solution (0.2 M NaOH as catholyte) was examined here. All the other conditions were the same as the run with 0.2 M HCl as electrolyte. When using Ru3/ACC-CE-NH3 and Ru3/ACC-IW-NH3 as catalysts, guaiacol conversion was favored under acidic conditions (FIG. 19). Guaiacol adsorption onto the carbon support (Eq. 5) is important for the hydrogenation reaction (Eq. 6). pH will influence the nature of guaiacol molecules (ionic or not) in the solution, thus affecting the adsorption onto the carbon support. In acidic and neutral conditions, guaiacol (pKa=9.9) is mainly a neutral molecule, while deprotonation of guaiacol to form phenolate anion occurs under alkaline conditions. The anion form is more favored in the polar solution and the adsorption onto the carbon support is small, while neutral molecules are more easily adsorbed onto the carbon support. Furthermore, the phenolate form enhances the resonance structure, making the ECH of guaiacol more difficult. Thus a better guaiacol conversion was observed in acidic than in alkaline solution. A similar effect on E.E. was observed, showing a higher E.E. in the acidic conditions. Likewise, selectivity of cyclohexanol was higher under acidic conditions, indicating a higher level of demethoxylation of guaiacol (FIG. 19).

Figure 20:
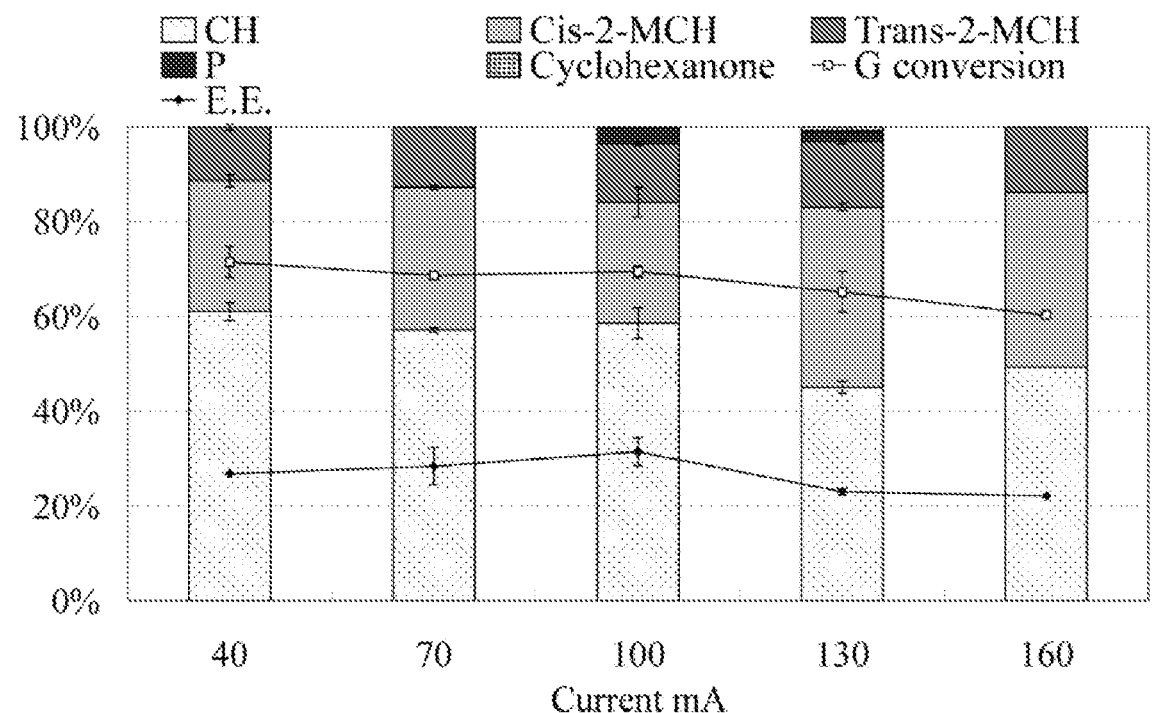
FIG. 20 illustrates ECH of guaiacol using the catalyst Ru3/ACC-IW-NH3 under different currents at 80° C. and ambient pressure. Bars refer to product selectivities.

Current Density Effect:

Current density effects on guaiacol conversion, electrochemical efficiency and product selectivities were studied for guaiacol ECH at 80° C. and ambient pressure with 0.2 M HCl as catholyte. Because it was difficult to measure the actual effective electrode surface area, current is directly used without calculating current density. As shown in FIG. 20, guaiacol conversion and electrochemical efficiency are invariant when current is in the range of 40 mA to 100 mA and above 100 mA, both decrease slightly. The current density effect on guaiacol conversion and E.E. is not very obvious for ECH of guaiacol using Ru/ACC as cathode because the surface area of the cathode is relatively high and the absolute change of the current density is very small. Additionally, product selectivities are only slightly affected. Selectivity for cyclohexanol formation is higher for the current range from 40 mA to 100 mA than 130 mA and 160 mA.

ECH of Other Phenolic Compounds: Phenol and Syringol:

Besides guaiacols, other two phenolic compounds derived from lignin were used as model compounds, phenol and syringol. ECH of these two model compounds was carried out in 0.2 M HCl catholyte solution at 80° C. and ambient pressure. ECH of phenol generates two products, cyclohexanol and cyclohexanone (Table 7). Cyclohexanol is the major product, indicating the reaction from cyclohexanone to cyclohexanol is fast. Five major products are obtained for ECH of syringol, including cyclohexanol, cis-2-methoxycyclohexanol, trans-2-methoxycyclohexanol, 2-methoxycyclohexanone and guaiacol (Table 7); these products are similar to those obtained from ECH of guaiacol and point to demethoxylation as the first step from syringol.

Equal amounts of charge were passed for ECH of phenol and syringol, but ECH of phenol requires less electrons than ECH of syringol, resulting in higher conversion of phenol. The π-system's electron density increases as the methoxylation degree increases from phenol to syringol, so syringol should be more difficult to reduce. However, similar E.E. values were obtained for ECH of both model compounds.

resulted in higher guaiacol conversion and electrochemical efficiencies. Furthermore, phenol and syringol can also be hydrogenated using Ru/ACC catalyst, showing similar electrochemical efficiencies. Based on the results shown in this investigation, electrocatalytic hydrogenation with Ru/ACC provides a good tool for ambient pressure hydrogenation of phenolic compounds at low temperatures, and it may offer significant advantages for future bio-oil stabilization and upgrading.

TABLE 7

ECH of phenol and syringol using Ru1.5/ACC—CE—NH3 at 80° C. and ambient pressure with 0.2M HCl as catholyte

| Reactants | Conversion % | E.E. % | Product selectivity % | | | | | |
|---|---|---|---|---|---|---|---|---|
| | | | Cyclohexanol | Cyclohexanone | Cis-2-methoxy-cyclohexanol | Trans-2-methoxy-cyclohexanol | 2-methoxy-cyclohexanone | Guaiacol |
| Phenol | 89 | 29 | 99 | 0.5 | — | — | — | — |
| Syringol | 58 | 29 | 35 | 0 | 27 | 9 | 13 | 16 |

Figure 21:
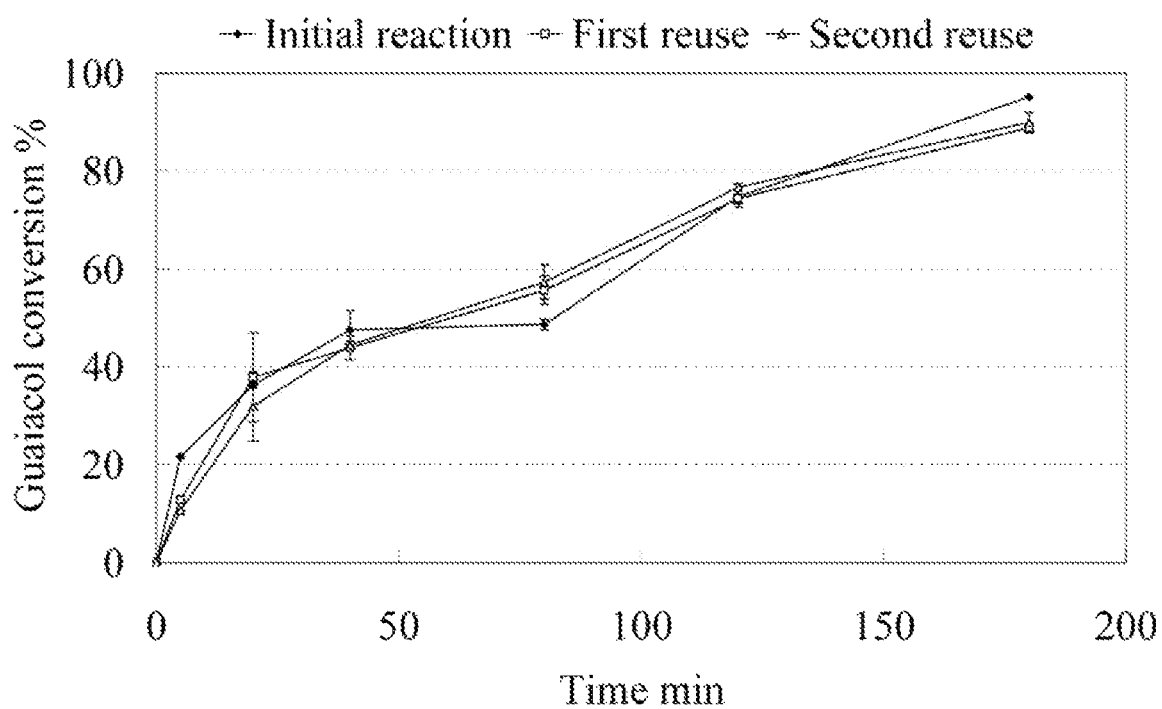
FIG. 21 illustrates the time course of guaiacol conversion for the initial reaction, the first reuse, and the second reuse of the catalyst Ru3/ACC-IW-NH3 using 0.2 M HCl as the catholyte at 80° C. and ambient pressure.

Catalyst Stability:

Catalyst deactivation is an important concern during catalytic bio-oil upgrading. To evaluate the catalyst stability during ECH of phenolic compounds, the catalysts were reused two times. After each use of the catalytic cathode, it was washed overnight using DI water, followed by drying under vacuum in the dessicator. At the beginning of the next experiment, pre-electrolysis was carried out at 80 mA for 10 min. As shown in FIG. 21, guaiacol conversion did not change significantly with each reuse of the catalyst. Also, ICP-OES analysis of the solution showed that there was no significant ruthenium leaching into the solution. This observed stability of the Ru/ACC catalytic cathode is likely due to the mild conditions required for effective ECH of guaiacol.

This example shows that Ru/ACC is an efficient catalyst for electrocatalytic hydrogenation and partial hydrodeoxygenation of phenolic compounds under mild conditions compared to other catalytic reductions, including other ECH schemes. Catalyst comparisons demonstrated that Ru/ACC catalysts prepared via the cation exchange method show much better activity than those prepared by incipient wetness impregnation. When using incipient wetness impregnation, $Ru(NH_3)_6Cl_3$ was shown to be the best precursor among those three precursors. Higher temperature was found to favor the guaiacol conversion and deoxygenation within the temperature range, 25 to 80° C. Lower pH Example 3

ECH/ECHDO Treatment of Water-Soluble Bio-Oil Components (Switchgrass)

Figure 22:
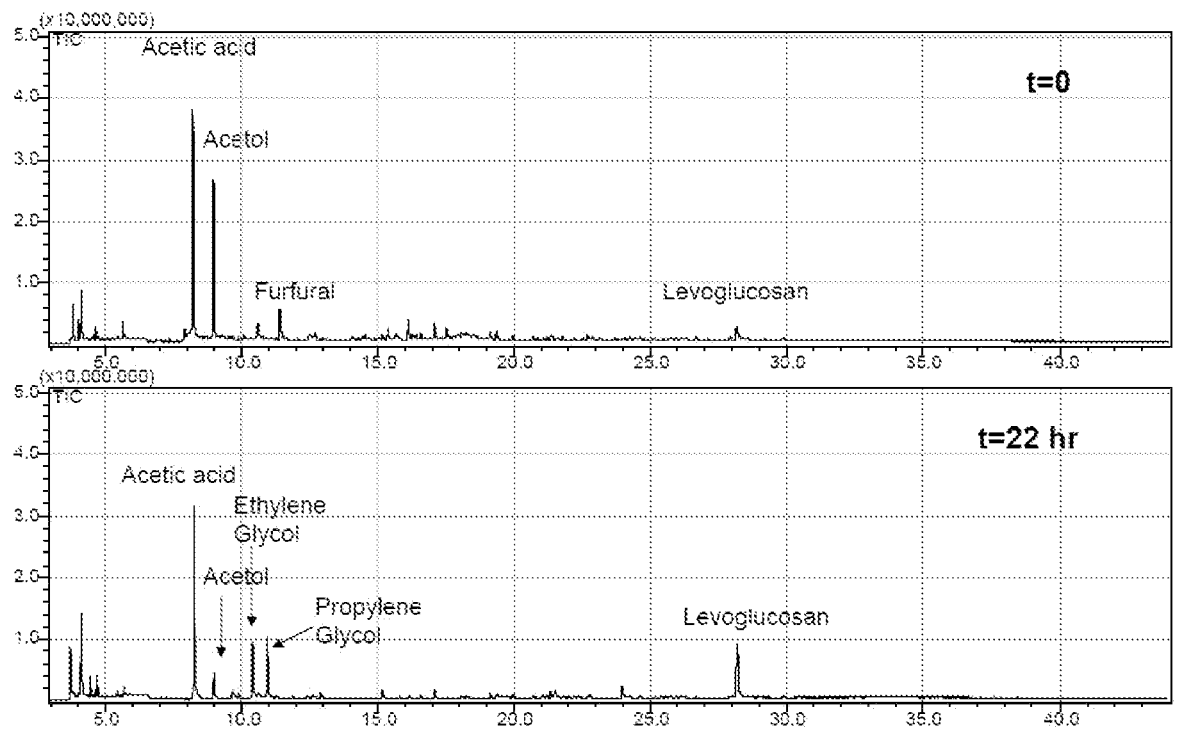
FIG. 22 is a GC/MS total ion chromatogram for various water-soluble bio-oil components and related ECH products in an initial reaction mixture (t=0 hr) and in a subsequent post-ECH reaction mixture (t=22 hr).

Example 3 illustrates the method of Example 2 using a Ru/ACC catalyst to perform ECH/ECHDO on a mixture of organic reactants. The reactant mixture was obtained as a water-soluble fraction of a bio-oil mixture containing a variety of aldehydes, ketones, carboxylic acids, and phenolic compounds (Table 8). Specifically, switchgrass-derived bio-oil (40 g) was mixed with 400 mL DI water to separate bio-oil into water-soluble and water-insoluble fractions. The water-soluble fraction was obtained by centrifuging the mixture, followed by decanting. A divided electrochemical cell (illustrated in FIG. 2) was used, with Ru5/ACC-IW-NH3 as the cathode and Pt wire as the anode. Ammonium chloride (0.2 M) and phosphate buffer (0.2 M, pH=7) were used as electrolytes for the cathode solution and the anode solution, respectively. The ECH was carried out under constant current (100 mA), at room temperature and ambient pressure. Because bio-oil may undergo polymerization even at this mild condition, a control experiment without passing current was performed to check any changes. The reaction mixture was analyzed via GC/MS (FIG. 22) both at t=0 hr and t=22 hr (also including the control sample). The results (Table 8) indicate that a broad spectrum of bio-oil components having a variety of functional groups were converted (some with essentially complete conversion) to a variety of corresponding reaction products.

TABLE 8

GC/MS Analysis Data of Water-soluble Bio-Oil Constituents and Related Products

| | | Reactants | | |
|---|---|---|---|---|
| Retention Time | | Experimental Component Peak Area (Area %) for ECH Process | | Control (No ECH) |
| (min) | Reactant | t = 0 Hr | t = 22 Hr | t = 22 Hr |
| 4.608 | Propanal | 1117903 (0.21%) | 0 | 2953459 (0.6%) |
| 4.693 | Acetone | 6020431 (1.15%) | 0 | 5294849 (1.07%) |
| 5.686 | 2,3-butanedione | 9534347 (1.81%) | 0 | 10848505 (2.19%) |
| 7.637 | Formic acid | 18980476 (3.62%) | 0 | 19009901 (3.83%) |
| 7.989 | Acetic acid | 128271648 (24.43%) | 44915235 (12.91%) | 110080349 (22.18%) |
| 9.151 | Propanoic Acid | 4001867 (0.76%) | 3697466 (1.06%) | 2194006 (0.44%) |

TABLE 8-continued

GC/MS Analysis Data of Water-soluble Bio-Oil Constituents and Related Products

| 8.768 | Acetol | 81865075 (15.6%) | 9461220 (2.72%) | 18562247 (3.74%) |
|---|---|---|---|---|
| 9.913 | Cyclopentanone | 874482 (0.17%) | 0 | 0 |
| 11.439 | Furfural | 17429573 (3.32%) | 0 | 11466012 (2.31%) |
| 10.486 | 1-Hydroxy-2-butanone | 19758760 (3.77%) | 3590189 (1.03%) | 0 |
| 15.348 | 2-furanone | 7133361 (1.36%) | 0 | 6626809 (1.34%) |
| 16.562 | Phenol | 3439913 (0.66%) | 1903118 (0.55%) | 2358872 (0.48%) |
| 17.082 | Guaiacol | 7638668 (1.46%) | 3642669 (1.05%) | 5046089 (1.02%) |
| 22.696 | Syringol | 2145082 (0.41%) | 988114 (0.28%) | 0 |
| 28.139 | Levoglucosan | 13258515 (2.35%) | 51841305 (14.89%) | 31319367 (6.32%) |

Products

| Retention Time | | Experimental Component Peak Area (Area %) for ECH Process | | Control (No ECH) |
|---|---|---|---|---|
| (min) | Product | t = 0 Hr | t = 22 Hr | t = 22 Hr |
| 4.65 | Isopropanol | 0 | 1432356 (0.41%) | 0 |
| 8.822 | 3-hydroxy-2-butanone | 0 | 1093524 (0.31%) | 0 |
| 10.241 | Ethylene glycol | 8950659 (1.71%) | 30229578 (8.69%) | 9351530 (1.89%) |
| 10.555 | Propylene glycol | 0 | 29665576 (8.53%) | 0 |
| 9.608 | Cyclopentanol | 0 | 853278 (0.25%) | 0 |
| 12.395 | Furfuryl alcohol | 0 | 1186281 (0.34%) | 0 |
| 5.743 | Tetrahydrofuran | 0 | 4018440 (1.16%) | 0 |
| 12.742 | 1,2-butanediol | 0 | 2586592 (0.74%) | 0 |
| 15.128 | Butyrolactone | 3037099 (0.58%) | 4753266 (1.37%) | 2373182 (0.48%) |

Example 4

ECH/ECHDO Treatment of Water-Soluble Bio-Oil Components (Poplar)

Similar to Examples 2 and 3, electrocatalytic hydrogenation (ECH) was used for bio-oil stabilization and upgrading. Water-soluble bio-oil, as generated by water separation, was hydrogenated using ECH under room temperature and ambient pressure. Ruthenium supported on activated carbon cloth was used as the cathode electrocatalyst. After electrocatalytic hydrogenation, most of the aldehydes and ketones were hydrogenated to the corresponding alcohols or diols, which were thermochemically more stable. Carbon recovery into the liquid product was more than 80%, and less than 0.1 wt % solid of the water-soluble bio-oil was formed during ECH. An accelerated aging test was performed to evaluate the stability of ECH treated water-soluble bio-oil. Size exclusion chromatography (SEC) and viscosity measurements were used to analyze the aged bio-oil. SEC analysis indicated that ECH treated bio-oil was more stable than that without ECH treatment. Besides stabilization of the bio-oil, valuable products, such as hydrogen and diols, can be recovered during electrocatalytic hydrogenation.

Fast pyrolysis is a thermochemical method for converting biomass into a liquid product, known as bio-oil. Because bio-oil has a much higher bulk density than the original biomass, fast pyrolysis becomes an effective way to densify biomass. Locating this technology in the regional biomass pyrolysis depots (RBPDs), near the biomass harvesting area, can potentially reduce the cost of biomass transportation to the central refinery. However, high concentrations of carboxylic acids, mainly formic acid and acetic acid, make the bio-oil very corrosive to metal storage containers and pipes. Chemical instability of bio-oil poses another barrier to this approach as reactive carbonyl compounds (aldehydes and ketones) in bio-oil readily undergo polymerization. To reduce the corrosiveness and improve the chemical stability, stabilization or mild upgrading is required before transporting bio-oil to the central refinery.

To facilitate fast pyrolysis implementation in the RBPDs, stabilization techniques that can be supported at small scales are desirable. Bio-oil upgrading with hydrotreatment is not economically practical at small and medium scales, in part due to the lack of the available hydrogen at RBPDs. Thus a new method with an alternative reducing agent is required to stabilize the bio-oil in the regional biomass processing depots. In this context, the use of electrocatalytic hydrogenation (ECH) is applied to stabilize and/or partially upgrade bio-oil. Instead of molecular hydrogen, electricity produced from renewable sources, such as photovoltaic cells or wind turbines, is used as the reducing agent. Atomic hydrogen is produced in situ on the catalytic electrode surface and reacts with the organic compounds absorbed on the catalyst surface. The surface hydrogen atom concentration is controlled by the applied electrode potential, so the reaction can take place at very mild conditions, such as ambient pressure and temperature. Furthermore, the catalyst is heterogeneous and monolithic, so elaborate and expensive catalyst recovery is not required.

In this example, water-soluble bio-oil was investigated as it contains most of the carboxylic acids and carbonyl groups in raw bio-oil. This bio-oil fraction is very difficult to upgrade using traditional hydrotreatment since water is detrimental to most catalysts at high temperatures. Several characteristics of the bio-oil, before and after electrocatalytic hydrogenation, were measured by various characterization methods, including GC/MS, size exclusion chromatography (SEC,) and total organic carbon (TOC) analysis. Accelerated aging studies also were performed to evaluate the stability of water-soluble bio-oil before and after ECH treatment. SEC and viscosity measurements also were employed to characterize the bio-oil after the aging test. Electrochemical efficiency was calculated using the measured hydrogen generation and improvement of the electrochemical efficiency was carried out by adding surfactant into the bio-oil.

Bio-Oil:

Bio-oil was obtained by pyrolyzing poplar DN34 in a bench-scale screw-conveyor fast pyrolysis reactor. The bio-oil was stored at −3° C. in the refrigerator immediately after its production. Major elements and bulk properties are shown in Table 9, and representative abundant chemical compounds in bio-oil are shown in Table 10.

TABLE 9

Properties of bio-oil derived from fast pyrolysis of poplar DN34

| Property | Value |
|---|---|
| Carbon Content | 34.3 wt. % |
| Hydrogen Content | 8.2 wt. % |
| Oxygen Content | 57.5 wt. % |
| Nitrogen Content | <0.01 wt. % |
| Solids (methanol insoluble) | 0.7 wt. % |
| Water Content | 36.6 wt. % |
| pH | 2.8 |
| Density | 1.12 g/mL |

TABLE 10

Quantification of representative bio-oil components with GC/MS and HPLC

| Bio Oil Component | Group | Method | wt % in whole bio-oil |
|---|---|---|---|
| Cellulose/hemicellulose-derived compounds | | | |
| Acetic acid | Acids | GC/MS | 6.2 |
| Acetol | Misc. Oxygenates | GC/MS | 5.6 |
| 1-Hydroxy-2-butanone | Misc. Oxygenates | GC/MS | 3.1 |
| Furfural | Furans | GC/MS | 0.4 |
| Furfuryl alcohol | Furans | GC/MS | 0.3 |
| Cyclopentanone | Ketones | GC/MS | 0.3 |
| 3-Methyl-2-cyclopentenone | Ketones | GC/MS | 0.4 |
| 3-Methyl-1,2-cyclopentanedione | Ketones | GC/MS | 1.1 |
| Levoglucosan | Sugars | GC/MS | 3 |
| Glucose | Sugars | HPLC | 0.3 |
| Xylose | Sugars | HPLC | 0.3 |
| Lignin derived compounds | | | |
| Phenol | Phenols | GC/MS | 1 |
| 2-Methylphenol | Phenols | GC/MS | 0.3 |
| Guaiacol | Phenols | GC/MS | 0.5 |
| Cresol | Phenols | GC/MS | 0.5 |
| 4-Ethyl-guaiacol | Phenols | GC/MS | 0.4 |
| Eugenol | Phenols | GC/MS | 0.2 |
| Isoeugenol | Phenols | GC/MS | 1.2 |
| Methoxyeugenol | Phenols | GC/MS | 2.3 |
| Syringol | Phenols | GC/MS | 1.4 |

Water-Soluble Bio-Oil:

Water-soluble bio-oil was obtained by mixing/extracting bio-oil with water, followed by 30 minutes of sonication. The mixture was then centrifuged and the top layer decanted to use as the water-soluble bio-oil fraction. Before each experiment, the water-soluble bio-oil was filtered through a 0.22 μm syringe filter.

Figure 23:
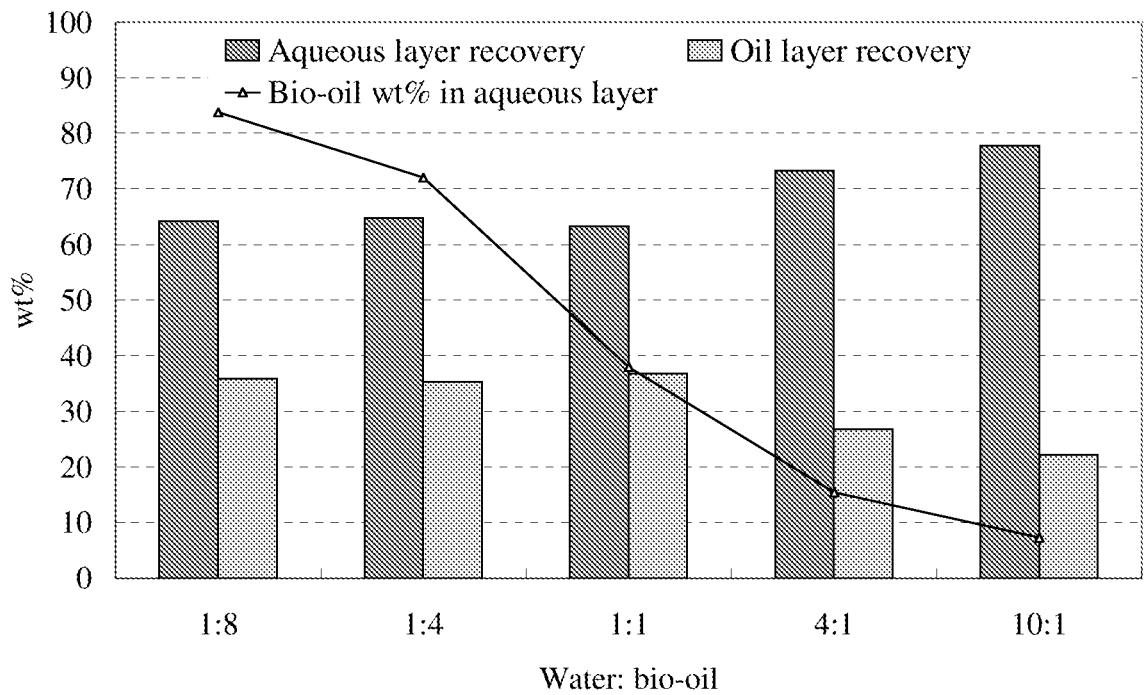
FIG. 23 is a graph illustrating the separation/extraction efficiency of bio-oil using water with different water:bio-oil ratios.

The water-to-bio-oil ratio influences phase separation and organic compound recovery in the aqueous phase. At water:bio-oil ratios of about 1:10 or lower, there was no phase separation. As shown in FIG. 23, when the ratio increased to 1:8, phase separation was observed. As the amount of water increased, more bio-oil is recovered in the aqueous layer. However, the final bio-oil concentration in the aqueous layer decreases due to dilution. Unless otherwise stated, a water:bio-oil ratio at 4:1 was used for extractions in this example, with the final bio-oil concentration at 15 wt %. To reduce the electrocatalytic hydrogenation reaction time, a two-fold dilution of water-soluble bio-oil was performed to produce the water-soluble bio-oil used for the following experiments.

The selected 4:1 ratio is illustrative, and the chemistry for ECH of the water-soluble bio-oil can be performed on a more concentrated water-soluble bio-oil fraction with lower water content, for example with a water:bio-oil ratio as low as about 1:8.

Catalyst Preparation:

A piece of activated carbon cloth (ACC) (1.3 cm×3.0 cm) was first soaked into $Ru(NH_3)_6Cl_3$ solution, which was enough to saturate the ACC pores. After the ACC pores were saturated with the solution, it was removed and dried off using KIMWIPES. The damp ACC was then dried on the benchtop and further dried under vacuum at room temperature. Finally, the impregnated ACC was reduced with $H_2$ in a Parr pressure reactor (model 452HC) at 500 psi and 220° C. The catalyst is referred to as Ru3/ACC-IW-NH3, where "Ru3" represents a nominal ruthenium content of 3 wt, %, "IW" stands for incipient wetness impregnation, and "NH3" means the precursor is $Ru(NH_3)_6Cl_3$.

Figure 24:
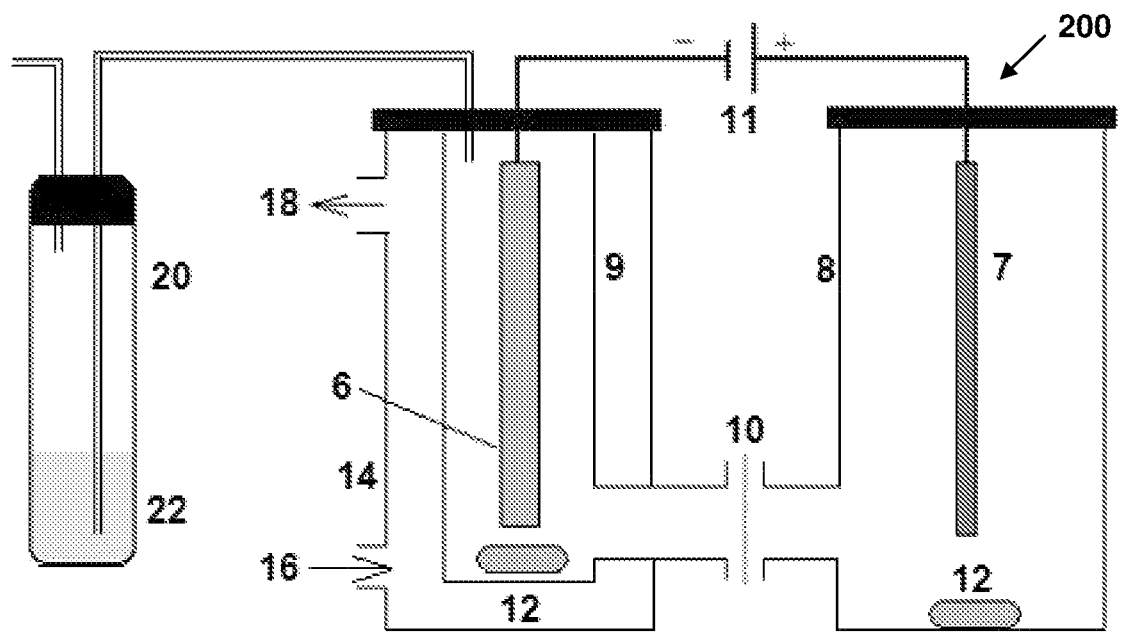
FIG. 24 illustrates a divided electrochemical cell 200 similar to that of FIG. 2 and according to an additional embodiment additionally including a reaction cooling jacket 14 and product recovery trap 20.

Electrochemical Cell:

With reference to FIG. 24, electrochemical hydrogenation of the water-soluble bio-oil was carried out in a two-chamber 8,9 glass H-cell, separated with a NAFION-117 membrane 10 (a sulfonated tetrafluoroethylene-based fluoropolymer-copolymer available from DuPont). Due to resistance heating as current passes through the electrolyte solution in the cathode chamber 9, a water jacket 14 with a water inlet 16 and a water outlet 18 was used to cool the cathode chamber 9. Water-soluble bio-oil with 0.2 M NaCl served as the cathode electrolyte (catholyte), while Ru3/ACC-IW-NH3 was used as the working electrode 6 (cathode). Anolyte (30 mL) in the anode chamber 8 consisted of 1 M sulfuric acid, and a Pt wire was used as the counter electrode 7 (anode). ECH was carried out under galvanostatic control (480 mA) for 6.5 hr with an Instek GPR-11H30D DC power supply. Organic compounds that were stripped from the catholyte by bubbling hydrogen gas were captured in de-ionized water 22 of a water trap 20.

Pyroprobe-GC/MS Analysis:

Analytical pyrolysis experiments were conducted using a microscale pyrolysis unit, CDS PYROPROBE 5250 (CDS Analytical Inc., Oxford, Pa.) interfaced to a SHIMADZU QP-5050A gas chromatograph/mass spectrometer (GC/MS) (Shimadzu Corp., Columbia, Md.). Approximately 0.5 mg of ground biomass sample was packed between quartz wool in a quartz tube with a filler rod. Three replicates of each sample were run. The pyroprobe was set at 600° C. with a hold time of 10 s at a heating rate of 1000° C./s. The GC used a RESTEK RTX-1701 column (Restek, Bellefonte, Pa.), 60 m×0.25 mm with a 0.25 μm film thickness. The column gas flow was 1 cm/s with a split ratio of 1:100. The GC oven temperature program began with a 1 minute hold at 40° C. followed by heating at 8° C./min to 270° C. The injector and detector temperature was set at 280° C. The mass spectra were recorded in electron ionization mode for m/z 29 to 400. Identification of compounds was performed by comparing the mass spectra of the peaks with standard spectra of other compounds using the NIST library to obtain the most probable matches. Pure compounds (Sigma-Aldrich Co., St Louis, Mo.) were then used to confirm the peak identities based on matching of retention times and mass spectra.

GC/MS Analysis:

Liquid samples were analyzed using GC/MS (Shimadzu Corp., Columbia, Md.), with the conditions same as above. Quantification was performed using external standards. A four-point calibration curve using isobutanol as an internal standard was constructed to relate concentration to peak area response and quantify selected compounds in bio-oil.

Size Exclusion Chromatography (SEC) Analysis:

The molecular weight distribution of the water-soluble bio-oil fraction was determined using an AGILENT 1100 HPLC system equipped with a WATERS ULTRAHYDROGEL 250 7.8×300 mm column. A diode array detector (DAD) (260, 280 and 340 nm) and a refractive index detector were used to analyze the phenolic, carbohydrate and miscellaneous oxygenate compounds. The mobile phase was 0.1 M sodium nitrate and 0.01 M sodium hydroxide with a flow rate of 0.6 mL/min. The column temperature was set as 40° C. for SEC analysis. Samples were diluted two times using the mobile phase. Dextran standards were used to identify the molecular weight peaks for the carbohydrates in the bio-oil samples. No lignin standard was used, so the signal of the DAD detector provided a qualitative result in which larger molecules elute earlier in time relative to the smaller molecules.

Total Organic Carbon (TOC) Analysis:

The TOC content of the water-soluble bio-oil samples were analyzed in triplicate by a TOC analyzer. Standards with concentrations from 6.25 ppm to 50 ppm were used to quantify the TOC in the samples. As needed, samples were diluted to fit the TOC calibration range.

Electrochemical Efficiency (E.E.) Determination:

The amount of hydrogen generation was measured by water displacement using an inverted graduated cylinder. The E.E. was calculated according to the following equation: $E.E.=(I \times t - 2 \times n \times F)/(I \times t)$, where I is the current, t is the reaction time, n is the number of moles of hydrogen, and F is the Faraday constant.

Bio-Oil Aging:

In cases where bio-oil was artificially aged for comparison with its non-aged counterpart, water-soluble bio-oil (10-20 g) was weighed into a pressure tube. Afterward, the tube was carefully capped and placed in an oven at a temperature of 80° C. for 48 hr. After the aging, bio-oil was filtered with 0.22 μm syringe filter.

ECH of Water-Soluble Bio-Oil (Characterization):

Water-soluble bio-oil fractions before and after ECH were analyzed by GC/MS. As shown in Table 11, aldehydes and ketones were observed in the water-soluble bio-oil fraction before ECH, including formaldehyde, acetaldehyde, propanal, acetone, butanal, 2,3-butanedione, 2-butanone, glycolaldehyde, acetol, cyclohexanone, and 3-methyl-1,2-cyclopentanedione. After ECH, most of these compounds disappeared or were reduced significantly. Hydrogenation of these compounds was responsible for their decrease as many corresponding hydrogenation products were observed in the water-soluble fraction after 6.5 h ECH, such as ethanol, isopropanol, 2-propanol, 1-propanol, 2-butanol, tetrahydrofurfuryl alcohol, ethylene glycol, and propylene glycol. Representative reaction schemes are shown in Scheme 4.

TABLE 11

GC/MS chromatogram areas of ECH reactants and products, normalized relative to isobutanol internal standard

| Retention Time (min) | Component | Normalized Area | |
|---|---|---|---|
| | | Bio-oil in cathode chamber at t = 0 h | Bio-oil in cathode chamber at t = 6.5 h |
| 3.81 | Formaldehyde | 0.21 | 0.00 |
| 3.99 | Acetaldehyde | 0.77 | 0.00 |
| 4.09 | Methanol | 2.96 | 2.19 |
| 4.41 | Ethanol | 0.01 | 0.52 |
| 4.49 | Propanal | 0.17 | 0.00 |
| 4.57 | Acetone | 0.74 | 0.09 |
| 4.63 | Methyl acetate | 0.47 | 0.00 |
| 4.65 | 2-Propanol | 0.00 | 0.28 |
| 5.37 | 1-Propanol | 0.00 | 0.09 |
| 5.41 | Butanal | 0.08 | 0.00 |
| 5.54 | 2,3-Butanedione | 0.20 | 0.00 |
| 5.59 | 2-Butanone | 0.52 | 0.03 |
| 5.77 | 2-Butanol | 0.00 | 0.05 |
| 6.25 | Isobutanol (Internal standard) | 1.00 | 1.00 |
| 7.35 | Glycolaldehyde | 1.61 | 0.01 |
| 7.64 | Acetic acid | 6.90 | 3.09 |
| 8.39 | Acetol | 3.21 | 0.34 |
| 9.74 | Cyclopentanone | 0.08 | 0.06 |
| 10.34 | Ethylene glycol | 0.00 | 0.20 |
| 10.57 | Propylene glycol | 0.00 | 1.29 |
| 11.10 | Butanedial | 1.03 | 0.00 |

Scheme 4. Reaction schemes for ECH of organic compounds in water-soluble bio-oil

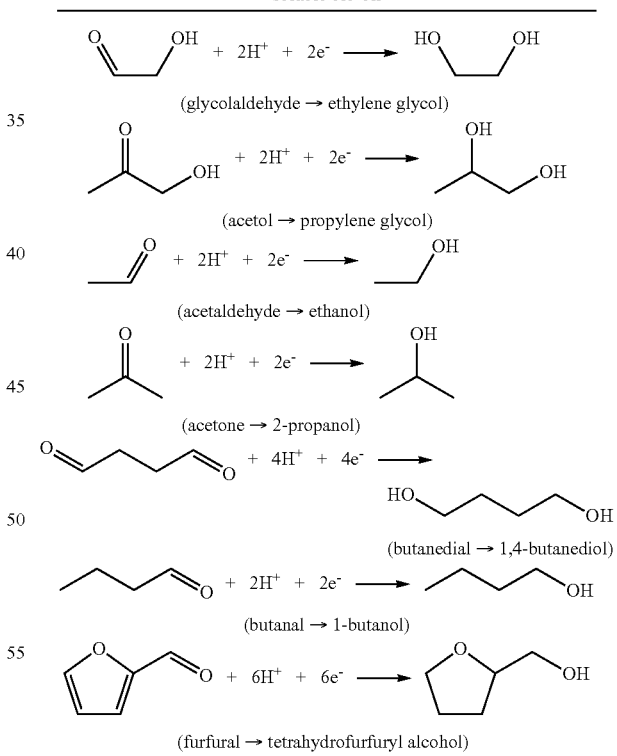

(glycolaldehyde → ethylene glycol)

(acetol → propylene glycol)

(acetaldehyde → ethanol)

(acetone → 2-propanol)

(butanedial → 1,4-butanediol)

(butanal → 1-butanol)

(furfural → tetrahydrofurfuryl alcohol)

As shown in Table 11, acetic acid decreases by more than 50% during ECH, indicating that compatibility with metal surfaces is improved as acetic acid is a major contributor to bio-oil corrosiveness. However, evidence that acetic acid is hydrogenated is lacking, as the mild conditions employed by ECH may not be sufficient to support such reduction. Instead, migration of acetic acid to the anode chamber through the membrane may be the major contribution to the decrease. This could be an alternative approach to reduce the carboxylic acids and the corrosiveness.

Some of the major products during ECH of water-soluble bio-oil were quantified by GC/MS (Table 12). Besides alcohol production, a relatively large amount of diols, such as ethylene glycol and propylene glycol, were produced with a total carbon yield of 10%. Other diols or polyols may be produced during ECH, such as 1,2-butanediol, 1,4-butanediol, sorbitol, etc. The yields of diols or polyols can be further improved by optimization of pyrolysis or better feedstock selection. As demonstrated in this example, ECH upgrading of the water-soluble bio-oil fraction can efficiently and effectively produce of diols or polyols at very mild conditions.

TABLE 12

GC/MS quantification of ECH products

| Component | Concentration (t = 0 h) | | Concentration (t = 6.5 h) | |
|---|---|---|---|---|
| | g/L | mmol-C/L (C %) | g/L | mmol-C/L (C %) |
| Ethanol | 0.01 | 0.43 | 0.28 | 12 (0.9%) |
| 1-Propanol | 0 | 0 | 0.12 | 5.8 (0.4%) |
| 1-Butanol | 0 | 0 | 0.06 | 3.4 (0.2%) |
| Tetrahydrofurfuryl alcohol | 0 | 0 | 0.05 | 2.6 (0.1%) |
| Ethylene glycol | 0 | 0 | 3.10 | 69 (5.0%) |
| Propylene glycol | 0 | 0 | 1.7 | 68 (5.0%) |
| TOC | | 1857 | | 1384 |

Besides the hydrogenation of aldehydes and ketones, other reasons contributing to compound decrease during ECH include polymerization of compounds, migration of compounds to the anode chamber by crossing the membrane, and adsorption onto the catalyst surface. Control experiments without electrical current were performed in the electrochemical cell (FIG. 24) to evaluate these factors. As shown in Table 13, a decrease of the reactants was observed in the control experiments, indicating that the aforementioned loss mechanisms are contributing to decreased chemical concentrations in addition to the ECH reactions.

TABLE 13

GC/MS chromatogram areas of ECH reactants, normalized relative to isobutanol internal standard (control experiment with no ECH performed)

| | | Normalized Area | |
|---|---|---|---|
| Retention Time (min) | Component | Bio-oil in cathode chamber at t = 0 h | Bio-oil in cathode chamber at t = 6.5 h |
| 3.81 | Formaldehyde | 0.21 | 0.16 |
| 3.99 | Acetaldehyde | 0.77 | 0.49 |
| 4.09 | Methanol | 2.96 | 1.52 |
| 4.49 | Propanal | 0.17 | 0.15 |
| 4.57 | Acetone | 0.74 | 0.47 |
| 4.63 | Methyl acetate | 0.47 | 0.34 |
| 5.41 | Butanal | 0.08 | 0.05 |
| 5.54 | 2,3-Butanedione | 0.20 | 0.17 |
| 5.59 | 2-Butanone | 0.52 | 0.38 |
| 6.25 | Isobutanol (Internal standard) | 1.00 | 1.00 |
| 7.35 | Glycolaldehyde | 1.61 | 0.47 |
| 7.64 | Acetic acid | 6.90 | 3.70 |
| 8.39 | Acetol | 3.21 | 2.51 |
| 11.10 | Butanedial | 1.03 | 0.40 |
| 13.82 | 3-Methyl-cyclopentanone | 0.29 | 0.10 |

TABLE 13-continued

GC/MS chromatogram areas of ECH reactants, normalized relative to isobutanol internal standard (control experiment with no ECH performed)

| | | Normalized Area | |
|---|---|---|---|
| Retention Time (min) | Component | Bio-oil in cathode chamber at t = 0 h | Bio-oil in cathode chamber at t = 6.5 h |
| 15.90 | 3-Methyl-1,2-cyclopentanedione | 0.57 | 0.26 |
| 16.35 | Phenol | 0.51 | 0.11 |
| 16.87 | Guaiacol | 0.12 | 0.03 |
| 22.44 | Syringol | 0.42 | 0.07 |
| 23.99 | 1,2,3-Trimethoxybenzene | 0.30 | 0.03 |
| 27.91 | Levoglucosan | 1.61 | 0.23 |

Figure 25:
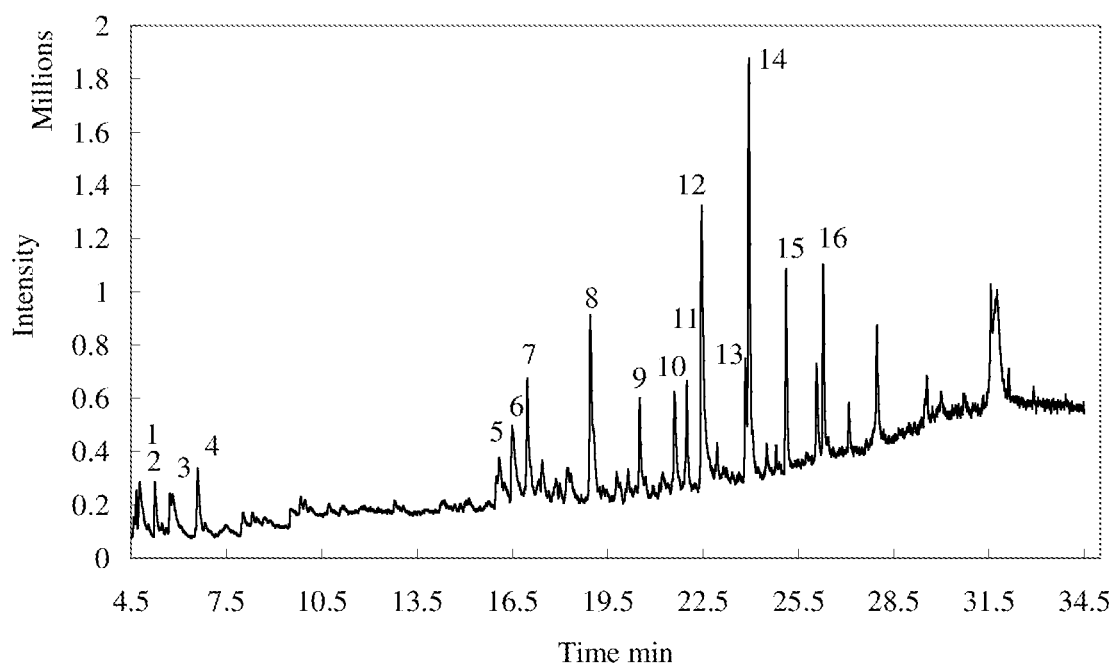
FIG. 25 is a pyrogram of the solids from ECH of water-soluble bio-oil. Peaks identified include: (1) acetone, (2) 2-methylfuran, (3) 2,3-butanedione, (4) 2,5-dimethylfuran, (5) 3-methyl-1,2-cyclopentanone, (6) phenol, (7) guaiacol, (8) 2-methoxy-4-methylphenol, (9) 4-ethyl-2-methoxyphenol, (10) 2-methoxy-4-vinylphenol, (11) 2-methoxy-4-propylphenol, (12) syringol, (13) 2-methoxy-4-(1-propenyl)-phenol, (14) 1,2,4-trimethoxybenzene, (15) 5-tert-butylpyrogallol, (16) 4-Methyl-2,5-dimethoxybenzaldehyde.

The oligomerization/polymerization of bio-oil constituents also was investigated as a potential loss mechanism. Although no coke formation was observed at these mild ECH conditions, small amounts of solid precipitated out in the cathode chamber during ECH. The solid was measured to be 8 mg after drying under vacuum (i.e., less than 0.1 wt. % of the 15 mL water-soluble bio-oil). Identification of the solid was performed using pyroprobe GC/MS (FIG. 25). A few small peaks for ketones and furans can be observed at the beginning of the chromatogram, and many phenolic compound peaks are detected at longer retention times. The solid was also dissolved in methanol and analyzed directly in GC/MS, and no peaks were observed. This indicates that the solid was made of phenolic and carbohydrate oligomers or polymers, formed from the polymerization reactions during ECH of the water-soluble bio-oil. Due to the fast consumption of the protons, it is possible that the local catholyte medium close to the catalyst had a high pH even though the bulk solution was still acidic. As basic conditions favored the polymerization of the phenolic compounds, increased homogeneity of the catholyte medium (e.g., by strong stirring/agitation or other mixing process) may maintain the pH value in the vicinity of the catalyst near to the desired low value of the bulk medium, potentially reducing the reactant consumption/product loss via undesired oligomerization/polymerization side reactions.

Figure 26:
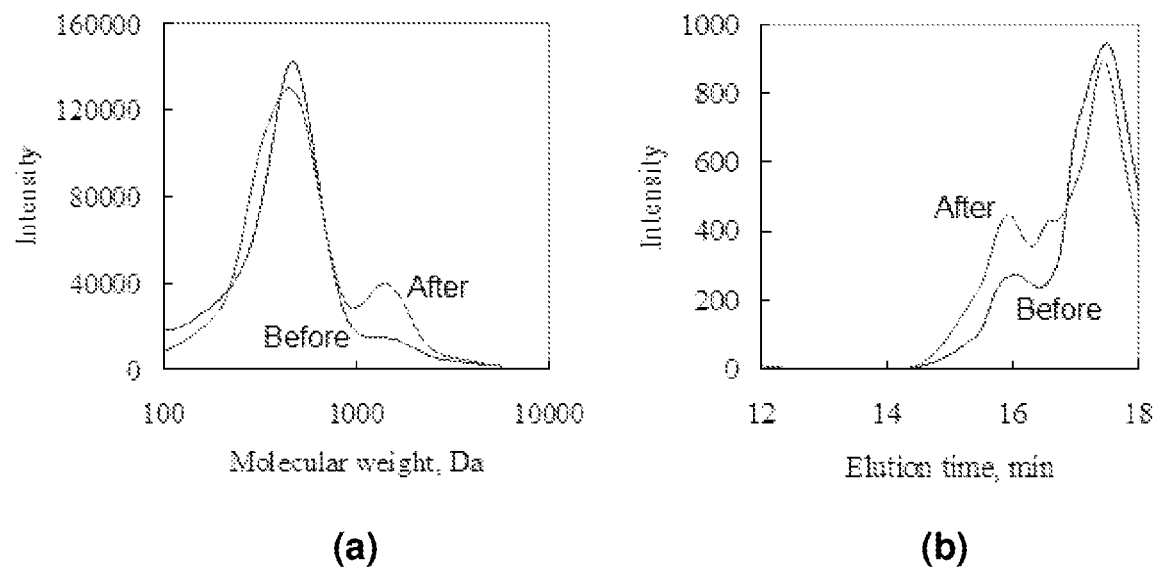
FIG. 26 includes size exclusion chromatograms of water-soluble bio-oil before and after ECH with (a) IR detector (left) and (b) DAD detector (260 nm) (right).

Precipitate formation indicates polymerization occurs during ECH of water-soluble bio-oil. To examine the molecular weight changes for the water-soluble bio-oil, size exclusion chromatography was used to measure the molecular weight distribution. As shown in FIG. 26(a), the intensity of the peak around 1400 Da increased after electrocatalytic hydrogenation. FIG. 26(b) also shows a significant increase at 16 min. Both of these increases indicate possible polymerization to form carbohydrates and phenolic oligomers during electrocatalytic hydrogenation. The mild ECH conditions employed in this investigation were selected to slow the polymerization of bio-oil during ECH, however, the pH increase of the local solution close to the cathode and the presence of a large concentration of electrolyte may enhance the polymerization. Solid polymer electrolyte electrochemical cells can eliminate the use of electrolyte. With the improvement of these conditions, polymerization during ECH can be greatly reduced.

The organic compound migration and adsorption onto the cathode were examined by analyzing the carbon distribution in different parts of the electrochemical cell with a TOC analyzer (Table 14 below). Control experiments without electricity were first performed to check the carbon distribution. After 6.5 h, 81% was retained in the cathode chamber. However, 12% carbon was transferred to the anode chamber due to the organic concentration gradient. The catalytic cathode also adsorbed 4.0% carbon, and the remaining 3% carbon loss may be due to the organics trapped in the membrane during the migration of the organic compounds to the anode chamber.

After 6.5 h ECH reaction, there was about 80% carbon retained in the cathode chamber, and 6.0% carbon was detected in the anode chamber due to the migration through the membrane. The cathode adsorbed about 2.6% carbon and 0.2% was trapped in the downstream water trapping system. The total carbon identified in the whole system was about 88.8%. The solid formed during ECH contributed to part of the carbon loss. Organics trapped in the membrane may be another source for the carbon loss as the membrane turned black after the ECH reaction. The other important carbon loss may be due to the oxidation of the organics on the anode as the carbon content in the anode was lower than that for the control experiments. Small organic compounds, such as methanol, ethanol, formic acid and acetic acid, can migrate through the membrane to the anode side. These organic compounds can be oxidized to form carbon dioxide under the anode conditions (high overpotential and 1 M sulfuric acid). Modification of the membrane to reduce the transport of small organic compounds to the anode chamber is possible. In any event, the carbon retention is still comparatively better than that in the catalytic hydrogenation (e.g., carbon retention of about 75% and 64% during hydrogenation of the water-soluble bio-oil at 150° C. and 175° C.).

TABLE 14

TOC bio-oil analysis (control vs. ECH experiments)

| Time (h) | | TOC (Control) | TOC (ECH) |
|---|---|---|---|
| 0 | Water-soluble bio-oil (cathode) - initial | 100% | 100% |
| 6.5 | Water-soluble bio-oil (cathode) - final | 81% | 80% |
| 6.5 | Anode solution | 12% | 6.0% |
| 6.5 | Organics adsorbed on the cathode | 4.0% | 2.6% |
| 6.5 | Organics in the trapping system | — | 0.2% |
| 6.5 | Total (after ECH) | 97% | 88.8% |
| 6.5 | Others | 3% | 11.2% |

TOC values normalized to 100% relative to initial value prior to control/ECH experiment ECH of Water-Soluble Bio-Oil (Stability):

The water-soluble bio-oil after ECH treatment was less reactive, as the majority of the carbonyl groups were hydrogenated to more stable alcohols or diols. To confirm the stability of the ECH treated bio-oil, an accelerated aging test was performed at 80° C. for 48 h. SEC and viscosity measurement were used to characterize the bio-oil before and after the aging tests.

Figure 27:
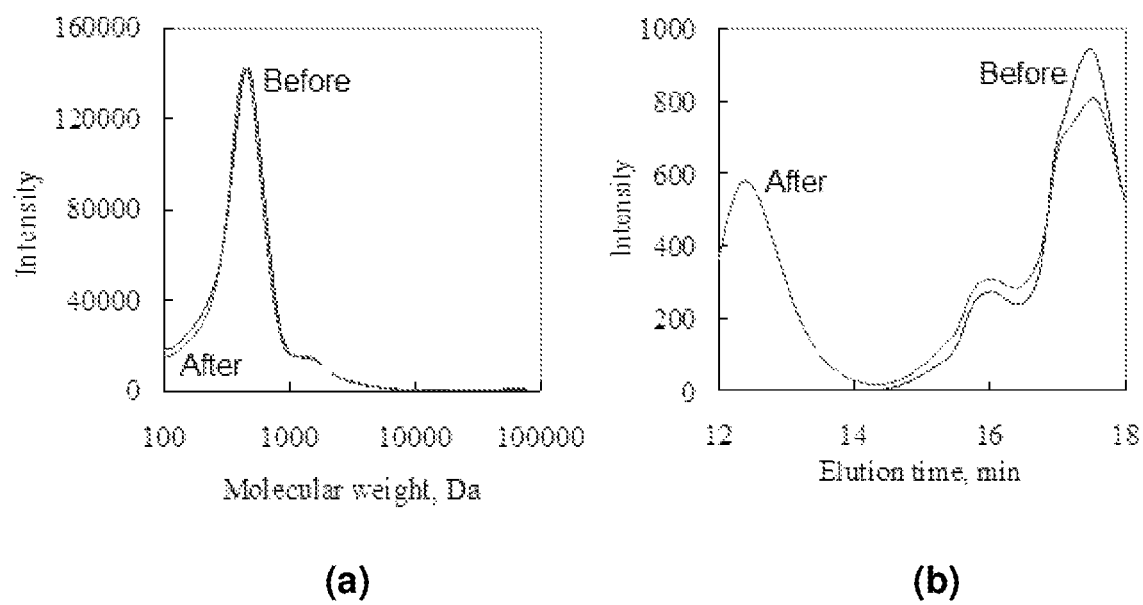
FIG. 27 includes size exclusion chromatograms of water-soluble bio-oil without ECH treatment before and after aging with (a) IR detector (left) and (b) DAD detector (260 nm) (right).

Controlled aging studies were first performed on the water-soluble bio-oil without treatment by ECH. Size exclusion chromatography (SEC) was used to analyze the molecular weight distribution before and after aging for the water-soluble bio-oil. The molecular weight of the carbohydrates did not change very much after aging (FIG. 27(a)). The molecular weight of lignin-derived compounds, however, increased significantly as a big peak showed up before 14 min (FIG. 27(b)). This molecular weight increase could be due to reactions of phenol or substituted phenols with aldehydes.

Figure 28:
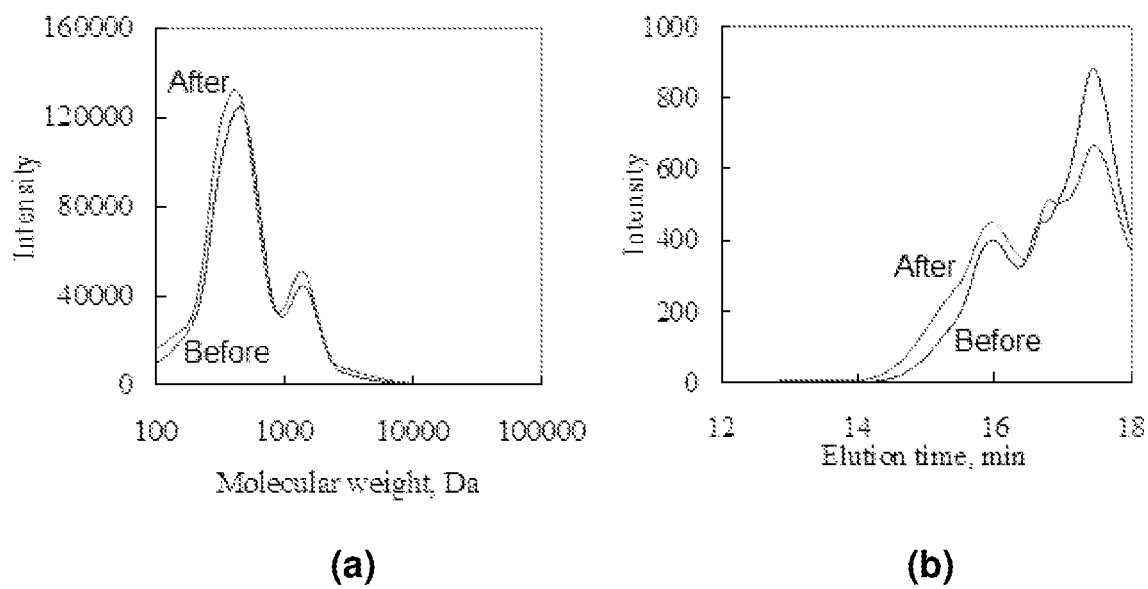
FIG. 28 includes size exclusion chromatograms of water-soluble bio-oil with ECH treatment before and after aging with (a) IR detector (left) and (b) DAD detector (260 nm) (right).

The ECH-treated water-soluble bio-oil was also subjected to an accelerated aging test. SEC analysis showed that the molecular weights of both the carbohydrates (FIG. 28(a)) and lignin-derived compounds (FIG. 28(b)) increased slightly. Compared with the water-soluble bio-oil without ECH treatment, however, the molecular weight of ECH-treated bio-oil did not increase very much as no peak showed up before 14 min for the lignin-derived molecules. This result indicates that ECH treatment can slow bio-oil aging as the carbonyl groups are hydrogenated during the ECH process.

Figure 29:
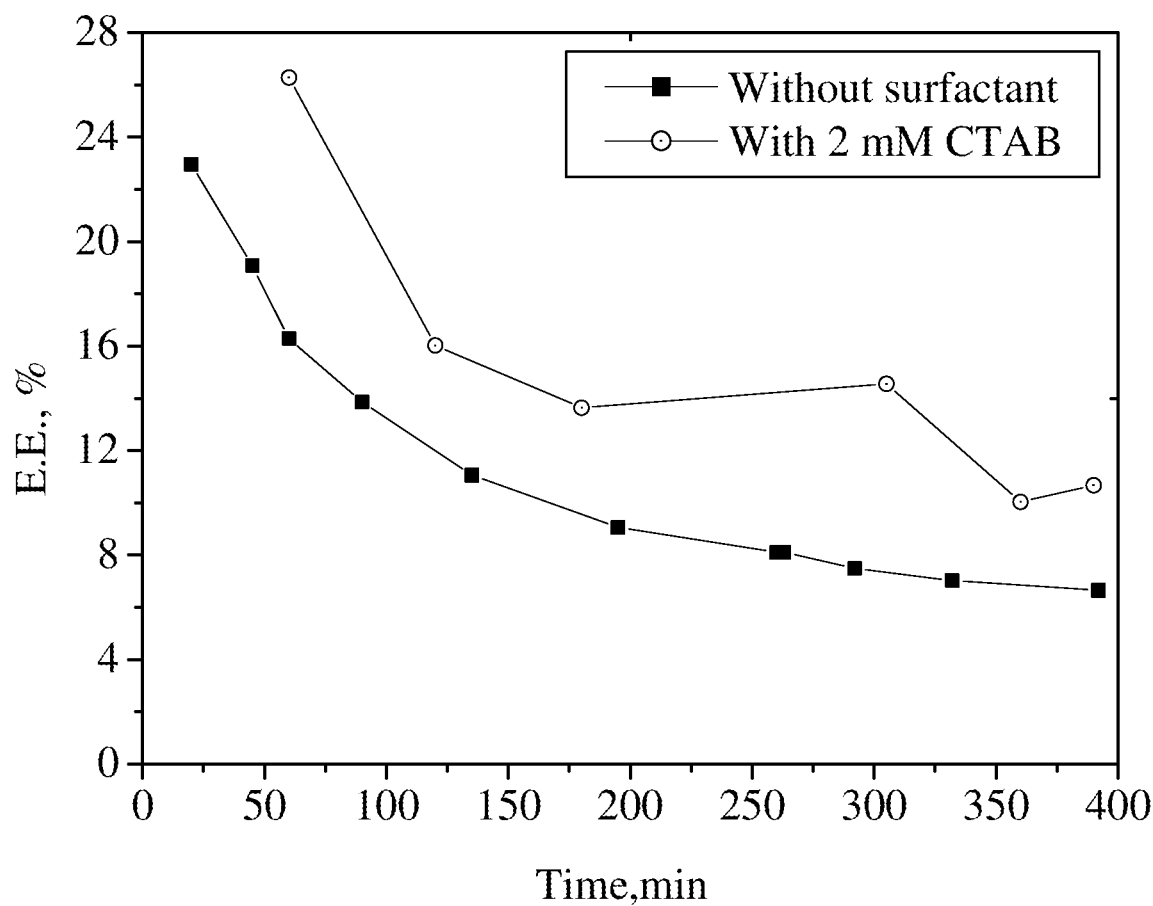
FIG. 29 is a graph illustrating changes in electrochemical efficiency vs. reaction time with and without surfactant (cetyltrimethylammonium bromide; CTAB) during ECH of water-soluble bio-oil using Re3/ACC-IW-NH3.

ECH of Water-Soluble Bio-Oil (Efficiency):

Electrochemical efficiency is important for ECH of bio-oil because it influences the energy efficiency and the operation cost of the process. Hydrogen production, a side reaction, contributes to the low electrochemical efficiency. At the beginning of the ECH process, the electrochemical efficiency was about 23%. As the reaction progressed, however, electrochemical efficiency decreased to 7% at the end of the 6.5 hr reaction (FIG. 29). The decrease may result from the solution pH change and/or the coverage of the catalyst by solids formed during the ECH (e.g., as the active sites for the hydrogenation decrease, the hydrogenation rate decreases and the hydrogen production rate increases). As further shown in FIG. 29, the electrochemical efficiency can be improved by a differential value of about 4% to 10% when adding a surfactant to the reaction medium (2 mM cetyltrimethylammonium bromide (CTAB) in the illustrative example). Produced hydrogen can be recovered as a valuable product and used in the downstream upgrading, thus improving the economics of the process.

Other techniques may be used to improve process efficiency. For example, a solid polymer electrolyte ECH cell can be used to reduce the inter-electrode distance and decrease the solution resistance significantly. In such a design, the applied voltage can be greatly reduced and the energy efficiencies can be increased. Further, although a large excess of water was used in the example for bio-oil extraction and dilution (e.g., creating a significant downstream product separation cost and/or environmental concern), substantially less water can be used to separate bio-oil as phase separation occurs with a water:bio-oil ratio as little as about 1:8.

Summary:

ECH can convert most of the aldehydes and ketones in bio-oil (or the water-soluble fraction thereof as illustrated) to the corresponding alcohols. SEC analyses showed that bio-oil with ECH treatment was more stable compared with bio-oil without ECH treatment. A better carbon recovery (>80%) into the liquid phase was also obtained during ECH of water-soluble bio-oil. Although solids were observed during ECH, the amount of solid material (less than 0.1 wt. %) was substantially less than solids formed via catalytic hydrogenation of bio-oil. Valuable products, such as hydrogen, ethylene glycol and propylene glycol, can be recovered after ECH of water-soluble bio-oil, thus providing an attractive approach to upgrade the bio-oil fraction into stable fuel intermediates and valuable chemicals. This methods illustrated in the example can be extended to other high concentration water-soluble bio-oils with much less water content and/or other bio-oil fractions (e.g., water-soluble bio-oil, water-insoluble/solvent-soluble bio-oil, complete distribution of bio-oil pyrolysis products).

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compositions, processes, kits, or apparatus are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

REFERENCES

1. J. Ebert, 2008. http://biomassmagazine.com/articles/1950/furfural-future-feedstock-for-fuels-and-chemicals.
2. M. J. Taherzadeh, L. Gustafsson, C. Niklasson, G. Liden, J. Biosci. Bioeng. 90 (2000) 374.
3. R. S. Rao, R. T. K. Baker, M. A. Vannice, Catal. Lett. 60 (1999) 51.
4. Y. L. Zhu, H. W. Xiang, Y. W. Li, H. J. Jiao, G. S. Wu, B. Zhong, G. Q. Guo, New J. Chem. 27 (2003) 208.
5. H. Y. Zheng, Y. L. Zhu, B. T. Teng, Z. Q. Bai, C. H. Zhang, H. W. Xiang, Y. W. Li, J. Mol. Catal. A: Chem. 246 (2006) 18.
6. D. B. Chu, Y. Y. Hou, J. G. He, M. Xu, Y. Q. Wang, S. X. Wang, J. Wang, L. W. Zha, J. Nanoparticles Res. 11 (2009) 1805.
7. S. G. Kulkarni, V. S. Bagalkote, S. S. Patil, U. P. Kumar, V. A. Kumar, Propell. Explos. Pyrot. 34 (2009) 520.
8. S. Gouli, E. Lois, S. Stournas, Energy Fuel 12 (1998) 918.
9. J. Yang, H. Y. Zheng, Y. L. Zhu, G. W. Zhao, C. H. Zhang, B. T. Teng, H. W. Xiang, Y. W. Li, Catal. Commun. 5 (2004) 505.
10. J. Lessard, J. F. Morin, J. F. Wehrung, D. Magnin, E. Chornet, Top. Catal. 53 (2010) 1231.
11. C. M. Cirtiu, A. Brisach-Wittmeyer, H. Ménard, J. Catal. 245 (2007) 191.
12. D. Tountian, A. Brisach-Wittmeyer, P. Nkeng, G. Poillerat, H. Ménard, J. Appl. Electrochem. 39 (2009) 411.
13. B. Mahdavi, J. M. Chapuzet, J. Lessard, Electrochim. Acta 38 (1993) 1377.
14. D. Robin, M. Comtois, A. Martel, R. Lemieux, A. K. Cheong, G. Belot, J. Lessard, Can. J. Chem. 68 (1990) 1218.
15. P. Parpot, A. P. Bettencourt, G. Chamoulaud, K. B. Kokoh, E. M. Beigsir, Electrochim. Acta 49 (2004) 397.
16. G. Chamoulaud, D. Floner, C. Moinet, C. Lamy, E. M. Belgsir, Electrochim. Acta 46 (2001) 2757.
17. D. Navarro, M. Navarro, J. Chem. Educ. 81 (2004) 1350.
18. D. S. Santana, G. O. Melo, M. V. F. Lima, J. R. R. Daniel, M. C. C. Areias, M. Navarro, J. Electroanal. Chem. 569 (2004) 71.
19. M. V. F. Lima, F. D. Menezes, B. de Barros, M. Navarro, J. Electroanal. Chem. 613 (2008) 58.
20. A. P. da Silva, S. D. C. Mota, L. W. Bieber, M. Navarro, Tetrahedron 62 (2006) 5435.
21. M. Vilar, J. L. Oliveira, M. Navarro, Appl. Catal. A: Gen. 372 (2010) 1.
22. V. D. Vaart, Electrocatalytic Hydrocracking, Virginia Polytechnic Institute and State University, Blacksburg, 1992, p. 1.
23. R. H. Venderbosch, A. R. Ardiyanti, J. Wildschut, A. Oasmaa and H. J. Heeres, Journal of Chemical Technology & Biotechnology 85 (2010) 674-686.
24. L. Moens, S. K. Black, M. D. Myers and S. Czernik, Energy & Fuels 23 (2009) 2695-2699.
25. T. P. Vispute and G. W. Huber, Green Chemistry 11 (2009) 1433-1445.
26. F. H. Mahfud, F. Ghijsen and H. J. Heeres, Journal of Molecular Catalysis A: Chemical 264 (2007) 227-236.
27. L. Busetto, D. Fabbri, R. Mazzoni, M. Salmi, C. Torri and V. Zanotti, Fuel 90 (2010) 1197-1207.
28. F. H. Mahfud, S. Bussemaker, B. J. Kooi, G. H. Ten Brink and H. J. Heeres, Journal of Molecular Catalysis A: Chemical 277 (2007) 127-136.
29. A. Oasmaa and E. Kuoppala, Energy & fuels 17 (2003) 1075-1084.
30. S. Czernik and A. V. Bridgwater, Energy & Fuels 18 (2004) 590-598.
31. C. Zhao, J. He, A. A. Lemonidou, X. Li and J. A. Lercher, Journal of Catalysis 280 (2011) 8-16.
32. B. Scholze and D. Meier, Journal of Analytical and Applied Pyrolysis 60 (2001) 41-54.
33. T. Vispute in Pyrolysis Oils: Characterization, Stability Analysis, and Catalytic Upgrading to Fuels and Chemicals, Vol. Doctor of Philosophy University of Massachusetts—Amherst, Amherst, 2011, p. 174.
34. F. Laplante, L. Brossard and H. Ménard, Canadian journal of chemistry 81 (2003) 258-264.
35. A. Brisach-Wittmeyer, N. A. Bouchard, R. Breault and H. Ménard, Canadian journal of chemistry 84 (2006) 1640-1647.
36. H. Ilikti, N. Rekik and M. Thomalla, Journal of applied electrochemistry 34 (2004) 127-136.
37. H. Ilikti, N. Rekik and M. Thomalla, Journal of applied electrochemistry 32 (2002) 603-609.
38. K. Amouzegar and O, Savadogo, Journal of applied electrochemistry 27 (1997) 539-542.
39. B. Mahdavi, P. Chambrion, J. Binette, E. Martel and J. Lessard, Canadian Journal of Chemistry-Revue Canadienne De Chimie 73 (1995) 846-852.
40. A. Cyr, F. Chiltz, P. Jeanson, A. Martel, L. Brossard, J. Lessard and H. Menard, Canadian Journal of Chemistry-Revue Canadienne De Chimie 78 (2000) 307-315.
41. H. M. Jean-Marc Lalancette, Estelle Potvin in Phosphate bonded composite electrodes Vol. 4886591 US, 1989.
42. P. Dabo, A. Cyr, J. Lessard, L. Brossard and H. Menard, Canadian journal of chemistry 77 (1999) 1225-1229.
43. P. Dube, F. Kerdouss, F. Laplante, P. Proulx, L. Brossard and H. Menard, Journal of applied electrochemistry 33 (2003) 541-547.
44. A. Cyr, F. Chiltz, P. Jeanson, A. Martel, L. Brossard, J. Lessard and H. Ménard, Canadian Journal of Chemistry 78 (2000) 307-315.
45. J. R. Rangel-Mendez and M. Streat, Water Research 36 (2002) 1244-1252.
46. J. Aumo, S. Oksanen, J. P. Mikkola, T. Salmi and D. Y. Murzin, Industrial & engineering chemistry research 44 (2005) 5285-5290.

47. C. Zhao, Y. Kou, A. A. Lemonidou, X. Li and J. A. Lercher, Angewandte Chemie 121 (2009) 4047-4050.
48. T. S. Dalavoy, J. E. Jackson, G. M. Swain, D. J. Miller, J. Li and J. Lipkowski, Journal of Catalysis 246 (2007) 15-28.
49. Z. Zhang, J. E. Jackson and D. J. Miller, Applied Catalysis A: General 219 (2001) 89-98.
50. K. P. Pimparkar, D. J. Miller and J. E. Jackson, Industrial & Engineering Chemistry Research 47 (2008) 7648-7653.
51. J. Wildschut, F. H. Mahfud, R. H. Venderbosch and H. J. Heeres, Industrial & Engineering Chemistry Research 48 (2009) 10324-10334.
52. B. K. Pradhan and N. K. Sandle, Carbon 37 (1999) 1323-1332.
53. M. Besson, P. Gallezot, A. Perrard and C. Pinel, Catalysis today 102 (2005) 160-165.
54. A. Sluiter, B. Hames, R. Ruiz, C. Scarlata, J. Sluiter and D. Templeton in Determination of Ash in Biomass, Vol. National Renewable Energy Laboratory, Golden, 2005, pp. 1-5.
55. M. Perez, C. Salinas Martinez de Lecea and A. Linares Solano, Applied Catalysis A: General 151 (1997) 461-475.
56. C. M. Cirtiu, H. O. Hassani, N. A. Bouchard, P. A. Rowntree and H. Menard, Langmuir 22 (2006) 6414-6421.
57. J. Wildschut, I. V. Melian-Cabrera and H. J. Heeres, Applied Catalysis B: Environmental 99 (2010) 298-306.
58. M. Nurunnabi, K. Murata, K. Okabe, T. Hanaoka, T. Miyazawa and K. Sakanishi, Journal of the Japan Petroleum Institute 53 (2010) 75-81.
59. E. Diaz, A. F. Mohedano, L. Calvo, M. A. Gilarranz, J. A. Casas and J. J. Rodriguez, Chemical Engineering Journal 131 (2007) 65-71.
60. Y. C. Lin, C. L. Li, H. P. Wan, H. T. Lee and C. F. Liu, Energy & Fuels 25 (2011) 890-896.
61. A. Gutierrez, R. K. Kaila, M. L. Honkela, R. Slioor and A. O. I. Krause, Catalysis Today 147 (2009) 239-246.
62. A. Roessler, O. Dossenbach and P. Rys, Journal of the Electrochemical Society 150 (2003) D1-D5.
63. K. Amouzegar and O, Savadogo, Electrochimica acta 39 (1994) 557-559.
64. A. Solladié-Cavallo, A. Baram, E. Choucair, H. Norouzi-Arasi, M. Schmitt and F. Garin, Journal of Molecular Catalysis A: Chemical 273 (2007) 92-98.
65. B. J. Arena, Applied Catalysis A: General 87 (1992) 219-229.
66. M. Ragnar, C. T. Lindgren and N. O, Nilvebrant, Journal of wood chemistry and technology 20 (2000) 277-305.
67. M. Besson, P. Gallezot, A. Perrard, C. Pinel, Catalysis Today 102-103 (2005) 160-165.
68. A. Perrard, P. Gallezot, J.-P. Joly, R. Durand, C. Baljou, B. Coq, P. Trens, Applied Catalysis A: General 331 (2007) 100-104.
69. P. Parmentier, J.-P. Joly, and A. Perrard, U.S. Pat. No. 6,383,972

What is claimed is:

1. A process for performing electrocatalytic hydrogenation (ECH) and optionally electrocatalytic hydrodeoxygenation (ECHDO) of an organic substrate, the process comprising:
    (a) providing a reaction mixture comprising at least one of a multicomponent bio-oil and a multicomponent bio-oil fraction, which comprises a plurality of different organic reactants each comprising an aromatic CH group and being selected from the group consisting of hydroxy-substituted aromatic compounds, methoxy-substituted aromatic compounds, oligomerization products thereof, and combinations thereof;
    (b) contacting the reaction mixture with a first electrode comprising a catalytic electrode composition comprising (i) a porous activated carbon cloth (ACC) support and (ii) metal catalyst particles immobilized on the ACC support, wherein:
        the metal catalyst particles comprise a metal selected from the group consisting of Ru, Fe, Cu, Pt, Rh, Ir, Re, Os, Ag, Au, Co, Mo, Ga, mixtures thereof, alloys thereof, and combinations thereof;
        the metal catalyst particles of the first electrode are capable of catalyzing ECH of aromatic CH groups to form corresponding $CH_2$ groups,
        the metal catalyst particles immobilized on the ACC support are not mobile, and
        the metal catalyst particles have been immobilized on the ACC support prior to contacting the ACC support with (i) the reaction mixture or (ii) one or more of water or a water-miscible solvent to which the plurality of organic reactants is added to form the reaction mixture;
    (c) electrically contacting the reaction mixture with a second electrode; and
    (d) applying an electrical potential between the first electrode and the second electrode to provide an electrical current therebetween and through the reaction mixture, thereby performing an ECH reaction to reduce the aromatic CH group of each of the plurality of organic reactants and to form ECH reaction products thereof each comprising a $CH_2$ group, wherein at least one of the plurality of organic reactants has a conversion of at least 0.8.

2. The process of claim 1, further comprising:
    (e) recovering or separating the ECH reaction products from the reaction mixture.

3. The process of claim 1, wherein:
    the reaction mixture further comprises an organic compound comprising a carbonyl carbon-oxygen double bond present in a functional group selected from the group consisting of ketone groups, aldehyde groups, carboxylic acid groups, ester groups, amide groups, enone groups, acyl halide groups, acid anhydride groups, and combinations thereof; and
    applying the electrical potential further performs an ECHDO reaction to deoxygenate the carbonyl carbon-oxygen double bond.

4. The process of claim 1, wherein the aromatic CH group is present in a functional group selected from the group consisting of benzenes, phenols, furans, pyridines, pyrazines, imidazoles, pyrazoles, oxazoles, thiophenes, naphthalenes, higher fused aromatics, and combinations thereof.

5. The process of claim 1, wherein the reaction mixture further comprises an organic compound comprising a C=O group, and the ECH reaction further reduces the C=O group to form a corresponding ECH reaction product comprising at least one of a C—OH group and a $CH_2$ group.

6. The process of claim 1, wherein the reaction mixture further comprises an organic compound comprising an ethylenic C=C group, and the ECH reaction further reduces the ethylenic C=C group to form a corresponding ECH reaction product comprising a CH—CH group.

7. The process of claim 1, wherein the reaction mixture further comprises an organic compound comprising a C—OH group, and applying the electrical potential further performs an ECHDO reaction to deoxygenate the C—OH group to form a corresponding ECHDO reaction product comprising a CH group.

8. The process of claim 1, wherein the reaction mixture further comprises an organic compound comprising a (C=O)O group, and applying the electrical potential further performs an ECHDO reaction to deoxygenate the (C=O)O group to form a corresponding ECHDO reaction product comprising at least one of a (C=O)H group and a C—OH group.

9. The process of claim 1, wherein the reaction mixture further comprises an organic compound comprising an ether $R_1$-O-$R_2$ group, and applying the electrical potential further performs an ECH reaction to reduce the ether $R_1$-O-$R_2$ group and an ECHDO reaction to deoxygenate the ether $R_1$-O-$R_2$ group to form corresponding ECH or ECHDO reaction products comprising one or more of a $R_1H$, $R_2OH$, $R_1OH$, and $R_2H$, where $R_1$ and $R_2$ are substituents containing from 1 to 10 carbon atoms.

10. The process of claim 1, wherein the bio-oil is a reaction product produced from fast pyrolysis of biomass.

11. The process of claim 1, wherein the reaction mixture is free from added solvents.

12. The process of claim 1, wherein the reaction mixture further comprises one or more of the water or the water-miscible organic solvent.

13. The process of claim 1, wherein the reaction mixture further comprises the water, and the water is present in an amount ranging from 10 wt. % to 95 wt. % relative to the reaction mixture.

14. The process of claim 1, wherein the reaction mixture comprises the multicomponent bio-oil fraction, the multicomponent bio-oil fraction having been obtained by extraction of bio-oil using a solvent comprising one or more of water, methanol, ethanol, diethyl ether, ethyl acetate, dichloromethane, chloroform, toluene, and hexane.

15. The process of claim 1, wherein the plurality of different organic reactants is selected from the group consisting of phenol, guaiacol, syringol, substituted derivatives thereof, and combinations thereof.

16. The process of claim 1, wherein the ECH reaction products comprise cyclohexanol.

17. The process of claim 1, wherein the reaction mixture further comprises an electrolyte.

18. The process of claim 1, wherein the second electrode comprises an electrically conductive material selected from the group consisting of Ni, Pt, carbon, lead, lead dioxide, mixtures thereof, alloys thereof, and combinations thereof.

19. The process of claim 1, comprising performing the ECH reaction and optionally an ECHDO reaction in a divided electrochemical cell containing the reaction mixture, wherein:
(i) the second electrode is in contact with an anolyte mixture in electrical connection with the reaction mixture via an ion-exchange membrane;
(ii) the reaction mixture further comprises carboxylic acids, and
(iii) the process further comprises removing at least some of the carboxylic acids from the reaction mixture into the anolyte mixture via the ion-exchange membrane.

20. The process of claim 1, wherein the ECH reaction products and optionally an ECHDO reaction product contains at least 80% of the carbon initially contained in the reaction mixture.

21. The process of claim 1, wherein the first electrode is capable of catalyzing the electrocatalytic hydrogenation (ECH) and optionally the electrocatalytic hydrodeoxygenation (ECHDO).

22. The process of claim 1, wherein the first electrode is capable of catalyzing (i) ECH of unsaturated carbon-carbon bonds in the plurality of organic reactants, optionally (ii) ECH of carbon-oxygen double bonds in the plurality of organic reactants, and optionally (iii) ECHDO of carbon-oxygen single bonds in the plurality of organic reactants.

23. The process of claim 1, wherein:
(i) the metal catalyst particles comprise nanoparticles ranging in size from 1 nm to 200 nm; and
(ii) the metal catalyst particles have metal dispersions ranging from 1% to 90%.

24. The process of claim 1, wherein:
(i) the ACC is in the form of a flexible woven or knitted monolithic support;
(ii) the ACC support prior to metal particle immobilization has a microporous structure with a specific BET surface ranging from 800 $m^2/g$ to 3000 $m^2/g$;
(iii) the ACC support prior to metal particle immobilization has a microporous structure with a specific micropore surface area ranging from 500 $m^2/g$ to 2100 $m^2/g$;
(iv) the ACC support prior to metal particle immobilization has a microporous structure with a specific micropore volume ranging from 0.2 $cm^3/g$ to 1.0 $cm^3/g$;
(v) the catalytic electrode composition has a microporous structure with a specific BET surface area relative to that of the ACC support prior to metal particle immobilization ranging from 0.1 to 0.9;
(vi) the catalytic electrode composition has a microporous structure with a specific micropore surface area relative to that of the ACC support prior to metal particle immobilization ranging from 0.1 to 0.9; and
(vii) the catalytic electrode composition has a microporous structure with a specific micropore volume relative to that of the ACC support prior to metal particle immobilization ranging from 0.1 to 0.9.

25. The process of claim 1, wherein the first electrode is in continuous electrical connection with a source of at least one of the electrical voltage potential and the electrical current.

26. The process of claim 1, wherein the ACC support and the metal catalyst particles immobilized thereon are together in a monolithic form as the catalytic electrode composition.

27. The process of claim 1, wherein the metal catalyst particles have been immobilized on the ACC support by performing at least one of an incipient wetness impregnation process and an ion exchange process.

28. The process of claim 1, wherein the metal catalyst particles comprise a metal selected from the group consisting of Ru, Cu, Pt, mixtures thereof, alloys thereof, and combinations thereof.

29. The process of claim 1, wherein the metal catalyst particles comprise Ru.

30. The process of claim 1, wherein:
applying the electrical potential in part (d) comprises reducing each of the organic reactants to form the ECH reaction products thereof comprising a $CH_2$ group and each having a conversion of at least 0.8.

31. The process of claim 1, wherein:
the bio-oil is a reaction product produced from fast pyrolysis of biomass;

the reaction mixture further comprises the water, and the water is present in an amount ranging from 10 wt. % to 95 wt. % relative to the reaction mixture; and the metal catalyst particles comprise a metal selected from the group consisting of Ru, Cu, Pt, mixtures thereof, alloys thereof, and combinations thereof.

32. The process of claim 1, wherein the reaction mixture comprises the multicomponent bio-oil.

33. The process of claim 1, wherein the reaction mixture comprises the multicomponent bio-oil fraction.

* * * * *